US010633394B2

(12) United States Patent
Park et al.

(10) Patent No.: US 10,633,394 B2
(45) Date of Patent: Apr. 28, 2020

(54) HETEROCYCLIC DERIVATIVES AND USE THEREOF

(71) Applicant: C & C RESEARCH LABORATORIES, Suwon-si, Gyeonggi-do (KR)

(72) Inventors: Chan Hee Park, Suwon-si (KR); Sang Hwi Lee, Suwon-si (KR); Junhwan Im, Suwon-si (KR); Soon Ok Lee, Suwon-si (KR); Jungsook Kim, Suwon-si (KR); Heon Kyu Park, Suwon-si (KR); Jee Hun Yun, Suwon-si (KR); Kwang Seok Ko, Suwon-si (KR); Hye Jung Kim, Suwon-si (KR); Byungho Kim, Suwon-si (KR); Mi Sun Kim, Suwon-si (KR); Minjung Kong, Suwon-si (KR); Hyung Jo Moon, Suwon-si (KR)

(73) Assignee: C&C RESEARCH LABORATORIES, Suwon-si (KR)

( * ) Notice: Subject to any disclaimer, the term of this patent is extended or adjusted under 35 U.S.C. 154(b) by 271 days.

(21) Appl. No.: 15/528,571

(22) PCT Filed: Nov. 30, 2015

(86) PCT No.: PCT/KR2015/012926
§ 371 (c)(1),
(2) Date: May 22, 2017

(87) PCT Pub. No.: WO2016/089062
PCT Pub. Date: Jun. 9, 2016

(65) Prior Publication Data
US 2019/0119297 A1 Apr. 25, 2019

(30) Foreign Application Priority Data

Dec. 2, 2014 (KR) .................. 10-2014-0170860
Sep. 10, 2015 (KR) .................. 10-2015-0128025

(51) Int. Cl.
| | | |
|---|---|---|
| C07D 498/04 | (2006.01) |
| C07D 413/14 | (2006.01) |
| C07D 333/70 | (2006.01) |
| C07D 409/04 | (2006.01) |
| C07D 409/12 | (2006.01) |
| C07D 409/14 | (2006.01) |
| C07D 413/06 | (2006.01) |
| C07D 209/42 | (2006.01) |
| C07D 487/04 | (2006.01) |
| C07D 417/14 | (2006.01) |
| C07D 471/04 | (2006.01) |
| C07D 487/10 | (2006.01) |
| C07D 495/04 | (2006.01) |
| A61P 35/00 | (2006.01) |

(52) U.S. Cl.
CPC ............ *C07D 498/04* (2013.01); *A61P 35/00* (2018.01); *C07D 209/42* (2013.01); *C07D 333/70* (2013.01); *C07D 409/04* (2013.01); *C07D 409/12* (2013.01); *C07D 409/14* (2013.01); *C07D 413/06* (2013.01); *C07D 413/14* (2013.01); *C07D 417/14* (2013.01); *C07D 471/04* (2013.01); *C07D 487/04* (2013.01); *C07D 487/10* (2013.01); *C07D 495/04* (2013.01)

(58) Field of Classification Search
CPC .................................................. C07D 498/04
USPC .......................................................... 549/43
See application file for complete search history.

(56) References Cited

U.S. PATENT DOCUMENTS

| | | | |
|---|---|---|---|
| 6,057,335 | A | 5/2000 | Fukami et al. |
| 2005/0261350 | A1 | 11/2005 | McConnel et al. |
| 2009/0264405 | A1 | 10/2009 | Ali et al. |
| 2012/0251491 | A1 | 10/2012 | Rosenblum et al. |
| 2014/0072630 | A1 | 3/2014 | Tao et al. |

FOREIGN PATENT DOCUMENTS

| | | |
|---|---|---|
| EP | 1598353 A1 | 11/2005 |
| WO | 94/02483 A1 | 2/1994 |
| WO | 02/100852 A1 | 12/2002 |
| WO | 2008/124000 A2 | 10/2008 |
| WO | 2010144404 A1 | 12/2010 |
| WO | 2013/096060 A1 | 6/2013 |
| WO | 2014196793 A1 | 12/2014 |
| WO | 2015150097 A1 | 10/2015 |

OTHER PUBLICATIONS

European Patent Office; Communication dated May 4, 2018 in counterpart European Application No. 15865425.1.
Roland W. Bürli, et al., "DNA binding ligands targets drug-resistant Gram-positive bacteria. Part 1: Internal benzimidazole derivatives", Bioorganic & Medicinal Letters, 2004, pp. 1253-1257, vol. 14, No. 5.
Santosh A. Khedkar, et al., CoMFA study of distamycin analogs binding to the minor-groove of DNA: a unified model for broad-spectrum activity, J. Mol Model, 2007, pp. 1099-1108, vol. 13, No. 10.
International Search Report for PCT/KR2015/012926 dated Jun. 29, 2016 [PCT/ISA/210].
Written Opinion for PCT/KR2015/012926 dated Jun. 29, 2016 [PCT/ISA/237].

*Primary Examiner* — Taofiq A Solola
(74) *Attorney, Agent, or Firm* — Sughrue Mion, PLLC

(57) ABSTRACT

A heterocyclic derivative represented by formula (I), or a pharmaceutically acceptable salt or a stereoisomer thereof, which has an inhibitory effect on the activation of STAT3 protein, and is useful for the prevention or treatment of diseases associated with the activation of STAT3 protein.

14 Claims, No Drawings

HETEROCYCLIC DERIVATIVES AND USE THEREOF

CROSS REFERENCE TO RELATED APPLICATIONS

This application is a National Stage of International Application No. PCT/KR2015/012926 filed Nov. 30, 2015, claiming priority based on Korean Patent Application Nos. 10-2014-0170860 filed Dec. 2, 2014 and 10-2015-0128025 filed Sep. 10, 2015, the contents of all of which are incorporated herein by reference in their entirety.

FIELD OF THE INVENTION

The present invention relates to novel heterocyclic compounds, uses thereof for the prevention or treatment of diseases associated with the activation of STAT proteins, particularly, STAT3 protein and pharmaceutical compositions comprising same.

BACKGROUND OF THE INVENTION

Signal transducer and activator of transcription (STAT) proteins are transcription factors which transduce signals from various extracellular cytokines and growth factors to a nucleus. Seven (7) subtypes of STAT proteins (i.e., STAT1, STAT2, STAT3, STAT4, STAT5a, STAT5b and STAT6) are currently known, and generally they consist of about 750-850 amino acids. In addition, each subtype of STAT proteins contains several conserved domains which play an important role in exhibiting the function of STAT proteins. Specifically, five (5) domains from N-terminus to C-terminus of STAT proteins have been reported including coiled-coiled domain, DNA binding domain, linker domain, SH2 domain and transactivation domain (TAD)). Further, X-ray crystalline structures of STAT1, STAT3, STAT4 and STAT5 have been reported since 1998 (Becker S et al., *Nature*, 1998, 394; Vinkemeier U et al., *Science*, 1998, 279; Chen X et al., *Cell*, 1998, 93; D. Neculai et al., *J. Biol. Chem.*, 2005, 280). In general, receptors to which cytokines and growth factors bind are categorized into Class I and Class II. IL-2, IL-3, IL-5, IL-6, IL-12, G-CSF, GM-CSF, LIF, thrombopoietin, etc., bind to Class I receptors, while INF-α, INF-γ, IL-10, etc., bind to Class II receptors (Schindler C et al., *Annu. Rev. Biochem.*, 1995, 64; Novick D et al., *Cell*, 1994, 77; Ho A S et al., *Proc. Natl. Acad. Sci.*, 1993, 90). Among them, the cytokine receptors involved in the activation of STAT proteins can be classified depending on their structural forms of extracellular domains into a gp-130 family, an IL-2 family, a growth factor family, an interferon family and a receptor tyrosine kinase family. Interleukin-6 family cytokines are representative multifunctional cytokines which mediate various physiological activities. When interleukin-6 cytokine binds to IL-6 receptor which is present on the cell membrane surface, it attracts gp-130 receptor to form an IL-6-gp-130 receptor complex. At the same time, JAK kinases (JAK1, JAK2, JAK3 and Tyk2) in the cytoplasm are recruited to a cytoplasmic region of gp130 to be phosphorylated and activated. Subsequently, latent cytoplasmic STAT proteins are attracted to a receptor, phosphorylated by JAK kinases and activated. Tyrosine-705 adjacent to the SH2 domain located in the C-terminus of STAT proteins is phosphorylated, and the activated tyrosine-705 of each STAT protein monomer binds to the SH2 domain of another monomer in a reciprocal manner, thereby forming a homo- or heterodimer. The dimers are translocalized into a nucleus and bind to a specific DNA binding promoter to promote the transcription. Through its transcription process, various proteins (Myc, Cyclin D1/D2, Bcl-xL, Mcl, survivin, VEGF, HIF-1, immune suppressors, etc.) associated with cell proliferation, survival, angiogenesis and immune evasion are produced (Stark et al., *Annu. Rev. Biochem.*, 1997, 67; Levy et al., *Nat. Rev. Mol. Cell Biol.*, 2002, 3).

In particular, STAT3 protein is known to play a crucial role in the acute inflammatory response and the signal transduction pathway of IL-6 and EGF (Akira et al., *Cell*, 1994, 76; Zhong et al., *Science*, 1994, 264). According to the recent clinical report, STAT3 protein is constantly activated in patients with solid cancers occurring in prostate, stomach, breast, lung, pancreas, kidney, uterine, ovary, head and neck, etc., and also in patients with blood cancer such as acute and chronic leukemia, multiple myeloma, etc. Further, it has been reported that the survival rate of a patient group with activated STAT3 is remarkably lower than that of a patient group with inactivated STAT3 (Masuda et al., *Cancer Res.*, 2002, 62; Benekli et al., *Blood*, 2002, 99; Yuichi et al., *Int. J. Oncology*, 2007, 30). Meanwhile, STAT3 was identified to be an essential factor for the growth and maintenance of murine embryonic stem cells in a study employing a STAT3 knockout mouse model. Also, a study with a tissue-specific STAT3-deficient mouse model reveals that STAT3 plays an important role in cell growth, apoptosis, and cell motility in a tissue-specific manner (Akira et al., *Oncogene* 2000, 19). Moreover, since apoptosis induced by anti-sensing STAT3 was observed in various cancer cell lines, STAT3 is considered as a promising new anticancer target. STAT3 is also considered as a potential target in the treatment of patients with diabetes, immune-related diseases, hepatitis C, macular degeneration, human papillomavirus infection, non-Hodgkin's lymphoma, tuberculosis, etc. Meanwhile, newly identified Th17 cells have been reported through a number of recent articles to be associated with various autoimmune diseases (Jacek Tabarkiewicz et al., *Arch. Immunol. Ther. Exp.*, 2015, 11). Based on these reports, a control of the differentiation and function of Th17 cells is considered as a good target in the treatment of related diseases. In particular, since STAT3-dependent IL-6 and IL-23 signal transductions are known as important factors in the differentiation of Th17 cells (Xuexian O. Yang et al., *J. Biol. Chem.*, 2007, 282; Harris T J et al., *J. Immunol.*, 2007, 179), an inhibition of the function of STAT3 is expected to be effective in the treatment of diseases associated with Th17 cells such as systemic lupus erythematosus, uveitis, rheumatoid arthritis, autoimmune thyroid disease, inflammatory bowel disease, psoriasis and psoriatic arthritis (Jacek Tabarkiewicz et al., *Arch. Immunol. Ther. Exp.*, 2015, 11).

Recently, IL-6 and IL-23 antibodies are under clinical studies on the treatment of arthritis and psoriasis associated with Th17 cells and exhibit a clinical efficacy (Nishimoto N. et al., *Arthritis Rheum.*, 2004, 50; Gerald G. et al., N. Engl. J. Med., 2007, 356). This also confirms that the inhibition of STAT3 signal transduction is an effective therapeutic method for such diseases.

In contrast, while having intracellular response pathways of identical cytokines and growth factors to those of STAT3, STAT1 increases inflammation and congenital and acquired immunities to inhibit the proliferation of cancer cells or cause pro-apoptotic responses, unlike STAT3 (Valeria Poli et al., *Review, Landes Bioscience*, 2009).

In order to develop STAT3 inhibitors, the following methods can be considered: i) inhibition of the phosphorylation of STAT3 protein by IL-6/gp-130/JAK kinase, ii) inhibition of the dimerization of activated STAT3 proteins, and iii) inhibition of the binding of STAT3 dimer to nuclear DNA. Small molecular STAT3 inhibitors are currently under development. Specifically, OPB-31121 and OPB-51602 are under clinical studies on patients with solid cancers or blood cancers by Otsuka Pharmaceutical Co., Ltd. Further, S3I-201 (Siddiquee et al., *Proc. Natl. Acad. Sci.,* 2007, 104), S3I-M2001 (Siddiquee et al., *Chem. Biol.,* 2007, 2), LLL-12 (Lin et al., *Neoplasia,* 2010, 12), Stattic (Schust et al., *Chem. Biol.* 2006, 13), STA-21 (Song et al., *Proc. Natl. Acad. Sci.,* 2005, 102), SF-1-066 (Zhang et al., *Biochem. Pharm.,* 2010, 79) and STX-0119 (Matsuno et al., *ACS Med. Chem. Lett.,* 2010, 1), etc. have been reported to be effective in a cancer cell growth inhibition experiment and in animal model (in vivo Xenograft model). Furthermore, although peptide compounds mimicking the sequence of amino acid of pY-705 (STAT3) adjacent to the binding site to SH2 domain or the amino acid sequence of gp-130 receptor in which JAK kinases bind were studied (Coleman et al., *J. Med. Chem.,* 2005, 48), the development of the peptide compounds has not been successful due to the problems such as solubility and membrane permeability.

SUMMARY OF THE INVENTION

Accordingly, it is an object of the present invention to provide novel heterocyclic derivatives for the inhibition of the activation of STAT3 protein.

It is another object of the present invention to provide uses of the heterocyclic derivatives for the prevention or treatment of diseases associated with the activation of STAT3 protein.

In accordance with one aspect of the present invention, there is provided a compound selected from the group consisting of a heterocyclic derivative represented by formula (I), and a pharmaceutically acceptable salt and a stereoisomer thereof:

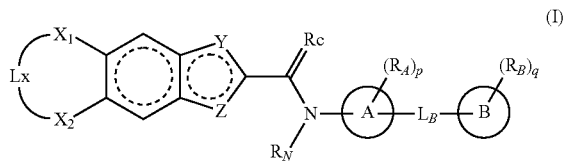

wherein $X_1$ and $X_2$ are each independently —C(-Rx)(-Rx")-, —C(-Rx')(-Rx")-, —C(-Rx")(-Rx")-, —C(=O)—, —N(Rx)-, —N(-Rx')-, —N(-Rx")-, or —O—;

Rx is

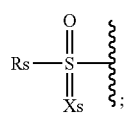

Xs is =O or =NH;

Rs is $C_{1-6}$alkyl, halo$C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, or amino$C_{1-6}$alkyl;

Rx' is halo$C_{1-6}$alkyl, $C_{1-4}$alkoxycarbonyl, cyano, nitro, azido, amino, or a 3- to 6-membered heterocyclyl unsubstituted or substituted with Rx";

Rx" is each independently hydrogen, halogen, nitro, amino, $C_{1-6}$alkyl, $C_{1-6}$alkoxy, halo$C_{1-6}$alkoxy, carbamoyl$C_{1-6}$ alkyl, $C_{1-6}$alkylamino-$C_{1-6}$alkyl, or di$C_{1-6}$alkylamino-$C_{1-6}$alkyl;

one of Y and Z is —S— or —NH—, and the other is —CH= or —N=;

Lx is a saturated or unsaturated $C_{1-4}$ hydrocarbon chain not containing or containing 1 to 3 heterogroups selected from the group consisting of —O—, —NH—, —N=, —S—, —S(=O)— and —S(=O)$_2$— in the chain, and unsubstituted or substituted with at least one Rx" moiety;

A and B are each independently a monocyclic- or bicyclic-saturated or unsaturated $C_{3-10}$carbocycle or 5- to 12-membered heterocycle;

Rc is =O, =NH, =N(—$C_{1-6}$alkyl), or =N(—OH);

$R_N$ is hydrogen or $C_{1-6}$alkyl;

$L_B$ is —[C(—$R_L$)(—$R_L$')]$_m$—, —[C(—$R_L$)(—$R_L$')]$_n$—O—, —O—, —NH—, —N($C_{1-6}$alkyl)-, —S(=O)$_2$—, —C(=O)—, or —C(=CH$_2$)—, wherein m is an integer of 0 to 3, n is an integer of 1 to 3, $R_L$ and $R_L$' are each independently hydrogen, hydroxy, halogen or $C_{1-6}$alkyl, or $R_L$ and $R_L$' are linked together to form $C_{1-6}$alkylene;

$R_A$ is hydrogen, halogen, cyano, $C_{1-6}$alkyl, halo$C_{1-6}$alkyl, cyano$C_{1-6}$alkyl, $C_{1-6}$alkylcarbonyl, $C_{1-6}$alkoxy, halo$C_{1-6}$alkoxy, cyano$C_{1-6}$alkoxy, $C_{1-6}$alkylamino, di$C_{1-6}$alkylamino, $C_{1-6}$alkylthio, $C_{1-6}$alkylaminocarbonyl, di$C_{1-6}$alkylaminocarbonyl, $C_{2-8}$alkynyl, $C_{1-6}$alkoxycarbonylamino-$C_{1-6}$ alkoxy, amino$C_{1-6}$alkoxy, or 3- to 6-membered heterocyclyl;

$R_B$ is hydrogen, halogen, hydroxy, cyano, nitro, amino, oxo, aminosulfonyl, sulfonylamido, $C_{1-6}$alkylamino, $C_{1-6}$alkyl, halo$C_{1-6}$alkyl, cyano$C_{1-6}$alkyl, $C_{1-6}$alkoxy, halo$C_{1-6}$alkoxy, cyano$C_{1-6}$alkoxy, $C_{3-8}$cycloalkyloxy, $C_{2-8}$alkenyl, $C_{2-8}$alkenyloxy, $C_{2-8}$alkynyl, $C_{2-8}$alkynyloxy, $C_{1-6}$alkylamino-$C_{1-6}$alkoxy, di$C_{1-6}$alkylamino-$C_{1-6}$alkoxy, $C_{1-6}$alkoxy-carbonyl, carbamoyl, carbamoyl-$C_{1-6}$alkoxy, $C_{1-6}$alkylthio, $C_{1-6}$alkylsulfinyl, $C_{1-6}$alkylsulfonyl, 5- to 10-membered heterocyclyl, 5- to 10-membered heterocyclyl-$C_{1-6}$alkyl, 5- to 10-membered heterocyclyl-$C_{1-6}$alkoxy, or 5- to 10-membered heterocyclyl-oxy;

p is an integer of 0 to 4, and, when p is 2 or higher, $R_A$ moieties are the same as or different from each other;

q is an integer of 0 to 4, and, when q is 2 or higher, $R_B$ moieties are the same as or different from each other; and each of said heterocycle and heterocyclyl moieties independently contains at least one heterogroup selected from the group consisting of —O—, —NH—, —N=, —S—, —S(=O)— and —S(=O)$_2$—.

In accordance with another aspect of the present invention, there is provided a use of a compound selected from the group consisting of a heterocyclic derivative represented by formula (I) above, and a pharmaceutically acceptable salt and a stereoisomer thereof for the manufacture of a medicament for preventing or treating diseases associated with the activation of STAT3 protein.

In accordance with a further aspect of the present invention, there is provided a pharmaceutical composition for preventing or treating diseases associated with the activation of STAT3 protein, comprising a compound selected from the group consisting of a heterocyclic derivative represented by formula (I) above, and a pharmaceutically acceptable salt and a stereoisomer thereof as active ingredients.

In accordance with a still further aspect of the present invention, there is provided a method for preventing or treating diseases associated with the activation of STAT3 protein in a mammal, which comprises administering a compound selected from the group consisting of a heterocyclic derivative represented by formula (I) above, and a pharmaceutically acceptable salt and a stereoisomer thereof to the mammal.

The heterocyclic derivative represented by formula (I) above, or a pharmaceutically acceptable salt or a stereoisomer thereof has an excellent inhibitory effect on the activation of STAT3 protein, and thus it can be used for the prevention or treatment of diseases associated with the activation of STAT3 protein.

DETAILED DESCRIPTION OF THE INVENTION

The present invention will be further described in detail herein below.

In the specification of the present invention, the term "halogen" refers to fluoro, chloro, bromo or iodo, unless specified otherwise.

The term "alkyl" refers to a linear or branched hydrocarbon moiety, unless specified otherwise.

The terms "haloalkyl", "haloalkoxy", "halophenyl", etc., respectively refer to alkyl, alkoxy, and phenyl substituted with at least one halogen.

The term "carbocycle" refers to an aromatic or non-aromatic hydrocarbon ring, which may be saturated or unsaturated, and a monocyclic or polycyclic radical. The term "carbocyclyl" refers to a radical of "carbocycle", and is used as a term inclusive of "cycloalkyl" and "aryl". The term "cycloalkyl" refers to a saturated hydrocarbon radical, which may be monocyclic or polycyclic. The term "aryl" refers to an aromatic hydrocarbon ring, which may be monocyclic or polycyclic.

The terms "carbocycle", "carbocyclyl", "cycloalkyl" and "aryl" may refer to, for example, a monocycle or polycycle having 3 to 20 carbon atoms, and will be indicated as "$C_{3-20}$ carbocycle", "$C_{3-20}$ carbocyclyl", "$C_{3-20}$ cycloalkyl", and "$C_{3-20}$ aryl", respectively.

The term "heterocycle" refers to an aromatic or non-aromatic ring having at least one heteroatom, which may be saturated or unsaturated, and a monocycle or polycycle. The term "heterocyclyl" refers to a radical of "heterocycle", which is used as a term inclusive of "heterocycloalkyl" and "heteroaryl". The term "heterocycloalkyl" refers to a saturated ring radical having at least one heteroatom, which may be monocyclic or polycyclic. The term "heteroaryl" refers to an aromatic ring radical having at least one heteroatom, which may be monocyclic or polycyclic.

The term "heteroatom" may be selected from N, O and S.

The terms "heterocycle", "heterocyclyl", "heterocycloalkyl" and "heteroaryl" may refer to, for example, a mono- or polycycle having 3 to 20 heteroatoms and/or carbon atoms, and will be indicated as "3- to 20-membered heterocycle", "3- to 20-membered heterocyclyl", "3- to 20-membered heterocycloalkyl", and "3- to 20-membered heteroaryl".

The terms "chain" refers to a saturated or unsaturated $C_{2-10}$ hydrocarbon chain not containing any heteroatoms in the chain, for example, ethylene, propylene, butylene and —$CH_2$—CH═CH—; or a saturated or unsaturated $C_{2-10}$ hydrocarbon chain containing at least one heterogroup selected from the group consisting of —O—, —NH—, —N═, —S—, —S(═O)— and —S(═O)$_2$— in the chain, for example, —$CH_2$—O—$CH_2$—, —$CH_2$—O—$CH_2$—O—$CH_2$—, —$CH_2$—CH═CH—NH— and —$CH_2$—$CH_2$—S(═O)$_2$—$CH_2$—O—, unless specified otherwise. The chain may be substituted with at least one selected from the group consisting of halogen, $C_{1-6}$alkyl and $C_{1-6}$alkoxy.

In accordance with one aspect of the present invention, there is provided a compound selected from the group consisting of a heterocyclic derivative represented by formula (I), and a pharmaceutically acceptable salt and a stereoisomer thereof:

(I)

[Chemical structure of formula (I)]

wherein
$X_1$ and $X_2$ are each independently —C(-Rx)(-Rx")—, —C(-Rx')(-Rx")—, —C(-Rx")(-Rx")—, —C(═O)—, —N(Rx)-, —N(-Rx')-, —N(-Rx")-, or —O—;
Rx is

[Chemical structure: Rs—S(═O)(═Xs)—]

Xs is ═O or ═NH;
Rs is $C_{1-6}$alkyl, halo$C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, or amino$C_{1-6}$alkyl;
Rx' is halo$C_{1-6}$alkyl, $C_{1-4}$alkoxycarbonyl, cyano, nitro, azido, amino, or a 3- to 6-membered heterocyclyl unsubstituted or substituted with Rx";
Rx" is each independently hydrogen, halogen, nitro, amino, $C_{1-6}$alkyl, $C_{1-6}$alkoxy, halo$C_{1-6}$alkoxy, carbamoyl$C_{1-6}$ alkyl, $C_{1-6}$alkylamino-$C_{1-6}$alkyl, or di$C_{1-6}$alkylamino-$C_{1-6}$alkyl;
one of Y and Z is —S— or —NH—, and the other is —CH═ or —N═;
Lx is a saturated or unsaturated $C_{1-4}$ hydrocarbon chain not containing or containing 1 to 3 heterogroups selected from the group consisting of —O—, —NH—, —N═, —S—, —S(═O)— and —S(═O)$_2$— in the chain, and unsubstituted or substituted with at least one Rx" moiety;
A and B are each independently a monocyclic- or bicyclic-saturated or unsaturated $C_{3-10}$carbocycle or 5- to 12-membered heterocycle;
Rc is ═O, ═NH, ═N(—$C_{1-6}$alkyl), or ═N(—OH);
$R_N$ is hydrogen or $C_{1-6}$alkyl;
$L_B$ is —[C(—$R_L$)(—$R_L$')]$_m$—, —[C(—$R_L$)(—$R_L$')]$_n$—O—, —O—, —NH—, —N($C_{1-6}$alkyl)-, —S(═O)$_2$—, —C(═O)—, or —C(═$CH_2$)—, wherein m is an integer of 0 to 3, n is an integer of 1 to 3, $R_L$ and $R_L$' are each independently hydrogen, hydroxy, halogen or $C_{1-6}$alkyl, or $R_L$ and $R_L$' are linked together to form $C_{1-6}$alkylene;
$R_A$ is hydrogen, halogen, cyano, $C_{1-6}$alkyl, halo$C_{1-6}$alkyl, cyano$C_{1-6}$alkyl, $C_{1-6}$alkylcarbonyl, $C_{1-6}$alkoxy, halo$C_{1-6}$ alkoxy, cyano$C_{1-6}$alkoxy, $C_{1-6}$alkylamino, di$C_{1-6}$alkylamino, $C_{1-6}$alkylthio, $C_{1-6}$alkylaminocarbonyl, di$C_{1-6}$alkylaminocarbonyl, $C_{2-8}$alkynyl, $C_{1-6}$alkoxycarbonylamino-$C_{1-6}$ alkoxy, amino$C_{1-6}$alkoxy, or 3- to 6-membered heterocyclyl;
$R_B$ is hydrogen, halogen, hydroxy, cyano, nitro, amino, oxo, aminosulfonyl, sulfonylamido, $C_{1-6}$alkylamino, $C_{1-6}$alkyl, halo$C_{1-6}$alkyl, cyano$C_{1-6}$alkyl, $C_{1-6}$alkoxy, haloC$_{1-6}$alkoxy, cyanoC$_{1-6}$alkoxy, C$_{3-8}$cycloalkyloxy, C$_{2-8}$alkenyl, C$_{2-8}$alkenyloxy, C$_{2-8}$alkynyl, C$_{2-8}$alkynyloxy, C$_{1-6}$alkylamino-C$_{1-6}$alkoxy, diC$_{1-6}$alkylamino-C$_{1-6}$alkoxy, C$_{1-6}$alkoxy-carbonyl, carbamoyl, carbamoyl-C$_{1-6}$alkoxy, C$_{1-6}$alkylthio, C$_{1-6}$alkylsulfinyl, C$_{1-6}$alkylsulfonyl, 5- to 10-membered heterocyclyl, 5- to 10-membered heterocyclyl-C$_{1-6}$alkyl, 5- to 10-membered heterocyclyl-C$_{1-6}$alkoxy, or 5- to 10-membered heterocyclyl-oxy;

p is an integer of 0 to 4, and, when p is 2 or higher, R$_A$ moieties are the same as or different from each other;

q is an integer of 0 to 4, and, when q is 2 or higher, R$_B$ moieties are the same as or different from each other; and each of said heterocycle and heterocyclyl moieties independently contains at least one heterogroup selected from the group consisting of —O—, —NH—, —N═, —S—, —S(═O)— and —S(═O)$_2$—.

In a preferred embodiment of the compound of formula (I), one of Y and Z is —S— or —NH—, and the other is —CH═;

Lx is a saturated C$_{1-3}$ hydrocarbon chain not containing or containing at least one heteroatom selected from the group consisting of O, N and S in the chain, and unsubstituted or substituted with at least one substituent selected from the group consisting of halogen, C$_{1-6}$alkyl and C$_{1-6}$alkoxy;

one of X$_1$ and X$_2$ is —C(-Rx)(-Rx")-, —C(-Rx')(-Rx")-, —C(═O)—, —N(Rx)- or —N(-Rx')-, and the other is —C(-Rx")(-Rx")-, —N(-Rx")- or —O—;

Rx is

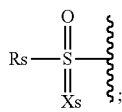

Xs is ═O or ═NH;
Rs is C$_{1-6}$alkyl or haloC$_{1-6}$alkyl;
Rx' is haloC$_{1-6}$alkyl, cyano, nitro, amino, azido, or a 5- to 6-membered heterocyclyl containing at least one heteroatom selected from the group consisting of N, S and O and unsubstituted or substituted with oxo;
Rx" is hydrogen, halogen, C$_{1-6}$alkyl, or C$_{1-4}$alkoxycarbonyl; and
Rc, R$_N$, A, B, L$_B$, R$_A$, R$_B$, p and q are the same as defined above in formula (I).

In a preferred embodiment of the compound of formula (I),
Y is —CH═;
Z is —S—;
Rc is ═O;
R$_N$ is hydrogen;
Lx is a saturated C$_{1-3}$ hydrocarbon chain not containing or containing oxygen atom in the chain, and unsubstituted or substituted with at least one substituent selected from the group consisting of halogen, C$_{1-6}$alkyl and C$_{1-6}$alkoxy;
X$_1$ is —C(-Rx)(-Rx")-, —C(-Rx')(-Rx")-, or —N(Rx)-;
X$_2$ is —C(-Rx")(-Rx")-, —C(═O)—, —N(-Rx")-, or —O—;
Rx is

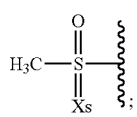

Xs is ═O or ═NH;
Rx' is haloC$_{1-6}$alkyl, cyano, nitro, amino, azido, or a 5- to 6-membered heterocyclyl containing 1 to 2 heteroatoms selected from N and O and unsubstituted or substituted with oxo;
Rx" is hydrogen, halogen, C$_{1-6}$alkyl, or C$_{1-4}$alkoxycarbonyl; and
A, B, L$_B$, R$_A$, R$_B$, p and q are the same as defined above in formula (I).

In a preferred embodiment of the compound of formula (I),
Y is —CH═;
Z is —S—;
Rc is ═O;
R$_N$ is hydrogen;
Lx is a saturated C$_{1-3}$ hydrocarbon chain not containing or containing oxygen atom in the chain, and unsubstituted or substituted with at least one substituent selected from the group consisting of halogen, C$_{1-6}$alkyl and C$_{1-6}$alkoxy;
X$_1$ is —C(-Rx)(-Rx")-, —C(-Rx')(-Rx")-, or —N(Rx)-;
X$_2$ is —C(-Rx")(-Rx")-, —C(═O)—, —N(-Rx")-, or —O—;
Rx is

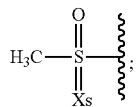

Xs is ═O or ═NH;
Rx' is haloC$_{1-6}$alkyl, cyano, nitro, amino, azido, or a 5- to 6-membered heterocyclyl containing 1 to 2 heteroatoms selected from N and O and unsubstituted or substituted with oxo;
Rx" is hydrogen, halogen, C$_{1-6}$alkyl, or C$_{1-4}$alkoxycarbonyl;
A is benzene or a 5- to 10-membered heteroaryl containing 1 to 3 nitrogen atoms;
B is a monocyclic- or bicyclic-saturated or unsaturated C$_{6-10}$carbocycle or 5- to 10-membered heterocycle;
L$_B$ is —[C(—R$_L$)(—R$_L$')]$_m$—, —O—, —NH— or —N(C$_{1-6}$alkyl)-, wherein m is 0 or 1, R$_L$ and R$_L$' are each independently hydrogen, hydroxy, halogen or C$_{1-6}$alkyl, or R$_L$ and R$_L$' are linked together to form C$_{2-5}$alkylene;
R$_A$ is halogen, C$_{1-6}$alkoxycarbonylamino-C$_{1-6}$alkoxy, aminoC$_{1-6}$alkoxy, or 3- to 6-membered heterocyclyl;
R$_B$ is halogen, C$_{1-6}$alkyl, C$_{1-6}$alkoxy, haloC$_{1-6}$alkyloxy, C$_{2-6}$alkenyloxy, C$_{3-10}$carbocyclyl-oxy, or 3- to 10-membered heterocyclyl-C$_{1-3}$alkoxy; and
each of said heteroaryl, heterocycle and heterocyclyl moieties independently contains 1 to 3 heteroatoms selected from the group consisting of O, N and S.

In a preferred embodiment of the compound of formula (I),
X$_1$ is —N(-Rx)-;
X$_2$ is —C(-Rx")(-Rx")- or —N(-Rx")-;
Y is —CH═;
Z is —S—;
Rc is ═O;
R$_N$ is hydrogen;
Lx is ethylene substituted with one or two Rx" moieties, Rx is

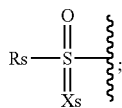

Xs is =O;
Rs is methyl;
Rx" is the same as defined above in formula (I); and
A, B, $L_B$, $R_A$, $R_B$, p and q are the same as defined above in formula (I).

In a preferred embodiment of the compound of formula (I),
$X_1$ is —CH(-Rx)-;
$X_2$ is —N(-Rx")-;
Y is —CH=;
Z is —S—;
Rc is =O;
$R_N$ is hydrogen;
Lx is ethylene;
Rx is

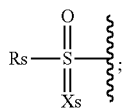

Xs is =O;
Rs is methyl;
Rx" is the same as defined above in formula (I); and
A, B, $L_B$, $R_A$, $R_B$, p and q are the same as defined above in formula (I).

In a preferred embodiment of the compound of formula (I),
$X_1$ is —C(-Rx)(-Rx")-;
$X_2$ is —O—;
Y is —CH=;
Z is —S—;
Rc is =O;
$R_N$ is hydrogen;
Lx is ethylene;
Rx is

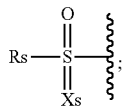

Xs is =O;
Rs is methyl;
Rx" is the same as defined above in formula (I); and
A, B, $L_B$, $R_A$, $R_B$, p and q are the same as defined above in formula (I).

In a preferred embodiment of the compound of formula (I),
$X_1$ is —C(-Rx')(-Rx")-;
$X_2$ is —O—;
Y is —CH=;
Z is —S—;
Rc is =O;
$R_N$ is hydrogen;
Lx is ethylene;

Rx' and Rx" are the same defined above in formula (I); and
A, B, $L_B$, $R_A$, $R_B$, p and q are the same as defined above in formula (I).

In a preferred embodiment of the compound of formula (I),
$X_1$ is —CH(-Rx)-;
$X_2$ is —C(-Rx")(-Rx")- or —C(=O)—;
Y is —CH=;
Z is —S—;
Rc is =O;
$R_N$ is hydrogen;
Lx is ethylene;
Rx is

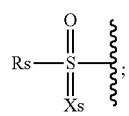

Xs is =O;
Rs is methyl;
Rx" is the same as defined above in formula (I); and
A, B, $L_B$, $R_A$, $R_B$, p and q are the same as defined above in formula (I).

In a preferred embodiment of the compound of formula (I),
$X_1$ is —CH(-Rx)-;
$X_2$ is —C(-Rx")(-Rx")-;
Y is —CH=;
Z is —S—;
Rc is =O;
$R_N$ is hydrogen;
Lx is —CH$_2$—O—;
Rx is

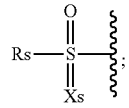

Xs is =O;
Rs is methyl;
Rx" is the same as defined above in formula (I); and
A, B, $L_B$, $R_A$, $R_B$, p and q are the same as defined above in formula (I).

In a preferred embodiment of the compound of formula (I),
$X_1$ is —C(-Rx)(-Rx")- or —N(Rx)-;
$X_2$ is —O—;
Y is —NH—;
Z is —CH=;
Rc is =O;
$R_N$ is hydrogen;
Lx is propylene;
Rx and Rx" are the same as defined above in formula (I); and
A, B, $L_B$, $R_A$, $R_B$, p and q are the same as defined above in formula (I).

Preferable examples of the compound according to the present invention are listed below, and a pharmaceutically acceptable salt and a stereoisomer thereof are also included in the scope of the present invention:

1) N-(2-chloro-6-(4-chlorophenoxy)pyridin-4-yl)-1-(methylsulfonyl)-2,3-dihydro-1H-thieno[3',2':4,5]benzo[1,2-b][1,4]oxazine-7-carboxamide;
2) N-(2-chloro-6-(4-chlorophenoxy)pyridin-4-yl)-3,3-dimethyl-1-(methylsulfonyl)-2,3-dihydro-1H-thieno[3',2':4,5]benzo[1,2-b][1,4]oxazine-7-carboxamide;
3) N-(2-chloro-6-(4-chlorophenoxy)pyridin-4-yl)-1-(methylsulfonyl)-1,2,3,4-tetrahydrothieno[3',2':4,5]benzo[1,2-b][1,4]oxazepine-8-carboxamide;
4) N-(2-chloro-6-(4-chlorophenoxy)pyridin-4-yl)-8,8-dimethyl-5-(methylsulfonyl)-5,6,7,8-tetrahydrothieno[2,3-g]quinoline-2-carboxamide;
5) tert-butyl 7-((2-chloro-6-(4-chlorophenoxy)pyridin-4-yl)carbamoyl)-1-(methylsulfonyl)-2,3-dihydrothieno[2,3-g]quinoxaline-4(1H)-carboxylate;
6) N-(2-chloro-6-(4-chlorophenoxy)pyridin-4-yl)-5-(methylsulfonyl)-5,6,7,8-tetrahydrothieno[2,3-g]quinoline-2-carboxamide;
7) N-(2-chloro-6-(4-chlorophenoxy)pyridin-4-yl)-4-methyl-1-(methylsulfonyl)-1,2,3,4-tetrahydrothieno[2,3-g]quinoxaline-7-carboxamide;
8) N-(2-chloro-6-(4-chlorophenoxy)pyridin-4-yl)-4-(methylsulfonyl)-3,4-dihydro-2H-thieno[3,2-g]chromene-7-carboxamide;
9) N-(2-chloro-6-(4-chlorophenoxy)pyridin-4-yl)-5-(methylsulfonyl)-2,3,4,5-tetrahydrothieno[3',2':4,5]benzo[1,2-b]oxepine-8-carboxamide;
10) N-(2-chloro-6-(4-chlorophenoxy)pyridin-4-yl)-5-(methylsulfonyl)-5,6,7,8-tetrahydronaphtho[2,3-b]thiophene-2-carboxamide;
11) N-(2-chloro-6-(4-chlorophenoxy)pyridin-4-yl)-4-methyl-4-(methylsulfonyl)-3,4-dihydro-2H-thieno[3,2-g]chromene-7-carboxamide;
12) N-(2-chloro-6-(4-chlorophenoxy)pyridin-4-yl)-5-(methylsulfonyl)-5,8-dihydro-6H-thieno[3,2-g]isochromene-2-carboxamide;
13) N-(2-chloro-6-(4-chlorophenoxy)pyridin-4-yl)-4-fluoro-4-(methylsulfonyl)-3,4-dihydro-2H-thieno[3,2-g]chromene-7-carboxamide;
14) N-(2-chloro-6-(4-chlorophenoxy)pyridin-4-yl)-8,8-difluoro-5-(methylsulfonyl)-5,6,7,8-tetrahydronaphtho[2,3-b]thiophene-2-carboxamide;
15) N-(2-chloro-6-(p-tolyloxy)pyridin-4-yl)-4-(methylsulfonyl)-3,4-dihydro-2H-thieno[3,2-g]chromene-7-carboxamide;
16) N-(2-chloro-6-(3-(trifluoromethyl)phenoxy)pyridin-4-yl)-4-(methylsulfonyl)-3,4-dihydro-2H-thieno[3,2-g]chromene-7-carboxamide;
17) N-(2-chloro-6-(4-(trifluoromethyl)phenoxy)pyridin-4-yl)-4-(methylsulfonyl)-3,4-dihydro-2H-thieno[3,2-g]chromene-7-carboxamide;
18) N-(2-chloro-6-(3,5-dichlorophenoxy)pyridin-4-yl)-4-(methylsulfonyl)-3,4-dihydro-2H-thieno[3,2-g]chromene-7-carboxamide;
19) N-(2-chloro-6-(4-chloro-3-fluorophenoxy)pyridin-4-yl)-4-(methylsulfonyl)-3,4-dihydro-2H-thieno[3,2-g]chromene-7-carboxamide;
20) N-(2-chloro-6-(4-chloro-3-methylphenoxy)pyridin-4-yl)-4-(methylsulfonyl)-3,4-dihydro-2H-thieno[3,2-g]chromene-7-carboxamide;
21) N-(2-chloro-6-(4-chloro-2-methylphenoxy)pyridin-4-yl)-4-(methylsulfonyl)-3,4-dihydro-2H-thieno[3,2-g]chromene-7-carboxamide;
22) N-(2-chloro-6-(4-methoxyphenoxy)pyridin-4-yl)-4-(methylsulfonyl)-3,4-dihydro-2H-thieno[3,2-g]chromene-7-carboxamide;
23) N-(2-chloro-6-(4-chloro-2-fluorophenoxy)pyridin-4-yl)-4-(methylsulfonyl)-3,4-dihydro-2H-thieno[3,2-g]chromene-7-carboxamide;
24) N-(2-chloro-6-(3,4-dichlorophenoxy)pyridin-4-yl)-4-(methylsulfonyl)-3,4-dihydro-2H-thieno[3,2-g]chromene-7-carboxamide;
25) N-(2-chloro-6-(3-chlorophenoxy)pyridin-4-yl)-4-(methylsulfonyl)-3,4-dihydro-2H-thieno[3,2-g]chromene-7-carboxamide;
26) N-(2-chloro-6-(4-fluorophenoxy)pyridin-4-yl)-4-(methylsulfonyl)-3,4-dihydro-2H-thieno[3,2-g]chromene-7-carboxamide;
27) N-(2-chloro-6-(3-chloro-4-fluorophenoxy)pyridin-4-yl)-4-(methylsulfonyl)-3,4-dihydro-2H-thieno[3,2-g]chromene-7-carboxamide;
28) N-(2-chloro-6-(4-(trifluoromethoxy)phenoxy)pyridin-4-yl)-4-(methylsulfonyl)-3,4-dihydro-2H-thieno[3,2-g]chromene-7-carboxamide;
29) N-(2-chloro-6-(3-(trifluoromethoxy)phenoxy)pyridin-4-yl)-4-(methylsulfonyl)-3,4-dihydro-2H-thieno[3,2-g]chromene-7-carboxamide;
30) N-(2-chloro-6-(3-chloro-5-methoxyphenoxy)pyridin-4-yl)-4-(methylsulfonyl)-3,4-dihydro-2H-thieno[3,2-g]chromene-7-carboxamide;
31) N-(2-chloro-6-(3-chloro-5-fluorophenoxy)pyridin-4-yl)-4-(methylsulfonyl)-3,4-dihydro-2H-thieno[3,2-g]chromene-7-carboxamide;
32) N-(2-chloro-6-(3-fluoro-5-methoxyphenoxy)pyridin-4-yl)-4-(methylsulfonyl)-3,4-dihydro-2H-thieno[3,2-g]chromene-7-carboxamide;
33) N-(2-chloro-6-(m-tolyloxy)pyridin-4-yl)-4-(methylsulfonyl)-3,4-dihydro-2H-thieno[3,2-g]chromene-7-carboxamide;
34) N-(2-chloro-6-(3,4-difluorophenoxy)pyridin-4-yl)-4-(methylsulfonyl)-3,4-dihydro-2H-thieno[3,2-g]chromene-7-carboxamide;
35) N-(2-chloro-6-(5-chloro-2-fluorophenoxy)pyridin-4-yl)-4-(methylsulfonyl)-3,4-dihydro-2H-thieno[3,2-g]chromene-7-carboxamide;
36) N-(2-chloro-6-(3-chloro-2-fluorophenoxy)pyridin-4-yl)-4-(methylsulfonyl)-3,4-dihydro-2H-thieno[3,2-g]chromene-7-carboxamide;
37) N-(2-chloro-6-(5-chloro-2-methylphenoxy)pyridin-4-yl)-4-(methylsulfonyl)-3,4-dihydro-2H-thieno[3,2-g]chromene-7-carboxamide;
38) N-(2-chloro-6-(3-chloro-4-methylphenoxy)pyridin-4-yl)-4-(methylsulfonyl)-3,4-dihydro-2H-thieno[3,2-g]chromene-7-carboxamide;
39) N-(2-chloro-6-(2-(trifluoromethyl)phenoxy)pyridin-4-yl)-4-(methylsulfonyl)-3,4-dihydro-2H-thieno[3,2-g]chromene-7-carboxamide;
40) N-(2-chloro-6-(2-(trifluoromethoxy)phenoxy)pyridin-4-yl)-4-(methylsulfonyl)-3,4-dihydro-2H-thieno[3,2-g]chromene-7-carboxamide;
41) N-(2-chloro-6-(2-fluoro-3-methylphenoxy)pyridin-4-yl)-4-(methylsulfonyl)-3,4-dihydro-2H-thieno[3,2-g]chromene-7-carboxamide;
42) N-(2-chloro-6-(4-chloro-2-methoxyphenoxy)pyridin-4-yl)-4-(methylsulfonyl)-3,4-dihydro-2H-thieno[3,2-g]chromene-7-carboxamide;
43) (S)—N-(2-chloro-6-(4-chlorophenoxy)pyridin-4-yl)-4-(methylsulfonyl)-3,4-dihydro-2H-thieno[3,2-g]chromene-7-carboxamide;
44) (R)—N-(2-chloro-6-(4-chlorophenoxy)pyridin-4-yl)-4-(methylsulfonyl)-3,4-dihydro-2H-thieno[3,2-g]chromene-7-carboxamide;

45) (S)—N-(2-chloro-6-(4-chlorophenoxy)pyridin-4-yl)-4-fluoro-4-(methylsulfonyl)-3,4-dihydro-2H-thieno[3,2-g]chromene-7-carboxamide;
46) (R)—N-(2-chloro-6-(4-chlorophenoxy)pyridin-4-yl)-4-fluoro-4-(methylsulfonyl)-3,4-dihydro-2H-thieno[3,2-g]chromene-7-carboxamide;
47) (S)—N-(2-chloro-6-(4-chlorophenoxy)pyridin-4-yl)-4-methyl-4-(methylsulfonyl)-3,4-dihydro-2H-thieno[3,2-g]chromene-7-carboxamide;
48) (R)—N-(2-chloro-6-(4-chlorophenoxy)pyridin-4-yl)-4-methyl-4-(methylsulfonyl)-3,4-dihydro-2H-thieno[3,2-g]chromene-7-carboxamide;
49) (S)—N-(2-chloro-6-(3-chloro-5-methoxyphenoxy)pyridin-4-yl)-4-(methylsulfonyl)-3,4-dihydro-2H-thieno[3,2-g]chromene-7-carboxamide;
50) N-(2-chloro-6-(4-chlorophenoxy)pyridin-4-yl)-1-(methylsulfonyl)-1,2,3,4-tetrahydrothieno[2,3-g]quinoxaline-7-carboxamide;
51) N-(2-chloro-6-(4-chlorophenoxy)pyridin-4-yl)-5-(methylsulfonyl)-8-oxo-5,6,7,8-tetrahydronaphtho[2,3-b]thiophene-2-carboxamide;
52) N-(2-chloro-6-(4-chlorophenoxy)pyridin-4-yl)-4-(1H-pyrazol-1-yl)-3,4-dihydro-2H-thieno[3,2-g]chromene-7-carboxamide;
53) N-(2-chloro-6-(4-chlorophenoxy)pyridin-4-yl)-4-(2-oxopyrrolidin-1-yl)-3,4-dihydro-2H-thieno[3,2-g]chromene-7-carboxamide;
54) N-(2-chloro-6-(4-chlorophenoxy)pyridin-4-yl)-4-cyano-3,4-dihydro-2H-thieno[3,2-g]chromene-7-carboxamide;
55) 4-azido-N-(2-chloro-6-(4-chlorophenoxy)pyridin-4-yl)-3,4-dihydro-2H-thieno[3,2-g]chromene-7-carboxamide; and
56) N-(3-chloro-5-(2-(4-chlorophenyl)propan-2-yl)phenyl)-1-(methylsulfonyl)-2,3-dihydro-1H-thieno[3',2':4,5]benzo[1,2-b][1,4]oxazine-7-carboxamide.

The above-listed names of the compounds are described in accordance with the nomenclature method provided by ChemBioDraw Ultra software (Version 13.0.0.3015) of PerkinElmer.

The present invention provides a pharmaceutically acceptable salt of a heterocyclic derivative represented by formula (I) above. The pharmaceutically acceptable salt should have low toxicity to humans, and should not have any negative impact on the biological activities and physicochemical properties of parent compounds. Examples of the pharmaceutically acceptable salt may include an acid addition salt between a pharmaceutically usable free acid and a basic compound represented by formula (I), an alkaline metal salt (sodium salt, etc.) and an alkaline earth metal salt (potassium salt, etc.), an organic base addition salt between an organic base and carboxylic acid represented by formula (I), amino acid addition salt, etc.

Examples of a suitable form of salts according to the present invention may be a salt with an inorganic acid or organic acid, wherein the inorganic acid may be hydrochloric acid, sulfuric acid, nitric acid, phosphoric acid, perchloric acid, bromic acid, etc., and the organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, etc. The organic base which may be used for the preparation of the organic base addition salt may include tris(hydroxymethyl)methylamine, dicyclohexylamine, etc. Amino acids which may be used for the preparation of amino acid addition base may include natural amino acids such as alanine, and glycine.

The salts may be prepared using a conventional method. For example, the salts may be prepared by dissolving the compound represented by formula (I) in a water-miscible solvent such as methanol, ethanol, acetone, and 1,4-dioxane, adding a free acid or a free base, and then crystallizing the resultant thereafter.

Additionally, the compounds of the present invention may have a chiral carbon center, and thus they may be present in the form of an R or S isomer, a racemic compound, an individual enantiomer or a mixture, an individual diastereomer or a mixture, and all these stereoisomers and a mixture thereof may belong to the scope of the present invention.

Additionally, the compounds of the present invention may also include a hydrate or solvate of the heterocyclic derivative represented by formula (I). The hydrate or solvate may be prepared using a known method, and they are preferred to be non-toxic and water-soluble, and in particular, they are preferably water or a hydrate or solvate having 1-5 molecules of alcoholic solvent (especially ethanol, etc.) bound thereto.

The present invention also provides a use of a compound selected from the group consisting of a heterocyclic derivative represented by formula (I) above, and a pharmaceutically acceptable salt and a stereoisomer thereof for the manufacture of a medicament for preventing or treating diseases associated with the activation of STAT3 protein.

Further, the present invention provides method for preventing or treating diseases associated with the activation of STAT3 protein in a mammal, which comprises administering a compound selected from the group consisting of a heterocyclic derivative represented by formula (I) above, and a pharmaceutically acceptable salt and a stereoisomer thereof to the mammal.

Further, the present invention provides a pharmaceutical composition for preventing or treating diseases associated with the activation of STAT3 protein, comprising a compound selected from the group consisting of a heterocyclic derivative represented by formula (I) above, and a pharmaceutically acceptable salt and a stereoisomer thereof as active ingredients.

Specifically, the diseases associated with the activation of STAT3 protein is selected from the group consisting of solid cancers, hematological or blood cancers, radio- or chemoresistant cancers, metastatic cancers, inflammatory diseases, immunological diseases, diabetes, macular degeneration, human papillomavirus infection and tuberculosis.

More specifically, the diseases associated with the activation of STAT3 protein are selected from the group consisting of breast cancer, lung cancer, stomach cancer, prostate cancer, uterine cancer, ovarian cancer, kidney cancer, pancreatic cancer, liver cancer, colon cancer, skin cancer, head and neck cancer, thyroid cancer, osteosarcoma, acute or chronic leukemia, multiple myeloma, B- or T-cell lymphoma, non-Hodgkin's lymphoma, auto-immune diseases comprising rheumatoid arthritis, psoriasis, hepatitis, inflammatory bowel disease, Crohn's disease, diabetes, macular degeneration, human papillomavirus infection, and tuberculosis.

In particular, a heterocyclic derivative represented by formula (I) above, or a pharmaceutically acceptable salt or a stereoisomer thereof has an excellent inhibitory effect on the activation of STAT3 protein, and thus the present invention also provides a composition for the inhibition of STAT3 protein comprising the same as an active ingredient.

The pharmaceutical composition of the present invention, in addition to the heterocyclic derivative represented by formula (I) above, the pharmaceutically acceptable salt thereof, or the stereoisomer thereof, may further include as active ingredients, common and non-toxic pharmaceutically acceptable additives, for example, a carrier, an excipient, a diluent, an adjuvant, etc., to be formulated into a preparation according to a conventional method.

The pharmaceutical composition of the present invention may be formulated into various forms of preparations for oral administration such as tablets, pills, powders, capsules, syrups, or emulsions, or for parenteral administration such as intramuscular, intravenous or subcutaneous injections, etc., and preferably in the form of a preparation for oral administration.

Examples of the additives to be used in the pharmaceutical composition of the present invention may include sweeteners, binders, solvents, solubilization aids, wetting agents, emulsifiers, isotonic agents, absorbents, disintegrating agents, antioxidants, preservatives, lubricants, fillers, flavoring agents, etc. For example, they may include, lactose, dextrose, sucrose, mannitol, sorbitol, cellulose, glycine, silica, talc, stearic acid, stearin, magnesium stearate, magnesium alluminosilicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, etc.

The pharmaceutical composition of the present invention may be formulated into a preparation for oral administration by adding additives to active ingredients, wherein the additives may include cellulose, calcium silicate, corn starch, lactose, sucrose, dextrose, calcium phosphate, stearic acid, magnesium stearate, calcium stearate, gelatin, talc, surfactants, suspension agents, emulsifiers, diluents, etc.

The pharmaceutical composition of the present invention may be formulated into a preparation for injection by adding additives to the active ingredients, for example, water, a saline solution, a glucose solution, an aqueous glucose solution analog, alcohol, glycol, ether, oil, fatty acid, fatty acid ester, glyceride, surfactants, suspension agents, emulsifiers, etc.

The compound of the present invention may be administered preferably in an amount ranging from 0.1 to 2,000 mg/day based on an adult subject with 70 kg body weight. The compound of the present invention may be administered once daily or a few divided doses. The dosage of the compound of the present invention may vary depending on the health conditions, age, body weight, sex of the subject, administration route, severity of illness, etc., and the scope of the present invention will not be limited to the dose suggested above.

EXAMPLE

Hereinafter, the present invention is described more specifically by the following examples, but these are provided only for illustration purposes and the present invention is not limited thereto.

The definition of the abbreviations used in the following examples is as follows.

TABLE 1

| Abbreviation | Full name |
|---|---|
| $AlCl_3$ | Aluminum chloride |
| ACN | Acetonitrile |
| AcOH | Acetic acid |
| AIBN | 2,2'-Azobis(2-methylpropionitrile) |
| $BH_3$-THF complex | Borane tetrahydrofuran complex |
| BINAP | 2,2'-Bis(diphenylphosphino)-1,1'-binaphthyl |
| $BBr_3$ | Boron tribromide |
| $Boc_2O$ | Di-tert-butyl dicarbonate |
| Brine | Brine is water saturated or nearly saturated with a brine salt (generally, sodium chloride) |
| $CH_3CN$ | Acetonitrile |
| $CDCl_3$ | Deuterated chloroform |
| $CH_2Cl_2$ | Dichloromethane |
| $CH_3I$ | Methyl iodide |
| $CH_3SO_2Cl$ | Methanesulfonyl chloride |
| $(COCl)_2$ | Oxalyl chloride |
| $Cs_2CO_3$ | Cesium carbonate |
| $Cu_2O$ | Copper (I) oxide |
| DAST | (Diethylamino)sulfur trifluride |
| DIPEA | N,N-diisopropylethylamine |
| DMA | N,N-dimethylacetamide |
| DME | 1,2-Dimethoxyethane |
| DMF | N,N-dimethylformamide |
| DMSO | Dimethylsulfoxide |
| DMSO-$d_6$ | Dimethylsulfoxide-$d_6$ |
| EtOAc | Ethyl acetate |
| EtOH | Ethyl alcohol |
| $Et_2O$ | Diethyl ether |
| HBr | Hydrogen bromide |
| HCl | Hydrogen chloride |
| $H_2SO_4$ | Sulfuric acid |
| n-Hex | n-Hexane |
| $HNO_3$ | Nitric acid |
| $H_2O$ | Water |
| $K_2CO_3$ | Potassium carbonate |
| LDA | Lithium diisopropylamide |
| LiOH$H_2O$ | Lithium hydroxide, monohydrate |
| MeOH | Methyl alcohol |
| $NaBH_4$ | Sodium borohydride |
| NaCN | Sodium cyanide |
| $Na_2CO_3$ | Sodium carbonate |
| $Na_2SO_4$ | Sodium sulfate |
| NaH | Sodium hydride |
| $NaHCO_3$ | Sodium bicarbonate |
| NaOH | Sodium hydroxide |
| $NH_4Cl$ | Ammonium chloride |
| NFS | N-fluorobenzenesulfonimide |
| Oxone | Potassium peroxymonosulfate |
| Pd(PPh$_3$)$_4$ | Tetrakis(triphenylphosphine)palladium(0) |
| Pd(OAc)$_2$ | Palladium(II) acetate |
| $PBr_3$ | Phosphorus tribromide |
| $PPh_3$ | Triphenylphosphine |
| $SOCl_2$ | Thionyl chloride |
| THF | Tetrahydrofuran |
| TFA | Trifluoroacetic acid |
| Zn | Zinc |

Intermediate 1) Synthesis of 1-(methylsulfonyl)-2,3-dihydro-1H-thieno[3',2':4,5]benzo[1,2-b][1,4]oxazine-7-carboxylic acid (a) Synthesis of 2-fluoro-4-methoxy-5-nitrobenzaldehyde 2-Fluoro-4-methoxybenzaldehyde (1.0 g, 6.49 mmol) was dissolved in conc. $H_2SO_4$ (6.0 mL), and 70% $HNO_3$ aqueous solution (0.8 mL, 6.49 mmol) and conc. $H_2SO_4$ (0.8 mL, 14.92 mmol) were slowly added at −15° C. The reaction mixture was stirred at −15° C. for 2 hours and poured into ice water. The precipitate was filtered and dissolved in $CH_2Cl_2$ and neutralized with sat. $NaHCO_3$ aqueous solution. The organic extract was dried over anhydrous $Na_2SO_4$ and concentrated under reduced pressure. The residue was purified by flash column chromatography (silica gel, n-Hex:$CH_2Cl_2$=3:1) to obtain 2-fluoro-4-methoxy-5-nitrobenzaldehyde (1.2 g, 91%) as a white solid.

$^1$H-NMR (400 MHz, $CDCl_3$): δ 10.21 (s, 1H), 8.46 (d, 1H, J=7.2 Hz), 6.88 (d, 1H, J=11.6 Hz), 4.06 (s, 3H)

(b) Synthesis of methyl 6-methoxy-5-nitrobenzo[b]thiophene-2-carboxylate

2-Fluoro-4-methoxy-5-nitrobenzaldehyde (1.2 g, 6.43 mmol) was dissolved in anhydrous DMF (16.0 mL), and methyl 2-mercaptoacetate (575.0 μL, 6.43 mmol) and $K_2CO_3$ (1.8 g, 12.80 mmol) were added. The reaction mixture was stirred at 80° C. for 2 hours, $H_2O$ was added, and extracted with EtOAc. The organic extract was washed with brine, dried over anhydrous $Na_2SO_4$ and concentrated under reduced pressure to obtain methyl 6-methoxy-5-nitrobenzo[b]thiophene-2-carboxylate (1.5 g) as a yellow solid without purification.

$^1$H-NMR (400 MHz, $CDCl_3$): δ 8.34 (s, 1H), 8.03 (s, 1H), 7.47 (s, 1H), 4.04 (s, 3H), 3.96 (s, 3H)

(c) Synthesis of methyl 5-amino-6-methoxybenzo[b]thiophene-2-carboxylate

Methyl 6-methoxy-5-nitrobenzo[b]thiophene-2-carboxylate (1.3 g, 4.83 mmol) was dissolved in a mixture of $MeOH/H_2O$ (44.0 mL, 10/1 v/v), and Zn (3.1 g, 65.30 mmol) and $NH_4Cl$ (2.6 g, 53.40 mmol) were added at room temperature. The reaction mixture was stirred at room temperature for 15 hours, filtered through Celite, and concentrated under reduced pressure. The residue was purified by flash column chromatography (amine silica gel, n-Hex:EtOAc=4:1) to obtain methyl-5-amino-6-methoxybenzo[b]thiophene-2-carboxylate (1.1 g, 93%) as a yellow solid.

$^1$H-NMR (400 MHz, $CDCl_3$): δ 7.84 (s, 1H), 7.17 (s, 1H), 7.12 (s, 1H), 3.94-3.96 (m, 5H), 3.91 (s, 3H)

(d) Synthesis of methyl 5-amino-6-hydroxybenzo[b]thiophene-2-carboxylate

Methyl 5-amino-6-methoxybenzo[b]thiophene-2-carboxylate (500.0 mg, 4.83 mmol) was dissolved in $CH_2Cl_2$ (40.0 mL), and 1M solution of $BBr_3$ in $CH_2Cl_2$ (6.7 mL, 6.74 mmol) was added at 0° C. The reaction mixture was stirred at room temperature for 30 minutes, $H_2O$ was added, and extracted with $CH_2Cl_2$. The organic extract was washed with brine, dried over anhydrous $Na_2SO_4$ and concentrated under reduced pressure. The residue was purified by reversed-phase column chromatography (C18-silica gel, 0.1% formic acid in $CH_3CN$:0.1% formic acid in $H_2O$) to obtain methyl 5-amino-6-hydroxybenzo[b]thiophene-2-carboxylate (398.0 mg, 85%) as a gray solid.

LC/MS ESI (+): 224 (M+1)
$^1$H-NMR (400 MHz, DMSO-$d_6$): δ 10.15 (brs, 1H), 7.85 (s, 1H), 7.15 (s, 1H), 7.07 (s, 1H), 4.86 (brs, 2H) 3.82 (s, 3H)

(e) Synthesis of methyl 2,3-dihydro-1H-thieno[3',2':4,5]benzo[1,2-b][1,4]oxazine-7-carboxylate Methyl 5-amino-6-hydroxybenzo[b]thiophene-2-carboxylate (85.0 mg, 0.38 mmol) was dissolved in anhydrous DMF (3.8 mL), and 1,2-dibromoethane (215.0 mg, 1.14 mmol) and $K_2CO_3$ (116.0 mg, 0.83 mmol) were added at room temperature. The reaction mixture was stirred at 75° C. for 15 hours, $H_2O$ was added, and extracted with EtOAc. The organic extract was washed with brine, dried over anhydrous $Na_2SO_4$ and concentrated under reduced pressure. The residue was purified by reversed-phase column chromatography (C18-silica gel, 0.1% formic acid in $CH_3CN$:0.1% formic acid in $H_2O$) to obtain methyl 2,3-dihydro-1H-thieno[3',2':4,5]benzo[1,2-b][1,4]oxazine-7-carboxylate (45.2 mg, 47%) as a gray solid.

LC/MS ESI (+): 250 (M+1)
$^1$H-NMR (400 MHz, DMSO-$d_6$): δ 7.89 (s, 1H), 7.26 (s, 1H), 7.07 (s, 1H), 6.16 (s, 1H), 4.19 (t, 2H, J=4.6 Hz), 3.82 (s, 3H), 3.30-3.32 (m, 2H)

(f) Synthesis of methyl 1-(methylsulfonyl)-2,3-dihydro-1H-thieno[3',2':4,5]benzo[1,2-b][1,4]oxazine-7-carboxylate Methyl 2,3-dihydro-1H-thieno[3',2':4,5]benzo[1,2-b][1,4]oxazine-7-carboxylate (69.0 mg, 0.27 mmol) was dissolved in $CH_2Cl_2$ (2.7 mL), $CH_3SO_2Cl$ (28.0 μL, 0.36 mmol) was added dropwise at 0° C. The reaction mixture was stirred at room temperature for 1 hour, $H_2O$ was added, and extracted with $CH_2Cl_2$. The organic extract was washed with brine, dried over anhydrous $Na_2SO_4$ and concentrated under reduced pressure. The residue was purified by reversed-phase column chromatography (C18-silica gel, 0.1% formic acid in $CH_3CN$:0.1% formic acid in $H_2O$) to obtain methyl 1-(methylsulfonyl)-2,3-dihydro-1H-thieno[3',2':4,5]benzo[1,2-b][1,4]oxazine-7-carboxylate (42.3 mg, 46%) as a white solid.

LC/MS ESI (+): 328 (M+1)
$^1$H-NMR (400 MHz, DMSO-$d_6$): δ 8.21 (s, 1H), 8.12 (s, 1H), 7.63 (s, 1H), 4.35 (t, 2H, J=4.3 Hz), 3.86-3.89 (m, 5H), 3.17 (s, 3H)

(g) Synthesis of 1-(methylsulfonyl)-2,3-dihydro-1H-thieno[3',2':4,5]benzo[1,2-b][1,4]oxazine-7-carboxylic acid The synthesis procedure of Intermediate 1-g was repeated except for using methyl 1-(methylsulfonyl)-2,3-dihydro-1H-thieno[3',2':4,5]benzo[1,2-b][1,4]oxazine-7-carboxylate (42.0 mg, 0.12 mmol) to obtain 1-(methylsulfonyl)-2,3-dihydro-1H-thieno[3',2':4,5]benzo[1,2-b][1,4]oxazine-7-carboxylic acid (35.1 mg, 87%) as a white solid.

LC/MS ESI (−): 312 (M−1)
$^1$H-NMR (400 MHz, DMSO-$d_6$): δ 13.32 (brs, 1H), 8.18 (s, 1H), 8.00 (s, 1H), 7.60 (s, 1H), 4.36 (t, 2H, J=4.7 Hz), 3.89 (t, 2H, J=4.7 Hz), 3.18 (s, 3H)

Intermediate 2) Synthesis of 3,3-dimethyl-1-(methylsulfonyl)-2,3-dihydro-1H-thieno[3',2':4,5]benzo[1,2-b][1,4]oxazine-7-carboxylic acid (a) Synthesis of methyl 5-(2-bromo-2-methylpropanamido)-6-hydroxybenzo[b]thiophene-2-carboxylate Methyl 5-amino-6-hydroxybenzo[b]thiophene-2-carboxylate (110.0 mg, 0.49 mmol) was dissolved in DMA (5.0 mL), and 2-bromo-2-methyl propanoyl bromide (73.0 μL, 0.59 mmol) and DIPEA (258.0 μL, 1.47 mmol) were added. The reaction mixture was stirred at room temperature for 3 hours, $H_2O$ was added, and extracted with EtOAc. The organic extract was washed with brine, dried over anhydrous $Na_2SO_4$ and concentrated under reduced pressure. The residue was purified by reversed-phase column chromatography (C18-silica gel, 0.1% formic acid in $CH_3CN$:0.1% formic acid in H$_2$O) to obtain methyl 5-(2-bromo-2-methylpropanamido)-6-hydroxybenzo[b]thiophene-2-carboxylate (161.0 mg, 88%) as a white solid.

LC/MS ESI (+): 372 (M+1)

$^1$H-NMR (400 MHz, DMSO-d$_6$): δ 11.15 (brs, 1H), 9.24 (s, 1H), 8.49 (s, 1H), 8.08 (s, 1H), 7.43 (s, 1H), 3.85 (s, 3H), 2.03 (s, 6H)

(b) Synthesis of methyl 3,3-dimethyl-2-oxo-2,3-dihydro-1H-thieno[3',2':4,5]benzo[1,2-b][1,4]oxazine-7-carboxylate Methyl 5-(2-bromo-2-methylpropanamido)-6-hydroxybenzo[b]thiophene-2-carboxylate (161.0 mg, 0.43 mmol) was dissolved in DMA (4.3 mL) and K$_2$CO$_3$ (132.0 mg, 0.95 mmol) was added. The reaction mixture was stirred at 60° C. for 15 hours, H$_2$O was added, and extracted with EtOAc. The organic extract was washed with brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain methyl 3,3-dimethyl-2-oxo-2,3-dihydro-1H-thieno[3',2':4,5]benzo[1,2-b][1,4]oxazine-7-carboxylate (112.0 mg, 89%) as a gray solid.

LC/MS ESI (−): 290 (M−1)

$^1$H-NMR (400 MHz, DMSO-d$_6$): δ 10.95 (s, 1H), 8.14 (s, 1H), 7.66 (s, 1H), 7.46 (s, 1H), 3.86 (s, 3H), 1.44 (s, 6H)

(c) Synthesis of methyl 3,3-dimethyl-2,3-dihydro-1H-thieno[3',2':4,5]benzo[1,2-b][1,4]oxazine-7-carboxylate Methyl 3,3-dimethyl-2-oxo-2,3-dihydro-1H-thieno[3',2':4,5]benzo[1,2-b][1,4]oxazine-7-carboxylate (112.0 mg, 0.38 mmol) was dissolved in THF (4.0 mL), and 1M solution of BH$_3$-THF complex (1.9 mL, 1.92 mmol) was added at 0° C. The reaction mixture was stirred at room temperature for 3 hours, H$_2$O was added, and extracted with EtOAc. The organic extract was washed with brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain methyl 3,3-dimethyl-2,3-dihydro-1H-thieno[3',2':4,5]benzo[1,2-b][1,4]oxazine-7-carboxylate (80.0 mg, 75%) as a gray solid.

LC/MS ESI (+): 278 (M+1)

$^1$H-NMR (400 MHz, DMSO-d$_6$): δ 7.90 (s, 1H), 7.23 (s, 1H), 7.11 (s, 1H), 6.26 (brs, 1H), 3.83 (s, 3H) 3.06 (d, 2H, J=2.3 Hz), 1.29 (s, 6H)

(d) Synthesis of methyl 3,3-dimethyl-1-(methylsulfonyl)-2,3-dihydro-1H-thieno[3',2':4,5]benzo[1,2-b][1,4]oxazine-7-carboxylate Methyl 3,3-dimethyl-2,3-dihydro-1H-thieno[3',2':4,5]benzo[1,2-b][1,4]oxazine-7-carboxylate (65.0 mg, 0.88 mmol) was dissolved in pyridine (2.3 mL) and CH$_3$SO$_2$Cl (95.0 μL, 1.06 mmol) was added dropwise at 0° C. The reaction mixture was stirred at room temperature for 15 hours, H$_2$O was added, and extracted with EtOAc. The organic extract was washed with brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain methyl 3,3-dimethyl-1-(methylsulfonyl)-2,3-dihydro-1H-thieno[3',2':4,5]benzo[1,2-b][1,4]oxazine-7-carboxylate (52.2 mg, 63%) as a white solid.

LC/MS ESI (+): 356 (M+1)

$^1$H-NMR (400 MHz, DMSO-d$_6$): δ 8.20 (s, 1H), 8.11 (s, 1H), 7.56 (s, 1H), 3.87 (s, 3H), 3.67 (s, 2H), 3.37 (s, 3H), 1.36 (s, 6H)

(e) Synthesis of 3,3-dimethyl-1-(methylsulfonyl)-2,3-dihydro-1H-thieno[3',2':4,5]benzo[1,2-b][1,4]oxazine-7-carboxylic acid The synthesis procedure of Intermediate 1-g was repeated except for using methyl 3,3-dimethyl-1-(methylsulfonyl)-2,3-dihydro-1H-thieno[3',2':4,5]benzo[1,2-b][1,4]oxazine-7-carboxylate (52.0 mg, 0.14 mmol) as a starting material to obtain 3,3-dimethyl-1-(methylsulfonyl)-2,3-dihydro-1H-thieno[3',2':4,5]benzo[1,2-b][1,4]oxazine-7-carboxylic acid (45.0 mg, 90%).

LC/MS ESI (+): 342 (M+1)

$^1$H-NMR (400 MHz, DMSO-d$_6$): δ 13.30 (s, 1H), 8.17 (s, 1H), 8.01 (s, 1H), 7.53 (s, 1H), 3.66 (s, 2H), 3.34 (s, 3H), 1.36 (s, 6H)

Intermediate 3) Synthesis of 1-(methylsulfonyl)-1,2,3,4-tetrahydrothieno[3',2':4,5]benzo[1,2-b][1,4]oxazephine-8-carboxylic acid (a) Synthesis of methyl 6-hydroxy-5-(methylsulfonamido)benzo[b]thiophene-2-carboxylate Methyl 5-amino-6-hydroxybenzo[b]thiophene-2-carboxylate (126.0 mg, 0.56 mmol) was dissolved in pyridine (2.8 mL), and CH$_3$SO$_2$Cl (50.6 μL, 0.64 mmol) was added dropwise. The reaction mixture was stirred at room temperature for 2 hours, H$_2$O was added, and extracted with EtOAc. The organic extract was washed with brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain methyl 6-hydroxy-5-(methylsulfonamido)benzo[b]thiophene-2-carboxylate (131.0 mg, 77%) as a white solid.

LC/MS ESI (−): 300 (M−1)

$^1$H-NMR (400 MHz, DMSO-d$_6$): δ 9.92 (brs, 1H), 8.08 (s, 1H), 7.85 (s, 1H), 7.43 (s, 1H), 3.86 (s, 3H), 2.99 (s, 3H)

(b) Synthesis of methyl 1-(methylsulfonyl)-1,2,3,4-tetrahydrothieno[3',2':4,5]benzo[1,2-b][1,4]oxazephine-8-carboxylate Methyl 6-hydroxy-5-(methylsulfonamido)benzo[b]thiophene-2-carboxylate (5.0 mg, 0.02 mmol) as a starting material was dissolved in DMA (160.0 μL), and 1,3-dibromopropane (16.7 mg, 0.08 mmol) and K$_2$CO$_3$ (116.0 mg, 0.83 mmol) were added. The reaction mixture was stirred at room temperature for 15 hours, H$_2$O was added, and extracted with EtOAc. The organic extract was washed with brine, dried over anhydrous Na$_2$SO$_4$ and reduced pressure. The residue was purified by flash column chromatography (silica gel, n-Hex:EtOAc=2:1) to obtain methyl 1-(methylsulfonyl)-1,2,3,4-tetrahydrothieno[3',2':4,5]benzo[1,2-b][1,4]oxazephine-8-carboxylate (1.2 mg, 21%) as a white solid.

LC/MS ESI (+): 342 (M+1)

$^1$H-NMR (400 MHz, DMSO-d$_6$): δ 8.20 (s, 1H), 8.07 (s, 1H), 7.86 (s, 1H), 4.13-4.15 (m, 2H), 3.89 (s, 3H), 3.72-3.75 (m, 2H), 3.09 (s, 3H), 2.04-2.07 (m, 2H)

(c) Synthesis of 1-(methylsulfonyl)-1,2,3,4-tetrahydrothieno[3',2':4,5]benzo[1,2-b][1,4]oxazephine-8-carboxylic acid The synthesis procedure of Intermediate 1-g was repeated except for using methyl 1-(methylsulfonyl)-1,2,3,4-tetrahydrothieno[3',2':4,5]benzo[1,2-b][1,4]oxazephine-8-carboxylate (42.0 mg, 0.12 mmol) as a starting material to obtain 1-(methylsulfonyl)-1,2,3,4-tetrahydrothieno[3',2':4,5]benzo[1,2-b][1,4]oxazephine-8-carboxylic acid (22.3 mg, 55%).
LC/MS ESI (+): 328 (M+1)
$^1$H-NMR (400 MHz, DMSO-$d_6$): δ 13.52 (brs, 1H), 8.09 (s, 1H), 8.04 (s, 1H), 7.83 (s, 1H), 4.12-4.14 (m, 2H), 3.73-3.75 (m, 2H), 3.09 (s, 3H), 1.99-2.07 (m, 2H)

Intermediate 4) Synthesis of 8,8-dimethyl-5-(methylsulfonyl)-5,6,7,8-tetrahydrothieno[2,3-g]quinoline-2-carboxylic acid (a) Synthesis of ethyl 5-(3-methylbut-2-enamido)benzo[b]thiophene-2-carboxylate Ethyl 5-aminobenzo[b]thiophene-2-carboxylate (1.5 g, 6.78 mmol) was dissolved in pyridine (33.9 mL), and 3-methylbut-2-enoyl chloride (755.0 μL, 6.78 mmol) was added. The reaction mixture was stirred at room temperature for 1 hour, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=9:1) to obtain ethyl 5-(3-methylbut-2-enamido)benzo[b]thiophene-2-carboxylate (1.3 g, 63%) as a colorless liquid.
$^1$H-NMR (400 MHz, CDCl$_3$): δ 8.29 (s, 1H), 7.99 (s, 1H), 7.77 (d, 1H, J=8.7 Hz), 7.44 (d, 1H, J=8.6 Hz), 7.17 (s, 1H), 5.74 (s, 1H), 4.40 (q, 2H, J=7.1 Hz), 2.26 (s, 3H), 1.93 (s, 3H), 1.41 (t, 3H, J=7.1 Hz)

(b) Synthesis of ethyl 8,8-dimethyl-6-oxo-5,6,7,8-tetrahydrothieno[2,3-g]quinoline-2-carboxylate Ethyl 5-(3-methylbut-2-enamido)benzo[b]thiophene-2-carboxylate (1.3 g, 4.29 mmol) was dissolved in CH$_2$Cl$_2$ (42.9 mL), and AlCl$_3$ (1.7 g, 12.86 mmol) was added at 0° C. The reaction mixture was stirred at room temperature for 2 hours, H$_2$O was added, and extracted with CH$_2$Cl$_2$. The organic extract was washed with brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain ethyl 8,8-dimethyl-6-oxo-5,6,7,8-tetrahydrothieno[2,3-g]quinoline-2-carboxylate (250.0 mg, 19%) as a yellow solid.
$^1$H-NMR (400 MHz, CDCl$_3$): δ 8.44 (s, 1H), 8.41 (s, 1H), 7.94 (s, 1H), 7.76 (s, 1H), 4.42 (q, 2H, J=7.1 Hz), 2.55 (s, 2H), 1.59 (s, 6H), 1.43 (t, 3H, J=7.1 Hz)

(c) Synthesis of ethyl 8,8-dimethyl-5,6,7,8-tetrahydrothieno[2,3-g]quinoline-2-carboxylate The synthesis procedure of Intermediate 15-c was repeated except for using ethyl 8,8-dimethyl-6-oxo-5,6,7,8-tetrahydrothieno[2,3-g]quinoline-2-carboxylate (217.0 mg, 0.72 mmol) as a starting material to obtain ethyl 8,8-dimethyl-5,6,7,8-tetrahydrothieno[2,3-g]quinoline-2-carboxylate (56.0 mg, 27%).
$^1$H-NMR (400 MHz, CDCl$_3$): δ 7.78 (s, 1H), 7.63 (s, 1H), 6.88 (s, 1H), 4.37 (q, 2H, J=7.1 Hz), 3.37 (t, 2H, J=5.8 Hz), 1.78 (t, 2H, J=5.8 Hz), 1.37-1.41 (m, 9H)

(d) Synthesis of ethyl 8,8-dimethyl-5-(methylsulfonyl)-5,6,7,8-tetrahydrothieno[2,3-g]quinoline-2-carboxylate The synthesis procedure of Intermediate 16-f was repeated except for using ethyl 8,8-dimethyl-5,6,7,8-tetrahydrothieno[2,3-g]quinoline-2-carboxylate (56.0 mg, 0.19 mmol) as a starting material to obtain ethyl 8,8-dimethyl-5-(methylsulfonyl)-5,6,7,8-tetrahydrothieno[2,3-g]quinoline-2-carboxylate (57.0 mg, 80%).
$^1$H-NMR (400 MHz, CDCl$_3$): δ 8.21 (s, 1H), 7.97 (s, 1H), 7.83 (s, 1H), 4.40 (q, 2H, J=7.1 Hz), 3.90 (t, 2H, J=5.8 Hz), 2.92 (s, 3H), 1.88 (t, 2H, J=5.8 Hz), 1.39-1.43 (m, 9H)

(e) Synthesis of 8,8-dimethyl-5-(methylsulfonyl)-5,6,7,8-tetrahydrothieno[2,3-g]quinoline-2-carboxylic acid The synthesis procedure of Intermediate 1-g was repeated except for using ethyl 8,8-dimethyl-5-(methylsulfonyl)-5,6,7,8-tetrahydrothieno[2,3-g]quinoline-2-carboxylate (57.0 mg, 0.16 mmol) as a starting material to obtain 8,8-dimethyl-5-(methylsulfonyl)-5,6,7,8-tetrahydrothieno[2,3-g]quinoline-2-carboxylic acid (52.0 mg, 80%).
LC/MS ESI (+): 340 (M+1)
$^1$H-NMR (400 MHz, CDCl$_3$): δ 8.25 (s, 1H), 8.08 (s, 1H), 7.87 (s, 1H), 3.91 (t, 2H, J=5.8 Hz), 2.94 (s, 3H), 1.89 (t, 2H, J=5.8 Hz), 1.43 (s, 6H)

Intermediate 5) Synthesis of 4-(tert-butoxycarbonyl)-1-(methylsulfonyl)-1,2,3,4-tetrahydrothieno[2,3-g]quinoxaline-7-carboxylic acid (a) Synthesis of 4-bromo-2-fluoro-5-nitrobenzaldehyde 4-bromo-2-fluorobenzaldehyde (2.0 g, 9.85 mmol) was dissolved in conc. H$_2$SO$_4$ (5.2 mL, 98.50 mmol), and 60% HNO$_3$ (1.0 mL, 12.80 mmol) was added at 0° C. The reaction mixture was stirred for 4 hours, and extracted with CH$_2$Cl$_2$. The organic extract was washed with brine, dried over anhydrous Na$_2$SO$_4$ and concentrated under reduced pressure. The residue was recrystallized using i-Pr$_2$O to obtain 4-bromo-2-fluoro-5-nitrobenzaldehyde (900.0 mg, 37%) as a white solid.
$^1$H-NMR (400 MHz, CDCl$_3$): δ 10.31 (s, 1H), 8.42 (d, 1H, J=6.4 Hz), 7.67 (d, 1H, J=9.0 Hz).

(b) Synthesis of methyl 6-bromo-5-nitrobenzo[b]thiophene-2-carboxylate 4-bromo-2-fluoro-5-nitrobenzaldehyde (5.0 g, 20.10 mmol) was dissolved in anhydrous DMF (50.0 mL), and methyl 2-mercaptoacetate (2.1 g, 20.10 mmol) and K$_2$CO$_3$ (5.6 g, 40.30 mmol) were added, followed by heating at 80° C. for 2 hours. The reaction mixture was cooled to room temperature and extracted with EtOAc. The organic extract was washed with brine, dried over anhydrous Na$_2$SO$_4$, concentrated under reduced pressure. The residue was purified by reversed-phase column chromatography (C18-silica gel, 0.1% formic acid in CH$_3$CN:0.1% formic acid in H$_2$O) to obtain 6-bromo-5-nitrobenzo[b]thiophene-2-carboxylate (3.4 g, 53%) as a yellow solid.

¹H-NMR (400 MHz, DMSO-d₆): δ 8.38 (s, 1H), 8.23 (s, 1H), 8.09 (s, 1H), 3.98 (s, 3H)

(c) Synthesis of methyl 6-amino-5-nitrobenzo[b]thiophene-2-carboxylate 6-bromo-5-nitrobenzo[b]thiophene-2-carboxylate (3.0 g, 9.49 mmol) was dissolved in DMSO (10.0 ml) and Cu₂O (830.0 mg, 10.40 mmol), sodium azide (1.2 g, 18.90 mmol) were added at room temperature. The mixture was stirred at 100° C. for 1 hour and extracted with EtOAc. The organic extract was washed with brine, dried over anhydrous Na₂SO₄ and concentrated under reduced pressure. The residue was purified by reversed-phase column chromatography (C18-silica gel, 0.1% formic acid in CH₃CN:0.1% formic acid in H₂O) to obtain methyl 6-amino-5-nitrobenzo[b]thiophene-2-carboxylate (1.6 g, 66%). as an off-white solid.
LC/MS ESI (+): 253 (M+1)
¹H-NMR (400 MHz, CDCl₃): δ 8.77 (s, 1H), 8.11 (s, 1H), 7.44 (s, 1H), 7.39 (s, 2H), 3.33 (s, 3H)

(d) Synthesis of methyl 6-((tert-butoxycarbonyl)amino)-5-nitrobenzo[b]thiophene-2-carboxylate Methyl 6-amino-5-nitrobenzo[b]thiophene-2-carboxylate (800.0 mg, 3.17 mmol) was dissolved in DMA (10.0 mL) and Boc₂O (831.0 mg, 3.81 mmol), DIPEA (1.6 mL, 9.51 mmol) were added at room temperature. The mixture was stirred at 100° C. for 2 hours and extracted with EtOAc. The organic extract was washed with brine, dried over anhydrous Na₂SO₄ and concentrated under reduced pressure. The residue was purified by reversed-phase column chromatography (C18-silica gel, 0.1% formic acid in CH₃CN:0.1% formic acid in H₂O) to obtain methyl 6-((tert-butoxycarbonyl)amino)-5-nitrobenzo[b]thiophene-2-carboxylate (663.0 mg, 59%), as an off-white solid.
¹H-NMR (400 MHz, CDCl₃): δ 9.59 (s, 1H), 8.74 (s, 1H), 8.32 (s, 1H), 8.31 (s, 1H), 3.91 (s, 3H), 1.46 (s, 9H)

(e) Synthesis of methyl 5-amino-6-((tert-butoxycarbonyl)amino)benzo[b]thiophene-2-carboxylate Methyl 6-((tert-butoxycarbonyl)amino)-5-nitrobenzo[b]thiophene-2-carboxylate (662.0 mg, 1.87 mmol) was dissolved in a mixture solvent of MeOH/H₂O (20.0 mL, 9/1 v/v), and Zn (18.7 g, 18.70 mmol) and NH₄Cl (1.0 g, 18.70 mmol) were added thereto, and an ultrasonic reaction was conducted at 30° C. for 15 hours. The reaction mixture was filtered through Celite and concentrated under a reduced pressure. The residue was purified by reversed-phase column chromatography (C18-silica gel, 0.1% formic acid in CH₃CN:0.1% formic acid in H₂O) to obtain methyl 5-amino-6-((tert-butoxycarbonyl) amino) benzo [b]thiophene-2-carboxylate (633.0 mg, 104%) as an off-white solid.
LC/MS ESI (+): 323 (M+1)
¹H-NMR (400 MHz, CDCl₃): δ 8.56 (s, 1H), 8.01 (s, 1H), 7.92 (s, 1H), 7.21 (s, 1H), 5.14 (s, 2H), 3.85 (s, 3H), 1.50 (s, 9H)

(f) Synthesis of methyl 6-((tert-butoxycarbonyl)amino)-5-(methylsulfonamido) benzo[b]thiophene-2-carboxylate Methyl 5-amino-6-((tert-butoxycarbonyl) amino) benzo[b]thiophene-2-carboxylate (633.0 mg, 1.96 mmol) was dissolved in pyridine (9.8 mL), and methanesulfonyl chloride (168.0 μL, 2.16 mmol) was slowly added thereto at 0° C. The reaction mixture was warmed to room temperature, followed by stirred for 3 hours and extracted with EtOAc. The organic extract was washed with brine, dried over anhydrous Na₂SO₄ and concentrated under reduced pressure. The residue was purified by reversed-phase column chromatography (C18-silica gel, 0.1% formic acid in CH₃CN:0.1% formic acid in H₂O) to obtain methyl 6-((tert-butoxycarbonyl)amino)-5-(methylsulfonamido)benzo[b]thiophene-2-carboxylate (694.0 mg, 88%), as an off-white solid.
LC/MS ESI (−): 399 (M−1)
¹H-NMR (400 MHz, DMSO-d₆): δ 9.28 (s, 1H), 8.55 (s, 1H), 8.41 (s, 1H), 8.16 (s, 1H), 7.99 (s, 1H), 3.89 (s, 3H), 3.02 (s, 3H), 1.51 (s, 9H)

(g) Synthesis of 4-(tert-butyl) 7-methyl 1-(methylsulfonyl)-2,3-dihydrothieno[2,3-g]quinoxaline-4,7(1H)-dicarboxylate Methyl 6-((tert-butoxycarbonyl)amino)-5-(methylsulfonamido) benzo[b]thiophene-2-carboxylate (684.0 mg, 1.70 mmol) was dissolved in DMA (17.1 mL), and 1,2-dibromoethane (963.0 mg, 5.12 mmol) and K₂CO₃ (472.0 mg, 3.42 mmol) were slowly added at room temperature. The mixture was stirred for 1 hour, and the reaction mixture was extracted with EtOAc. The organic extract was washed with brine, dried over anhydrous Na₂SO₄ and concentrated under reduced pressure. The residue was purified by reversed-phase column chromatography (C18-silica gel, 0.1% formic acid in CH₃CN:0.1% formic acid in H₂O) to obtain 4-(tert-butyl) 7-methyl 1-(methylsulfonyl)-2,3-dihydrothieno[2,3-g]quinoxaline-4,7(1H)-dicarboxylate (495.0 mg, 68%), as an off-white solid.
¹H-NMR (400 MHz, DMSO-d₆): δ 8.42 (s, 1H), 8.17 (s, 1H), 8.12 (s, 1H), 3.85-3.92 (m, 4H), 3.89 (s, 3H), 3.12 (s, 3H), 1.51 (s, 9H)

(h) Synthesis of 4-(tert-butoxycarbonyl)-1-(methylsulfonyl)-1,2,3,4-tetrahydrothieno[2,3-g]quinoxaline-7-carboxylic acid 4-(tert-butyl) 7-methyl 1-(methylsulfonyl)-2,3-dihydrothieno[2,3-g]quinoxaline-4,7(1H)-dicarboxylate (495.0 mg, 1.16 mmol) was dissolved in THF/H₂O (10.0 mL, 3/1 v/v), and LiOH.H₂O (146.0 mg, 3.48 mmol) was added. After stirring at room temperature for 2 hours, the reaction mixture was concentrated under a reduced pressure. The residue was diluted in H₂O (1.0 mL), and acidified with 1N HCl (pH 1-2). The precipitate was filtered to obtain 4-(tert-butoxycarbonyl)-1-(methylsulfonyl)-1,2,3,4-tetrahydrothieno[2,3-g]quinoxaline-7-carboxylic acid (422.0 mg, 88%) as a white solid.
LC/MS ESI (−): 411 (M−1)
¹H-NMR (400 MHz, DMSO-d₆): δ 13.47 (brs, 1H), 8.37 (s, 1H), 8.09 (s, 1H), 8.05 (s, 1H), 3.83~3.92 (m, 4H), 3.11 (s, 3H), 1.50 (s, 9H)

Intermediate 6) Synthesis of 5-(methylsulfonyl)-5,6,7,8-tetrahydrothieno[2,3-g]quinoline-2-carboxylic acid (a) Synthesis of methyl (E)-6-(3-methoxy-3-oxoprop-1-en-1-yl)-5-nitrobenzo[b]thiophene-2-carboxylate Methyl 6-bromo-5-nitrobenzo[b]thiophene-2-carboxylate (0.4 g, 1.26 mmol) was dissolved in anhydrous DMF (12.6 ml), and Pd(OAc)$_2$ (28.0 mg, 0.13 mmol), PPh$_3$ (66.0 mg, 0.25 mmol), TEA (0.4 ml, 2.53 mmol) and methyl acrylate (0.6 ml, 6.33 mmol) were added. The reaction mixture was stirred at 130° C. for 30 minutes, and extracted with EtOAc. The organic extract was washed with brine, dried over anhydrous Na$_2$SO$_4$ and concentrated under reduced pressure. The residue was recrystallized with diethyl ether to obtain methyl (E)-6-(3-methoxy-3-oxoprop-1-en-1-yl)-5-nitrobenzo[b]thiophene-2-carboxylate as a white solid.

LC/MS ESI (+): 322 (M+1)

$^1$H-NMR (400 MHz, CDCl$_3$): δ 8.62 (s, 1H), 8.16-8.22 (m, 2H), 8.09 (s, 1H), 6.43 (d, 1H, J=16.0 Hz), 4.00 (s, 3H), 3.85 (s, 3H)

(b) Synthesis of methyl 6-oxo-5,6,7,8-tetrahydrothieno[2,3-g]quinoline-2-carboxylate (E)-methyl 6-(3-methoxy-3-oxoprop-1-en-1-yl)-5-nitrobenzo[b]thiophene-2-carboxylate (0.2 g, 0.62 mmol) was dissolved in anhydrous MeOH (15.6 mL), and 5% Pd—C (20.0 mg, 0.19 mmol) was added. The reaction mixture was charged with H$_2$ gas and stirred at 25° C. for 4 days. The residue was filtered through Celite and concentrated under reduced pressure to obtain methyl 6-oxo-5,6,7,8-tetrahydrothieno[2,3-g]quinoline-2-carboxylate (100.0 mg, 61%) as a white solid without purification.

LC/MS ESI (+): 262 (M+1)

$^1$H-NMR (400 MHz, CDCl$_3$): δ 7.95 (s, 1H), 7.80 (brs, 1H), 7.66 (s, 1H), 7.21 (s, 1H), 3.94 (s, 3H), 3.11 (t, 2H, J=7.2 Hz), 2.69 (t, 2H, J=7.2 Hz)

(c) Synthesis of methyl 5,6,7,8-tetrahydrothieno[2,3-g]quinoline-2-carboxylate

Methyl 6-oxo-5,6,7,8-tetrahydrothieno[2,3-g]quinoline-2-carboxylate (100.0 mg, 0.38 mmol) was dissolved in THF (4.0 mL), and 1M solution of BH$_3$-THF complex (1.9 mL, 1.91 mmol) was added at 0° C. The reaction mixture was stirred at room temperature for 3 hours, H$_2$O was added, and extracted with EtOAc. The organic extract was washed with brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain methyl 5,6,7,8-tetrahydrothieno[2,3-g]quinoline-2-carboxylate (65.0 mg, 69%) as a gray solid.

LC/MS ESI (+): 248 (M+1)

$^1$H-NMR (400 MHz, CDCl$_3$): δ 7.80 (s, 1H), 7.40 (s, 1H), 6.89 (s, 1H), 3.91 (s, 3H), 3.35 (t, 2H, J=5.3 Hz), 2.92 (t, 2H, J=6.3 Hz), 1.96-1.99 (m, 2H)

(d) Synthesis of methyl 5-(methylsulfonyl)-5,6,7,8-tetrahydrothieno[2,3-g]quinoline-2-carboxylate Methyl 5,6,7,8-tetrahydrothieno[2,3-g]quinoline-2-carboxylate (50.0 mg, 0.20 mmol) was dissolved in CH$_2$Cl$_2$ (2.0 mL), and CH$_3$SO$_2$Cl (23.6 μL, 0.30 mmol) and DIPEA (70.6 μL, 0.40 mmol) were added at 0° C. The reaction mixture was stirred for 3 hours and extracted with EtOAc. The organic extract was washed with brine, dried over anhydrous Na$_2$SO$_4$ and concentrated under reduced pressure. The residue was purified by flash column chromatography (silica gel, n-Hex:EtOAc=2:1) to obtain methyl 5-(methylsulfonyl)-5,6,7,8-tetrahydrothieno[2,3-g]quinoline-2-carboxylate (57.0 mg, 87%) as a white solid.

LC/MS ESI (+): 326 (M+1)

$^1$H-NMR (400 MHz, CDCl$_3$): δ 8.21 (s, 1H), 7.99 (s, 1H), 7.63 (s, 1H), 3.94 (s, 3H), 3.87 (t, 2H, J=6.0 Hz), 2.99 (t, 2H, J=6.0 Hz), 2.90 (s, 3H), 2.04-2.07 (m, 2H)

(e) Synthesis of 5-(methylsulfonyl)-5,6,7,8-tetrahydrothieno[2,3-g]quinoline-2-carboxylic acid The synthesis procedure of Intermediate 5-h was repeated except for using methyl 5-(methylsulfonyl)-5,6,7,8-tetrahydrothieno[2,3-g]quinoline-2-carboxylate (60.0 mg, 0.18 mmol) to obtain 5-(methylsulfonyl)-5,6,7,8-tetrahydrothieno[2,3-g]quinoline-2-carboxylic acid (450.0 mg, 87%), as a white solid.

LC/MS ESI (+): 312 (M+1)

Intermediate 7) Synthesis of 4-methyl-1-(methylsulfonyl)-1,2,3,4-tetrahydrothieno[2,3-g]quinoxaline-7-carboxylic acid (a) Synthesis of methyl 1-(methylsulfonyl)-1,2,3,4-tetrahydrothieno[2,3-g]quinoxaline-7-carboxylate Unpurified tert-butyl 7-(chlorocarbonyl)-1-(methylsulfonyl)-2,3-dihydrothieno[2,3-g]quinoxaline-4(1H)-carboxylate (40.0 mg, 0.09 mmol) was dissolved in CH$_2$Cl$_2$/MeOH (1.6 mL, 1/1 v/v), and TFA (0.3 mL) was slowly added. After stirring at room temperature for 2 hours, the reaction mixture was concentrated under reduced pressure. The residue was purified by reversed-phase column chromatography (C18-silica gel, 0.1% formic acid in CH$_3$CN:0.1% formic acid in H$_2$O) to obtain methyl 1-(methylsulfonyl)-1,2,3,4-tetrahydrothieno[2,3-g]quinoxaline-7-carboxylate (21.0 mg, 69%) as a white solid.

LC/MS ESI (+): 327 (M+1)

$^1$H-NMR (400 MHz, DMSO-d$_6$): δ 7.97 (s, 1H), 7.90 (s, 1H), 7.09 (s, 1H), 7.00 (s, 1H), 3.82 (s, 3H), 3.67-3.69 (m, 2H), 3.43-3.45 (m, 2H), 3.00 (s, 3H)

(b) Synthesis of methyl 4-methyl-1-(methylsulfonyl)-1,2,3,4-tetrahydrothieno[2,3-g]quinoxaline-7-carboxylate Methyl 1-(methylsulfonyl)-1,2,3,4-tetrahydrothieno[2,3-g]quinoxaline-7-carboxylate (63.0 mg, 0.19 mmol) was dissolved in MeOH (1.9 mL), and formaldehyde (76.0 μL, 0.96 mmol) and sodium cyanoborohydride (36.4 mg, 0.57 mmol) and AcOH (11.0 μL, 0.19 mmol) were added thereto at room temperature. The mixture was stirred for 15 hours, and the reaction mixture was extracted with EtOAc. The organic extract was washed with brine, dried over anhydrous Na$_2$SO$_4$, filtered and concentrated under a reduced pressure. The residue was separated on reversed-phase silica by column chromatography (0.1% formic acid in CH$_3$CN:0.1% formic acid in H$_2$O=70:30), and fractions including the product were combined and evaporated to obtain methyl 4-methyl-1-(methylsulfonyl)-1,2,3,4-tetrahydrothieno[2,3-g]quinoxaline-7-carboxylate (51.0 mg, 78%) as a white solid.

LC/MS ESI (+): 341 (M+1)

$^1$H-NMR (400 MHz, DMSO-d$_6$): δ 8.00 (s, 1H), 7.90 (s, 1H), 7.28 (s, 1H), 3.84 (s, 3H), 3.76 (t, 2H, J=5.3 Hz), 3.51 (t, 2H, J=5.3 Hz), 3.02 (s, 3H), 3.01 (s, 3H)

(c) Synthesis of 4-methyl-1-(methylsulfonyl)-1,2,3,4-tetrahydrothieno[2,3-g]quinoxaline-7-carboxylic acid Methyl 4-methyl-1-(methylsulfonyl)-1,2,3,4-tetrahydrothieno[2,3-g]quinoxaline-7-carboxylate (50.0 mg, 0.14 mmol) was dissolved in THF/H$_2$O (1.5 mL, 3/1 v/v), and LiOH.H$_2$O (18.4 mg, 0.44 mmol) was added thereto. After stirring at room temperature for 2 hours, the reaction mixture was concentrated under a reduced pressure. The residue was diluted in H$_2$O (1.0 mL), and acidified with 1N HCl (pH 1-2). The precipitate was filtered to obtain 4-methyl-1-(methylsulfonyl)-1,2,3,4-tetrahydrothieno[2,3-g]quinoxaline-7-carboxylic acid (42.0 mg, 88%) as a white solid.

LC/MS ESI (+): 327 (M+1)

$^1$H-NMR (400 MHz, DMSO-d$_6$): δ 13.02 (brs, 1H), 7.89 (s, 1H), 7.87 (s, 1H), 7.26 (s, 1H), 3.76 (t, 2H, J=5.4 Hz), 3.50 (t, 2H, J=5.4 Hz), 3.01 (s, 3H), 3.00 (s, 3H)

Intermediate 8) Synthesis of 4-(methylsulfonyl)-3,4-dihydro-2H-thieno[3,2-g]chromene-7-carboxylic acid (a) Synthesis of 2-chloro-4-(3,3-diethoxypropoxy)-1-methylbenzene 3-Chloro-4-methylphenol (3.0 g, 21.04 mmol) was dissolved in anhydrous DMF (105.0 mL), and 3-chloro-1,1-diethoxypropane (4.2 g, 25.20 mmol) and K$_2$CO$_3$ (8.7 g, 63.10 mmol) were added. The reaction mixture was stirred at 80° C. for 15 hours, H$_2$O was added, and extracted with EtOAc. The organic extract was washed with brine, dried over anhydrous Na$_2$SO$_4$ and concentrated under reduced pressure. The residue was purified by flash column chromatography (silica gel, n-Hex:EtOAc=95:5) to obtain 2-chloro-4-(3,3-diethoxypropoxy)-1-methylbenzene (4.0 g, 69%) as a colorless liquid.

$^1$H-NMR (400 MHz, CDCl$_3$): δ 7.16 (d, 1H, J=8.4 Hz), 6.91 (d, 1H, J=2.6 Hz), 6.71 (dd, 1H, J=8.4 Hz, 2.6 Hz), 4.75 (t, 1H, J=5.7 Hz), 4.1 (t, 2H, J=6.3 Hz), 3.66-3.73 (m, 2H), 3.49-3.57 (m, 2H), 2.29 (s, 3H), 2.05-2.10 (m, 2H), 1.22 (t, 6H, J=7.1 Hz).

(b) Synthesis of 7-chloro-6-methyl-4-(methylsulfonyl)chromane

Sodium methane sulfinate (4.5 g, 44.00 mmol) was dissolved in TFA (61.1 mL) and stirred at 0° C. for 10 minutes. A solution of 2-chloro-4-(3,3-diethxypropoxy)-1-methylbenzene (4.0 g, 14.66 mmol) in CH$_2$Cl$_2$ (12.2 mL) was added to the reaction mixture for a period of 1 hour, and stirred at room temperature for 30 minutes. The reaction mixture was basified with sat. NaHCO$_3$ aqueous solution (pH=9-10), and extracted with CH$_2$Cl$_2$. The organic extract was washed with brine, dried over anhydrous Na$_2$SO$_4$ and concentrated under reduced pressure. The residue was purified by flash column chromatography (silica gel, n-Hex:EtOAc=1:2) to obtain 7-chloro-6-methyl-4-(methylsulfonyl)chromane (2.3 g, 60%) as an off-white solid.

$^1$H-NMR (400 MHz, CDCl$_3$): δ 7.36 (s, 1H), 6.95 (s, 1H), 4.40-4.46 (m, 1H), 4.17-4.25 (m, 2H), 2.83 (s, 3H), 2.55-2.62 (m, 1H), 2.32-2.42 (m, 1H), 2.31 (s, 3H).

(c) Synthesis of 6-(bromomethyl)-7-chloro-4-(methylsulfonyl)chromane

7-Chloro-6-methyl-4-(methylsulfonyl)chromane (2.3 g, 8.63 mmol) was dissolved in anhydrous 1,2-dichloroethane (86.0 mL), and N-bromosuccinimide (1.5 g, 8.63 mmol) and AIBN (142.0 mg, 0.86 mmol) were added. The reaction mixture was refluxed at 100° C. for 15 hours, cooled to room temperature, H$_2$O was added, and extracted with CH$_2$Cl$_2$. The organic extract was washed with brine, dried over anhydrous Na$_2$SO$_4$ and concentrated under reduced pressure. The residue was purified by flash column chromatography (silica gel, n-Hex:EtOAc=4:1) to obtain 6-(bromomethyl)-7-chloro-4-(methylsulfonyl)chromane (2.5 g, 85%) as a yellow solid.

$^1$H-NMR (400 MHz, CDCl$_3$): δ 7.59 (s, 1H), 7.00 (s, 1H), 4.47-4.62 (m, 3H), 4.25-4.31 (m, 1H), 4.19-4.22 (m, 1H), 2.87 (s, 3H), 2.56-2.62 (m, 1H), 2.34-2.43 (m, 1H).

(d) Synthesis of 7-chloro-4-(methylsulfonyl)chromane-6-carbaldehyde 6-(Bromomethyl)-7-chloro-4-(methylsulfonyl)chromane (2.5 g, 7.36 mmol) was dissolved in anhydrous CH$_3$CN (73.6 mL), and 4-methylmorpholine N-oxide (1.7 g, 14.72 mmol) and a molecular sieve (3.0 g) were added. The reaction mixture was stirred at room temperature for 2 hours, H$_2$O was added to the reaction mixture, and extracted with EtOAc. The organic extract was washed with brine, dried over anhydrous Na$_2$SO$_4$ and concentrated under reduced pressure. The residue was recrystallized with Et$_2$O to obtain 7-chloro-4-(methylsulfonyl)chromane-6-carbaldehyde (1.3 g, 64%) as a pale yellow solid.

LC/MS ESI (+): 275 (M+1).

$^1$H-NMR (400 MHz, CDCl$_3$): δ 10.32 (s, 1H), 7.97 (s, 1H), 7.03 (s, 1H), 4.64-4.71 (m, 1H), 4.39-4.44 (m, 1H), 4.23 (m, 1H), 2.99 (s, 3H), 2.73-2.78 (m, 1H), 2.30-2.34 (m, 1H).

(e) Synthesis of methyl 4-(methylsulfonyl)-3,4-dihydro-2H-thieno[3,2-g]chromene-7-carboxylate 7-Chloro-4-(methylsulfonyl)chromane-6-carbaldehyde (300.0 mg, 1.09 mmol) was dissolved in anhydrous DMF (10.0 mL), and methyl 2-mercapto acetate (117.0 μL, 1.31 mmol) and Cs$_2$CO$_3$ (1.1 g, 3.28 mmol) were added. The reaction mixture was stirred at 80° C. for 4 hours, cooled to room temperature, H$_2$O was added, and extracted with EtOAc. The organic extract was washed with brine, dried over anhydrous Na$_2$SO$_4$ and concentrated under reduced pressure. The residue was recrystallized with CH$_2$Cl$_2$ and Et$_2$O to obtain methyl 4-(methylsulfonyl)-3,4-dihydro-2H-thieno[3,2-g]chromene-7-carboxylate (200.0 mg, 56%) as a white solid.

$^1$H-NMR (400 MHz, DMSO-d$_6$): δ 8.17 (s, 1H), 8.09 (s, 1H), 7.57 (s, 1H), 4.82 (m, 1H), 4.45-4.50 (m, 1H), 4.31-4.35 (m, 1H), 3.88 (s, 3H), 3.17 (s, 3H), 2.59-2.69 (m, 1H), 2.26-2.37 (m, 1H).

LC/MS ESI (+): 327 (M+1).

(f) Synthesis of 4-(methylsulfonyl)-3,4-dihydro-2H-thieno[3,2-g]chromene-7-carboxylic acid Methyl 4-(methylsulfonyl)-3,4-dihydro-2H-thieno[3,2-g]chromene-7-carboxylate (200.0 mg, 0.61 mmol) was dissolved in THF (4.0 mL)/H$_2$O (2.0 mL), and LiOH.H$_2$O (257.0 mg, 6.13 mmol) was added. The reaction mixture was stirred at 60° C. for 15 hours, 1N HCl (3.0 mL) was added, and extracted with CH$_2$Cl$_2$ and MeOH. The organic extract was washed with brine, dried over anhydrous Na$_2$SO$_4$ and concentrated under reduced pressure to obtain 4-(methylsulfonyl)-3,4-dihydro-2H-thieno[3,2-g]chromene-7-carboxylic acid (140.0 mg, 73%) as an off-white solid.

LC/MS ESI (−): 311 (M−1).

¹H-NMR (400 MHz, DMSO-d₆): δ 13.34 (bs, 1H), 8.06 (s, 2H), 7.54 (s, 1H), 4.82 (m, 1H), 4.45-4.54 (m, 1H), 4.30-4.34 (m, 1H), 3.16 (s, 3H), 2.60-2.74 (m, 1H), 2.28-2.39 (m, 1H).

Intermediate 9) Synthesis of 5-(methylsulfonyl)-2,3,4,5-tetrahydrothieno[3',2':4,5]benzo[1,2-b]oxepine-8-carboxylic acid (a) Synthesis of 2-chloro-4-(4,4-diethoxybutoxy)-1-methylbenzene The synthesis procedure of Intermediate 8-a was repeated except for using 3-chloro-4-methylphenol (1.0 g, 7.01 mmol) to obtain 2-chloro-4-(4,4-diethoxybutoxy)-1-methylbenzene (1.8 g, 89%) as a colorless liquid.

LC/MS ESI (+): 287 (M+1)

¹H-NMR (400 MHz, CDCl₃): δ 7.09 (d, 1H, J=8.0 Hz), 6.89 (d, 1H, J=2.8 Hz), 6.69 (dd, 1H, J=8.6, 2.8 Hz), 4.54 (t, 1H, J=1.6 Hz), 3.93 (t, 2H, J=6.0 Hz), 3.62-3.70 (m, 2H), 3.47-3.54 (m, 2H), 2.28 (s, 3H), 1.74-1.87 (m, 4H), 1.21 (t, 6H, J=7.2 Hz)

(b) Synthesis of 8-chloro-7-methyl-5-(methylsulfonyl)-2,3,4,5-tetrahydrobenzo[b]oxepine The synthesis procedure of Intermediate 8-b was repeated except for using 2-chloro-4-(4,4-diethoxybutoxy)-1-methylbenzene (1.8 g, 6.20 mmol) to obtain 8-chloro-7-methyl-5-(methylsulfonyl)-2,3,4,5-tetrahydrobenzo[b]oxepine (421.0 mg, 23%) as a white solid.

LC/MS ESI (+): 275 (M+1)

¹H-NMR (400 MHz, CDCl₃): δ 7.20 (s, 1H), 7.10 (s, 1H), 4.34-4.39 (m, 1H), 4.16 (t, 1H, J=1.6 Hz), 3.71-3.77 (m, 1H), 2.78 (s, 3H), 2.64-2.70 (m, 1H), 2.33 (s, 3H), 2.22-2.29 (m, 1H), 2.07-2.15 (m, 1H), 1.82-1.89 (m, 1H).

(c) Synthesis of 7-(bromomethyl)-8-chloro-5-(methylsulfonyl)-2,3,4,5-tetrahydrobenzo[b]oxepine The synthesis procedure of Intermediate 8-c was repeated except for using 8-chloro-7-methyl-5-(methylsulfonyl)-2,3,4,5-tetrahydrobenzo[b]oxepine (421 mg, 1.53 mmol) to obtain 7-(bromomethyl)-8-chloro-5-(methylsulfonyl)-2,3,4,5-tetrahydrobenzo[b]oxepine (342.0 mg, 63%) as a white solid.

LC/MS ESI (+): 353 (M+1)

¹H-NMR (400 MHz, CDCl₃): δ 7.42 (s, 1H), 7.15 (s, 1H), 4.44 (m, 2H), 4.39-4.44 (m, 1H), 4.20 (t, 1H, J=1.6 Hz), 3.76-3.82 (m, 1H), 2.78 (s, 3H), 2.68-2.72 (m, 1H), 2.28-2.38 (m, 1H), 2.09-2.18 (m, 1H), 1.86-1.94 (m, 1H)

(d) Synthesis of 8-chloro-5-(methylsulfonyl)-2,3,4,5-tetrahydrobenzo[b]oxepine-7-carbaldehyde The synthesis procedure of Intermediate 8-d was repeated except for using 7-(bromomethyl)-8-chloro-5-(methylsulfonyl)-2,3,4,5-tetrahydrobenzo[b]oxepine (342.0 mg, 0.97 mmol) to obtain 8-chloro-5-(methylsulfonyl)-2,3,4,5-tetrahydrobenzo[b]oxepine-7-carbaldehyde (164.0 mg, 57%), as a white solid.

LC/MS ESI (+): 289 (M+1)

¹H-NMR (400 MHz, CDCl₃): δ 10.36 (s, 1H), 7.89 (s, 1H), 7.21 (s, 1H), 4.55-4.59 (m, 1H), 4.31 (t, 1H, J=1.6 Hz), 3.78-3.84 (m, 1H), 2.79-2.84 (m, 4H), 2.42-2.53 (m, 1H), 2.01-2.11 (m, 1H), 1.91-1.96 (m, 1H).

(e) Synthesis of 5-(methylsulfonyl)-2,3,4,5-tetrahydrothieno[3',2':4,5]benzo[1,2-b]oxepine-8-carboxylic acid The synthesis procedure of Intermediate 8-e was repeated except for using 8-chloro-5-(methylsulfonyl)-2,3,4,5-tetrahydrobenzo[b]oxepine-7-carbaldehyde (164.0 mg, 0.57 mmol) to obtain 5-(methylsulfonyl)-2,3,4,5-tetrahydrothieno[3',2':4,5]benzo[1,2-b]oxepine-8-carboxylic acid (116.0 mg, 62%) as a white solid.

LC/MS ESI (+): 341 (M+1)

¹H-NMR (400 MHz, DMSO-d₆): δ 13.48 (s, 1H), 8.07 (s, 1H), 8.05 (s, 1H), 7.73 (s, 1H), 4.80 (t, 1H, J=1.2 Hz), 4.33-4.39 (m, 1H), 3.75-3.80 (m, 1H), 2.89 (s, 3H), 2.50-2.53 (m, 1H) 2.18-2.27 (m, 1H), 2.06-2.14 (m, 1H), 1.75-1.88 (m, 1H)

Intermediate 10) Synthesis of 5-(methylsulfonyl)-5,6,7,8-tetrahydronaphtho[2,3-b]thiophene-2-carboxylic acid (a) Synthesis of 2-ethylhexyl 3-((5-bromo-2-formylphenyl)thio)propanoate To a solution of 4-bromo-2-fluorobenzaldehyde (3.0 g, 14.78 mmol) in DMF (73.9 ml) were added 2-Ethylhexyl 3-mercaptopropionate (3.7 ml, 16.26 mmol). The reaction mixture was stirred at 40° C. for 36 hours. The reaction mixture was purified by reversed-phase column chromatography (C18-silica gel, 0.1% formic acid in CH₃CN:0.1% formic acid in H₂O) to obtain 2-ethylhexyl 3-((5-bromo-2-formylphenyl)thio)propanoate (4.2 g, 71%) as a light brown oil.

LC/MS ESI (+): 401 (M+1)

¹H-NMR (400 MHz, CDCl₃): δ 10.28 (s, 1H), 7.70 (d, 1H, J=8.2 Hz), 7.57 (d, 1H, J=1.7 Hz), 7.46 (dd, 1H, J=8.2, 1.7 Hz), 4.03-4.05 (m, 2H), 3.24 (t, 2H, J=7.4 Hz), 2.72 (t, 2H, J=7.4 Hz), 1.32-1.40 (m, 3H), 1.26-1.30 (m, 6H), 0.90 (t, 6H, J=7.4 Hz)

(b) Synthesis of 2-ethylhexyl 3-((5-(4,4-diethoxybutyl)-2-(hydroxymethyl)phenyl)thio)propanoate A solution of 4,4-diethoxybut-1-ene (503.0 mg, 3.49 mmol) in 9-borabicyclo(3.3.1)nonane (7.7 ml, 3.84 mmol) was stirred for 1 hour and concentrated. The residue was dissolved in benzene (7.7 ml)/EtOH (3.9 ml). 2N Na₂CO₃ aqueous solution (35.0 ml, 6.98 mmol) and Pd(PPh₃)₄ (202.0 mg, 0.17 mmol) were added and the reaction mixture at 80° C. for 90 minutes. The reaction mixture was extracted with EtOAc. The organic extract was washed with brine, dried over anhydrous Na₂SO₄, filtered and concentrated. The residue was purified by normal phase column chromatography (EtOAc:n-Hex=1:15) to give 2-ethylhexyl 3-((5-(4,4-diethoxybutyl)-2-formylphenyl)thio)propanoate (695.0 mg, 85%) as crude. To a solution of 2-ethylhexyl 3-((5-(4,4-diethoxybutyl)-2-formylphenyl)thio)propanoate (610.0 mg, 1.31 mmol) in EtOH (6.5 ml) was added NaBH₄ (64.3 mg, 1.70 mmol). The reaction mixture was stirred for 30 minutes. NH₄Cl was added, and the resulting mixture was stirred for 15 minutes and filtered through celite. The filtrate was extracted with EtOAc. The organic extract was washed with brine, dried over anhydrous Na₂SO₄, and concentrated. The residue was purified by normal phase column chromatography (EtOAc:n-Hex=1:3) to give 2-ethylhexyl 3-((5-(4,4-diethoxybutyl)-2-(hydroxymethyl)phenyl)thio)propanoate (550.0 mg, 90%) as a colorless oil.

¹H-NMR (400 MHz, CDCl₃): δ 7.31 (d, 1H, J=7.7 Hz), 7.24 (d, 1H, J=1.7 Hz), 7.07 (d, 1H, J=7.7 Hz), 4.74 (d, 2H, J=3.3 Hz), 4.49 (t, 1H, J=5.2 Hz), 4.00-4.02 (m, 2H), 3.59-3.67 (m, 2H), 3.44-3.52 (m, 2H), 3.16 (t, 2H, J=7.2 Hz), 2.61 (t, 4H, J=7.1 Hz), 2.39 (brs, 1H), 1.65-1.68 (m, 4H), 1.51-1.57 (m, 2H), 1.26-1.37 (m, 2H), 1.26-1.31 (m, 4H), 1.20 (t, 6H, J=7.1 Hz), 0.89 (t, 6H, J=7.1 Hz)

(c) Synthesis of 2-ethylhexyl 3-((5-(methylsulfonyl)-3-((2,2,2-trifluoroacetoxy)methyl)-5,6,7,8-tetrahydronaphthalen-2-yl)thio)propanoate Sodium methanesulfinate (359.0 mg, 3.52 mmol) was dissolved in TFA (9.8 ml) and the reaction mixture was stirred for 10 minutes. After cooling to 0° C., a solution of 2-ethylhexyl 3-((5-(4,4-diethoxybutyl)-2-(hydroxymethyl)phenyl)thio)propanoate (550.0 mg, 1.17 mmol) in CH₂Cl₂ (1956.0 μl) was added dropwise and the reaction mixture was stirred at 23° C. for 1 hour. The reaction mixture was extracted with EtOAc, and the organic extract was washed with sat. NaHCO₃ aqueous solution and brine, dried over anhydrous Na₂SO₄, filtered and concentrated. The residue was purified by reversed-phase column chromatography (C18-silica gel, 0.1% formic acid in CH₃CN:0.1% formic acid in H₂O) to obtain 3-((5-(methylsulfonyl)-3-((2,2,2-trifluoroacetoxy)methyl)-5,6,7,8-tetrahydronaphthalen-2-yl)thio)propanoate (217.0 mg, 34%) as a colorless oil.

¹H-NMR (400 MHz, CDCl₃): δ 7.63 (s, 1H), 7.26 (s, 1H), 5.45 (q, 2H, J=20.8 Hz), 4.28 (t, 1H, J=5.1 Hz), 4.01-4.04 (m, 2H), 3.20 (t, 2H, J=7.5 Hz), 2.87-2.93 (m, 1H), 2.76-2.81 (m, 4H), 2.65 (t, 2H, J=7.6 Hz), 2.47-2.52 (m, 1H), 2.19-2.23 (m, 2H), 1.75-1.86 (m, 1H), 1.56-1.58 (m, 1H), 1.29-1.39 (m, 8H), 0.89 (t, 6H, J=7.4 Hz)

(d) Synthesis of tert-butyl 2-((3-(hydroxymethyl)-5-(methylsulfonyl)-5,6,7,8-tetrahydronaphthalen-2-yl)thio)acetate To a solution of 2-ethylhexyl 3-((5-(methylsulfonyl)-3-((2,2,2-trifluoroacetoxy)methyl)-5,6,7,8-tetrahydronaphthalen-2-yl)thio)propanoate (150.0 mg, 0.27 mmol) in DMF (2714.0 μl) was added 1M solution of potassium-t-butoxide in THF (543.0 μl, 0.54 mmol) at −60~−50° C. The reaction mixture was stirred for 10 minutes. tert-butyl 2-bromoacetate (42.1 μl, 0.29 mmol) was added at −60~−50° C. and the reaction mixture was stirred at room temperature for 1 hour. The reaction mixture was purified by reversed-phase column chromatography (C18-silica gel, 0.1% formic acid in CH₃CN:0.1% formic acid in H₂O) to obtain tert-butyl 2-((3-(hydroxymethyl)-5-(methylsulfonyl)-5,6,7,8-tetrahydronaphthalen-2-yl)thio)acetate (67.0 mg, 64%) as a white amorphous.

¹H-NMR (400 MHz, CDCl₃): δ 7.60 (s, 1H), 7.26 (s, 1H), 4.77 (q, 2H, J=32.7 Hz), 4.27 (t, 1H, J=5.9 Hz), 3.60 (s, 2H), 2.83-2.89 (m, 1H), 2.71-2.79 (m, 4H), 2.49-2.55 (m, 1H), 2.15-2.20 (m, 2H), 1.73-1.46 (m, 1H), 1.40 (s, 9H)

(e) Synthesis of tert-butyl 2-((3-formyl-5-(methylsulfonyl)-5,6,7,8-tetrahydronaphthalen-2-yl)thio)acetate To a solution of tert-butyl 2-((3-(hydroxymethyl)-5-(methylsulfonyl)-5,6,7,8-tetrahydronaphthalen-2-yl)thio)acetate (65.0 mg, 0.17 mmol) in CH₂Cl₂ (1682.0 μl) was added Dess-Martin periodinane (107.0 mg, 0.25 mmol). The reaction mixture was stirred at 24° C. for 1 hour. The reaction mixture was extracted with EtOAc. The organic extract was washed with brine, dried over anhydrous Na₂SO₄, filtered and concentrated to give tert-butyl 2-((3-formyl-5-(methylsulfonyl)-5,6,7,8-tetrahydronaphthalen-2-yl)thio)acetate (71.0 mg, 110%) as crude. The crude was used the next step without purification.

¹H-NMR (400 MHz, CDCl₃): δ 10.23 (s, 1H), 8.04 (s, 1H), 7.29 (s, 1H), 4.31-4.34 (m, 1H), 3.63 (s, 2H), 2.92-2.99 (m, 1H), 2.80-2.87 (m, 4H), 2.52-2.57 (m, 1H), 2.22-2.25 (m, 2H), 1.77-1.82 (m, 1H), 1.44 (s, 9H)

(f) Synthesis of tert-butyl 5-(methylsulfonyl)-5,6,7,8-tetrahydronaphtho[2,3-b]thiophene-2-carboxylate To a solution of tert-butyl 2-((3-formyl-5-(methylsulfonyl)-5,6,7,8-tetrahydronaphthalen-2-yl)thio)acetate (67.0 mg, 0.17 mmol) in DMF (1742.0 μl) was added Cs₂CO₃ (85.0 mg, 0.26 mmol). The reaction mixture was stirred at 80° C. for 1 hour. The reaction mixture was extracted with EtOAc. The organic extract was washed with brine, dried over anhydrous Na₂SO₄, filtered and concentrated to give tert-butyl 5-(methylsulfonyl)-5,6,7,8-tetrahydronaphtho[2,3-b]thiophene-2-carboxylate (65.0 mg, 102%) as crude. The crude was used the next step without purification.

¹H-NMR (400 MHz, CDCl₃): δ 8.11 (s, 1H), 7.93 (s, 1H), 7.66 (s, 1H), 4.43-4.46 (m, 1H), 3.00-3.08 (m, 1H), 2.90-2.98 (m, 4H), 2.53-2.59 (m, 1H), 2.31-2.35 (m, 1H), 2.17-2.19 (m, 1H), 1.71-1.83 (m, 1H), 1.61 (s, 9H)

(g) Synthesis of 5-(methylsulfonyl)-5,6,7,8-tetrahydronaphtho[2,3-b]thiophene-2-carboxylic acid To a solution of tert-butyl 5-(methylsulfonyl)-5,6,7,8-tetrahydronaphtho[2,3-b]thiophene-2-carboxylate (65.0 mg, 0.18 mmol) in CH₂Cl₂ (0.5 ml) was added TFA (0.5 ml, 6.53 mmol). The reaction mixture was stirred at 24° C. for 30 minutes. The reaction mixture was purified by reversed-phase column chromatography (C18-silica gel, 0.1% formic acid in CH₃CN:0.1% formic acid in H₂O) to obtain 5-(methylsulfonyl)-5,6,7,8-tetrahydronaphtho[2,3-b]thiophene-2-carboxylic acid (30.0 mg, 55%) as a white amorphous.

LC/MS ESI (−): 309 (M−1)

¹H-NMR (400 MHz, DMSO-d₆): δ 8.13 (s, 1H), 8.10 (s, 1H), 7.90 (s, 1H), 4.80-4.82 (m, 1H), 3.05 (s, 3H), 2.91-3.02 (m, 2H), 2.48-2.51 (m, 1H), 2.19-2.23 (m, 2H), 1.67-1.72 (m, 1H)

Intermediate 11) Synthesis of 4-methyl-4-(methylsulfonyl)-3,4-dihydro-2H-thieno[3,2-g]chromene-7-carboxylic acid (a) Synthesis of methyl 4-methyl-4-(methylsulfonyl)-3,4-dihydro-2H-thieno[3,2-g]chromene-7-carboxylate To a suspension of methyl 4-(methylsulfonyl)-3,4-dihydro-2H-thieno[3,2-g]chromene-7-carboxylate (50.0 mg, 0.15 mmol) in THF (1.0 ml)/CH₃CN (1.0 ml) was added NaH (30.6 mg, 0.77 mmol). After 1 hour, CH₃I (0.1 ml, 1.53 mmol) was added and the reaction mixture was stirred for 3 days. The reaction mixture was purified by reversed-phase column chromatography (C18-silica gel, 0.1% formic acid in CH₃CN:0.1% formic acid in H₂O) to obtain methyl 4-methyl-4-(methylsulfonyl)-3,4-dihydro-2H-thieno[3,2-g]chromene-7-carboxylate (29.0 mg, 56%) as an off-white amorphous.

LC/MS ESI (+): 341 (M+1)

¹H-NMR (400 MHz, DMSO-$d_6$): δ 8.29 (s, 1H), 8.16 (s, 1H), 7.56 (s, 1H), 4.49-4.56 (m, 1H), 4.20-4.26 (m, 1H), 3.88 (s, 3H), 3.00 (s, 3H), 2.61-2.68 (m, 1H), 2.16-2.23 (m, 1H), 1.83 (s, 3H)

(b) Synthesis of 4-methyl-4-(methylsulfonyl)-3,4-dihydro-2H-thieno[3,2-g]chromene-7-carboxylic acid To a suspension of methyl 4-methyl-4-(methylsulfonyl)-3,4-dihydro-2H-thieno[3,2-g]chromene-7-carboxylate (27.0 mg, 0.08 mmol) in THF (529.0 μl)/H$_2$O (264.0 μl) was added LiOHH$_2$O (33.3 mg, 0.79 mmol). The reaction mixture was stirred at 60° C. for 1 hour. The reaction mixture was concentrated and the residue was purified by reversed-phase column chromatography (C18-silica gel, 0.1% formic acid in CH$_3$CN:0.1% formic acid in H$_2$O) to obtain 4-methyl-4-(methylsulfonyl)-3,4-dihydro-2H-thieno[3,2-g]chromene-7-carboxylic acid (20.0 mg, 77%) as a white amorphous.

LC/MS ESI (−): 325 (M−1)
¹H-NMR (400 MHz, DMSO-$d_6$): δ 8.22 (s, 1H), 7.96 (s, 1H), 7.49 (s, 1H), 4.47-4.52 (m, 1H), 4.18-4.22 (m, 1H), 2.97 (s, 3H), 2.59-2.67 (m, 1H), 2.13-2.20 (m, 1H), 1.81 (s, 3H)

Intermediate 12) Synthesis of 5-(methylsulfonyl)-5,8-dihydro-6H-thieno[3,2-g]isochromene-2-carboxylic acid (a) Synthesis of methyl 2-bromo-4-(bromomethyl)benzoate 2-Bromo-4-methylbenzoate (4.6 g, 20.08 mmol) was dissolved in anhydrous 1,2-dichloroethane (60.0 ml), and N-bromosuccinimide (4.3 g, 24.10 mmol) and AIBN (0.3 g, 2.01 mmol) were added at room temperature. The mixture was refluxed at 90° C. for 1 hour, followed by cooling to room temperature and extracted with CH$_2$Cl$_2$. The organic extract was washed with brine, dried over anhydrous Na$_2$SO$_4$, and concentrated under a reduced pressure. The residue was purified by reversed-phase column chromatography (C18-silica gel, 0.1% formic acid in CH$_3$CN:0.1% formic acid in H$_2$O) to obtain methyl 2-bromo-4-(bromomethyl)benzoate (3.0 g, 48%) as a colorless liquid.

LC/MS ESI (+): 309 (M+1)
¹H-NMR (400 MHz, CDCl$_3$): δ 7.78 (d, 1H, J=8.0 Hz), 7.69 (d, 1H, J=1.6 Hz), 7.38 (dd, 1H, J=8.0, 1.6 Hz), 4.42 (s, 2H), 3.94 (s, 3H)

(b) Synthesis of methyl 2-bromo-4-((2,2-diethoxyethoxy)methyl)benzoate

Glycolaldehyde diethyl acetal (1.6 ml, 12.14 mmol) was dissolved in anhydrous THF (50.0 ml), and NaH (0.5 g, 13.25 mmol) was added at 0° C. The mixture was stirred at 0° C. for 30 minutes. Methyl 2-bromo-4-(bromomethyl)benzoate (3.4 g, 11.04 mmol) in THF (50.0 ml) was added at 0° C. The mixture was stirred at 0° C. for 3 hours and extracted with EtOAc. The organic extract was washed with water, dried over anhydrous Na$_2$SO$_4$, and concentrated under a reduced pressure. The residue was purified by flash column chromatography (silica gel, n-Hex:EtOAc=9:1) to obtain methyl 2-bromo-4-((2,2-diethoxyethoxy)methyl)benzoate (1.7 g, 42%) as a colorless liquid.

¹H-NMR (400 MHz, CDCl$_3$): δ 7.78 (d, 1H, J=8.0 Hz), 7.66 (d, 1H, J=1.2 Hz), 7.31-7.34 (m, 1H), 4.67 (t, 1H, J=10.4, 5.2 Hz), 4.59 (s, 2H), 3.93 (s, 3H), 3.68-3.75 (m, 2H), 3.53-3.62 (m, 4H), 1.23 (t, 6H, J=14.0, 6.8 Hz)

(c) Synthesis of 4-((2,2-diethoxyethoxy)methyl)-2-(methylthio)benzoic acid

Methyl 2-bromo-4-((2,2-diethoxyethoxy)methyl)benzoate (480.0 mg, 1.33 mmol) was dissolved in DMF (4.0 ml), and sodium methanethiolate (466 mg, 6.64 mmol) was added at room temperature. The mixture was stirred at 80° C. for 15 hours, followed by cooling to room temperature and extracted with EtOAc. The organic extract was washed with brine, dried over anhydrous Na$_2$SO$_4$ and concentrated under a reduced pressure. The residue was purified by reversed-phase column chromatography (C18-silica gel, 0.1% formic acid in CH$_3$CN:0.1% formic acid in H$_2$O) to obtain 4-((2,2-diethoxyethoxy)methyl)-2-(methylthio)benzoic acid (380.0 mg, 91%) as a colorless liquid LC/MS ESI (−): 313 (M−1)
¹H-NMR (400 MHz, CDCl$_3$): δ 8.10 (d, 1H, J=8.0 Hz), 7.30 (s, 1H), 7.14 (dd, 1H, J=8.0, 0.8 Hz), 4.70 (t, 1H, J=10.4, 5.2 Hz), 4.65 (s, 2H), 3.68-3.76 (m, 2H), 3.55-3.63 (m, 4H), 2.48 (s, 3H), 1.24 (t, 6H, J=14.0, 6.8 Hz)

(d) Synthesis of (4-((2,2-diethoxyethoxy)methyl)-2-(methylthio)phenyl)methanol 4-((2,2-diethoxyethoxy)methyl)-2-(methylthio)benzoic acid (380.0 mg, 1.21 mmol) was dissolved in THF (12.0 ml), and 1.0M solution of LiAlH4 in THF (1.2 ml, 1.20 mmol) was added at room temperature. The mixture was stirred at room temperature for 1 hour and H$_2$O was added at 0° C. The reaction mixture was filtered through Celite and extracted with CH$_2$Cl$_2$. The organic extract was washed with brine, dried over anhydrous Na$_2$SO$_4$, and concentrated under a reduced pressure. The residue was purified by reversed-phase column chromatography (C18-silica gel, 0.1% formic acid in CH$_3$CN:0.1% formic acid in H$_2$O) to obtain (4-((2,2-diethoxyethoxy)methyl)-2-(methylthio)phenyl)methanol (280.0 mg, 77%) as a colorless liquid.

¹H-NMR (400 MHz, CDCl$_3$): δ 7.34 (d, 1H, J=8.0 Hz), 7.26 (m, 1H), 7.12-7.14 (m, 1H), 4.75 (brs, 2H), 4.66 (t, 1H, J=10.4, 5.2 Hz), 4.58 (s, 2H), 3.66-3.74 (m, 2H), 3.51-3.61 (m, 4H), 2.50 (s, 3H), 2.08 (brs, 1H), 1.22 (t, 6H, J=14.0, 7.2 Hz)

(e) Synthesis of (4-(methylsulfonyl)-7-(methylthio)isochroman-6-yl)methanol

Sodium methanesulfinate (285.0 mg, 2.80 mmol) was dissolved in TFA (7.5 ml) and stirred at room temperature for 30 minutes. (4-((2,2-diethoxyethoxy)methyl)-2-(methylthio)phenyl)methanol (280.0 mg, 0.93 mmol) in CH$_2$Cl$_2$ (1.5 ml) was slowly added at room temperature. The mixture was stirred at room temperature for 30 minutes and extracted with EtOAc. The organic extract was washed with brine, dried over anhydrous Na$_2$SO$_4$ and concentrated under a reduced pressure. The mixture was dissolved in THF (4.0 ml)/MeOH (1.0 ml)/H$_2$O (1.0 ml) and LiOHH$_2$O (223.0 mg, 932.00 mmol) was added at room temperature. The mixture was stirred at room temperature for 30 minutes and extracted with EtOAc. The organic extract was washed with brine, dried over anhydrous Na$_2$SO$_4$, filtered and concentrated to obtain (4-(methylsulfonyl)-7-(methylthio)isochroman-6-yl)methanol (208.0 mg, 77%)%) as a colorless liquid.

LC/MS ESI (−): 287 (M−1)

¹H-NMR (400 MHz, CDCl₃): δ 7.66 (s, 1H), 6.91 (s, 1H), 4.86-4.91 (m, 2H), 4.70-4.80 (m, 3H), 3.97-4.01 (m, 1H), 3.87-3.88 (m, 1H), 2.67 (s, 3H), 2.50 (s, 3H)

(f) Synthesis of 4-(methylsulfonyl)-7-(methylthio) isochromane-6-carbaldehyde (4-(Methylsulfonyl)-7-(methylthio)isochroman-6-yl) methanol (208.0 mg, 0.72 mmol) was dissolved in CH₂Cl₂ (7.0 ml) and Dess-Martin Periodinane (398.0 mg, 0.94 mmol) was added at room temperature. The mixture was stirred at room temperature for 30 minutes and extracted with CH₂Cl₂. The organic extract was washed with brine, dried over anhydrous Na₂SO₄ and concentrated under a reduced pressure. The residue was purified by flash column chromatography (silica gel, n-Hex:EtOAc=1:1) to obtain 4-(methylsulfonyl)-7-(methylthio)isochromane-6-carbaldehyde (150.0 mg, 72%) as a colorless liquid.

LC/MS ESI (+): 287 (M+1)

¹H-NMR (400 MHz, CDCl₃): δ 10.16 (s, 1H), 8.10 (s, 1H), 7.00 (s, 1H), 4.93-4.97 (m, 2H), 4.80-4.84 (m, 1H), 4.02-4.06 (m, 1H), 3.94-3.95 (m, 1H), 2.69 (s, 3H), 2.48 (s, 3H)

(g) Synthesis of 5-(methylsulfonyl)-5,8-dihydro-6H-thieno[3,2-g]isochromene-2-carboxylic acid A mixture of 4-(Methylsulfonyl)-7-(methylthio)isochroman-6-carbaldehyde (150.0 mg, 0.52 mmol), magnesium oxide (21.1 mg, 0.52 mmol) and 2-chloroacetic acid (990.0 mg, 10.48 mmol) was stirred at 110° C. for 16 hours and extracted with EtOAc. The organic extract was washed with brine, dried over anhydrous Na₂SO₄, and concentrated under a reduced pressure. The residue was purified by reversed-phase column chromatography (C18-silica gel, 0.1% formic acid in CH₃CN:0.1% formic acid in H₂O) to obtain 5-(methylsulfonyl)-5,8-dihydro-6H-thieno[3,2-g]isochromene-2-carboxylic acid (50.0 mg, 30%) as a white solid.

LC/MS ESI (−): 311 (M−1)

¹H-NMR (400 MHz, CDCl₃): δ 8.26 (s, 1H), 8.14 (s, 1H), 7.64 (s, 1H), 4.91-5.08 (m, 3H), 4.07-4.11 (m, 2H), 2.66 (s, 3H)

Intermediate 13) Synthesis of 4-fluoro-4-(methylsulfonyl)-3,4-dihydro-2H-thieno[3,2-g]chromene-7-carboxylic acid (a) Synthesis of 7-chloro-4-fluoro-6-methyl-4-(methylsulfonyl)chromane 7-chloro-6-methyl-4-(methylsulfonyl)chromane (850.0 mg, 3.26 mmol) was dissolved in THF (30.0 mL), and LDA (2.6 mL, 3.91 mmol) was slowly added at −78° C. and stirred for 0.5 hour. NFS (2.3 g, 7.17 mmol) was added, followed by stirring at −78° C. for 3 hours. The reaction was quenched with H₂O, and the reaction mixture was extracted with EtOAc. The organic extract was washed with brine, dried over anhydrous Na₂SO₄, and concentrated under a reduced pressure. The residue was purified by flash column chromatography (silica gel, n-Hex:EtOAc=85:15) to obtain 7-chloro-4-fluoro-6-methyl-4-(methylsulfonyl)chromane (600.0 mg, 66%) as a a white solid ¹H-NMR (400 MHz, DMSO-d₆): δ 7.53 (s, 1H), 6.97 (s, 1H), 4.59-4.65 (m, 1H), 4.28-4.35 (m, 1H), 3.05 (s, 3H), 2.72-2.80 (m, 1H), 2.49-2.56 (m, 1H), 2.33 (s, 3H)

(b) Synthesis of 6-(bromomethyl)-7-chloro-4-fluoro-4-(methylsulfonyl)chromane

The synthesis procedure of Intermediate 8-c was repeated except for using 7-chloro-4-fluoro-6-methyl-4-(methylsulfonyl)chromane (500.0 mg, 1.79 mmol) to obtain 6-(bromomethyl)-7-chloro-4-fluoro-4-(methylsulfonyl)chromane (520.0 mg, 81%).

¹H-NMR (400 MHz, DMSO-d₆): δ 7.75 (s, 1H), 7.01 (s, 1H), 4.67-4.68 (m, 1H), 4.56 (q, 2H, J=10.4, 21.1 Hz), 4.35-4.41 (m, 1H), 3.06 (s, 3H), 2.74-2.82 (m, 1H), 2.49-2.60 (m, 1H)

(c) Synthesis of 6-(bromomethyl)-7-chloro-4-fluoro-4-(methylsulfonyl)chromane

The synthesis procedure of Intermediate 8-d was repeated except for using 6-(bromomethyl)-7-chloro-4-fluoro-4-(methylsulfonyl)chromane (400.0 mg, 1.11 mmol) to obtain 7-chloro-4-fluoro-4-(methylsulfonyl)chromane-6-carbaldehyde (225.0 mg, 68%).

LC/MS ESI (+): 293 (M+1)

¹H-NMR (400 MHz, DMSO-d₆): δ 10.32 (s, 1H), 8.20 (s, 1H), 7.04 (s, 1H), 4.73-4.80 (m, 1H), 4.49-4.55 (m, 1H), 3.09 (s, 3H), 2.86-2.93 (m, 1H), 2.47-2.59 (m, 1H)

(d) Synthesis of 4-fluoro-4-(methylsulfonyl)-3,4-dihydro-2H-thieno[3,2-g]chromene-7-carboxylic acid 7-chloro-4-fluoro-4-(methylsulfonyl)chromane-6-carbaldehyde (210.0 mg, 0.71 mmol) was dissolved in anhydrous DMF (7.1 mL), and methyl 2-mercaptoacetate (114.0 mg, 1.07 mmol) and Cs₂CO₃ (514.0 mg, 1.57 mmol) were added, followed by heating at 80° C. for 2 hours. The reaction mixture was cooled to room temperature and extracted with EtOAc. The organic extract was washed with brine, dried over anhydrous Na₂SO₄, concentrated under reduced pressure. The residue was purified by reversed-phase column chromatography (C18-silica gel, 0.1% formic acid in CH₃CN:0.1% formic acid in H₂O) to obtain 4-fluoro-4-(methylsulfonyl)-3,4-dihydro-2H-thieno[3,2-g]chromene-7-carboxylic acid (72.0 mg, 30%) as a yellow solid

LC/MS ESI (−): 329 (M−1)

¹H-NMR (400 MHz, DMSO-d₆): δ 13.47 (s, 1H), 8.32 (s, 1H), 8.13 (s, 1H), 7.66 (s, 1H), 4.53-4.56 (m, 1H), 4.40-4.44 (m, 2H), 2.95-2.97 (m, 2H), 2.64-2.67 (m, 2H)

Intermediate 14) Synthesis of 8,8-difluoro-5-(methylsulfonyl)-5,6,7,8-tetrahydronaphtho[2,3-b]thiophene-2-carboxylic acid (a) Synthesis of 7-chloro-6-methyl-4-(methylsulfonyl)-3,4-dihydronaphthalen-1(2H)-one To a solution of 6-chloro-7-methyl-1-(methylsulfonyl)-1,2,3,4-tetrahydronaphthalene (700.0 mg, 2.71 mmol) in acetic anhydride (5114.0 μl, 54.10 mmol) was added chromium oxide(VI) (812.0 mg, 8.12 mmol) at 0° C. The reaction mixture was stirred at 0° C. for 2 hours. The residue was purified by reversed-phase column chromatography (C18-silica gel, 0.1% formic acid in CH₃CN:0.1% formic acid in H₂O) to obtain 7-chloro-6-methyl-4-(methylsulfonyl)-3,4-dihydronaphthalen-1(2H)-one (430.0 mg, 58%) as a white amorphous.

LC/MS ESI (+): 273 (M+1)

¹H-NMR (400 MHz, CDCl₃): δ 8.12 (s, 1H), 7.40 (s, 1H), 4.31-4.33 (m, 1H), 3.16-3.26 (m, 1H), 2.93 (s, 3H), 2.86-2.91 (m, 1H), 2.64-2.71 (m, 1H), 2.51-2.60 (m, 1H), 2.47 (s, 3H)

(b) Synthesis of 7-chloro-1,1-difluoro-6-methyl-4-(methylsulfonyl)-1,2,3,4-tetrahydronaphthalene A suspension of 7-chloro-6-methyl-4-(methylsulfonyl)-3,4-dihydronaphthalen-1(2H)-one (430.0 mg, 1.58 mmol) in DAST (2.0 ml, 15.14 mmol) was stirred at 65° C. overnight. The reaction mixture was purified by reversed-phase column chromatography (C18-silica gel, 0.1% formic acid in CH₃CN:0.1% formic acid in H₂O) to obtain 7-chloro-1,1-difluoro-6-methyl-4-(methylsulfonyl)-1,2,3,4-tetrahydronaphthalene (186.0 mg, 40%) as a white amorphous.
LC/MS ESI (−): 293 (M−1)
¹H-NMR (400 MHz, CDCl₃): δ 7.77 (s, 1H), 7.60 (s, 1H), 4.22-4.26 (m, 1H), 2.77 (s, 3H), 2.65-2.73 (m, 1H), 2.51-2.62 (m, 2H), 2.43 (s, 3H), 2.23-2.35 (m, 1H)

(c) Synthesis of 6-(bromomethyl)-7-chloro-1,1-difluoro-4-(methylsulfonyl)-1,2,3,4-tetrahydronaphthalene To a solution of 7-chloro-1,1-difluoro-6-methyl-4-(methylsulfonyl)-1,2,3,4-tetrahydronaphthalene (150.0 mg, 0.51 mmol) and N-bromosuccinimide (109.0 mg, 0.61 mmol) in 1,2-dichloroethane (2545.0 μl) was added AIBN (8.4 mg, 0.05 mmol). The reaction mixture was stirred at 80° C. for 1 hour. The reaction mixture was purified by flash column chromatography (silica gel, n-Hex:EtOAc=5:1) to obtain 6-(bromomethyl)-7-chloro-1,1-difluoro-4-(methylsulfonyl)-1,2,3,4-tetrahydronaphthalene (105.0 mg, 55%) as a white amorphous.
LC/MS ESI (−): 371 (M−1)
¹H-NMR (400 MHz, CDCl₃): δ 7.85 (s, 2H), 4.55-4.64 (m, 2H), 4.25-4.29 (m, 1H), 2.82 (s, 3H), 2.68-2.73 (m, 1H), 2.56-2.59 (m, 2H), 2.27-2.34 (m, 1H)

(d) Synthesis of 3-chloro-5,5-difluoro-8-(methylsulfonyl)-5,6,7,8-tetrahydronaphthalene-2-carbaldehyde A suspension of 6-(bromomethyl)-7-chloro-1,1-difluoro-4-(methylsulfonyl)-1,2,3,4-tetrahydronaphthalene (105.0 mg, 0.28 mmol), N-methyl morpholine-N-oxide (49.4 mg, 0.42 mmol) and molecular sieve (4 Å) in CH₃CN (2.8 ml) was stirred at 25° C. for 1 hour. The reaction mixture was purified by reversed-phase column chromatography (C18-silica gel, 0.1% formic acid in CH₃CN:0.1% formic acid in H₂O) to obtain 3-chloro-5,5-difluoro-8-(methylsulfonyl)-5,6,7,8-tetrahydronaphthalene-2-carbaldehyde (60.0 mg, 69%) as a light brown amorphous.
LC/MS ESI (−): 307 (M−1)
¹H-NMR (400 MHz, CDCl₃): δ 10.49 (s, 1H), 8.15 (s, 1H), 7.92 (s, 1H), 4.30-4.33 (m, 1H), 2.92 (s, 3H), 2.83-2.87 (m, 1H), 2.68-2.75 (m, 1H), 2.47-2.57 (m, 1H), 2.34-2.39 (m, 1H)

(e) Synthesis of 8,8-difluoro-5-(methylsulfonyl)-5,6,7,8-tetrahydronaphtho[2,3-b]thiophene-2-carboxylic acid To a solution of 3-chloro-5,5-difluoro-8-(methylsulfonyl)-5,6,7,8-tetrahydronaphthalene-2-carbaldehyde (58.0 mg, 0.19 mmol) and Cs₂CO₃ (122.0 mg, 0.38 mmol) in DMF (939.0 μl) was added methyl thioglycollate (18.5 μl, 0.21 mmol). The reaction mixture was stirred at 80° C. for 1 hour. The reaction mixture was cooled to 60° C. and LiOHH₂O (79.0 mg, 1.88 mmol) was added and stirred for 1 hour. The reaction mixture was purified by reversed-phase column chromatography (C18-silica gel, 0.1% formic acid in CH₃CN:0.1% formic acid in H₂O) to obtain 8,8-difluoro-5-(methylsulfonyl)-5,6,7,8-tetrahydronaphtho[2,3-b]thiophene-2-carboxylic acid (33.0 mg, 51%) as an off-white amorphous.
LC/MS ESI (−): 345 (M−1)
¹H-NMR (400 MHz, DMS-d6): δ 8.48 (s, 1H), 8.18 (s, 1H), 8.13 (s, 1H), 4.89-4.90 (m, 1H), 3.17 (s, 3H), 2.66-2.73 (m, 2H), 2.32-2.42 (m, 2H)

Intermediate 15) Synthesis of 4-(1H-pyrazol-1-yl)-3,4-dihydro-2H-thieno[3,2-g]chromene-7-carboxylic acid (a) Synthesis of 3-(3-chloro-4-methylphenoxy)propanoic acid To a solution of 2-chloro-4-(3,3-diethoxypropoxy)-1-methylbenzene (3.0 g, 11.00 mmol) in THF (27.5 ml)/H₂O (27.5 ml) was added Oxone (10.1 g, 33.00 mmol). The reaction mixture was stirred at 25° C. overnight and filtered. The filtrate was extracted with EtOAc. The organic extract was washed with brine, dried over anhydrous Na₂SO₄, filtered and concentrated to give 3-(3-chloro-4-methylphenoxy)propanoic acid (2.4 g, 100%) as a white amorphous.
LC/MS ESI (−): 213 (M−1)
¹H-NMR (400 MHz, CDCl₃): δ 7.11 (d, 1H, J=8.4 Hz), 6.92 (d, 1H, J=2.5 Hz), 6.73 (dd, 1H, J=8.4, 2.4 Hz), 4.21 (t, 2H, J=6.2 Hz), 2.84 (t, 2H, J=6.2 Hz), 2.29 (s, 3H)

(b) Synthesis of 7-chloro-6-methylchroman-4-one 3-(3-chloro-4-methylphenoxy)propanoic acid (2.4 g, 10.95 mmol) was dissolved in trifluoromethansulfonic acid (4.8 ml, 54.70 mmol) and the reaction mixture was stirred for 2.5 hours. Ice chip was added slowly and the resulting mixture was extracted with EtOAc. The organic extract was washed with brine, dried over anhydrous Na₂SO₄, filtered and concentrated. The residue was purified by reversed-phase column chromatography (C18-silica gel, 0.1% formic acid in CH₃CN:0.1% formic acid in H₂O) to obtain 7-chloro-6-methylchroman-4-one (795.0 mg, 37%) as a white amorphous.
LC/MS ESI (+): 197 (M+1)
¹H-NMR (400 MHz, CDCl₃): δ 7.74 (s, 1H), 7.01 (s, 1H), 4.52 (t, 2H, J=6.5 Hz), 2.84 (t, 2H, J=6.5 Hz), 2.32 (s, 3H)

(c) Synthesis of 6-(bromomethyl)-7-chlorochroman-4-one

The synthesis procedure of Intermediate 8-c was repeated except for using 7-chloro-6-methylchroman-4-one (950.0 mg, 4.83 mmol) to obtain 6-(bromomethyl)-7-chlorochroman-4-one (1.4 g, 87%) as an ivory solid.
LC/MS ESI (+): 275 (M+1)
¹H-NMR (400 MHz, CDCl₃): δ 7.97 (s, 1H), 7.10 (s, 1H), 4.54-4.58 (m, 4H), 2.82 (t, 2H, J=6.5 Hz)

(d) Synthesis of 7-chloro-4-oxochromane-6-carbaldehyde

The synthesis procedure of Intermediate 8-d was repeated except for using 6-(bromomethyl)-7-chlorochroman-4-one (1.3 g, 4.72 mmol) to obtain 7-chloro-4-oxochromane-6-carbaldehyde (660.0 mg, 66%) as a white solid.

LC/MS ESI (+): 211 (M+1)

$^1$H-NMR (400 MHz, CDCl$_3$): δ 10.34 (s, 1H), 8.50 (s, 1H), 7.10 (s, 1H), 4.64 (t, 2H, J=6.5 Hz), 2.87 (t, 2H, J=6.5 Hz)

(e) Synthesis of methyl 4-oxo-3,4-dihydro-2H-thieno[3,2-g]chromene-7-carboxylate The synthesis procedure of Intermediate 8-d was repeated except for using 7-chloro-4-oxochromane-6-carbaldehyde (660.0 mg, 3.13 mmol) to obtain 4-oxo-3,4-dihydro-2H-thieno[3,2-g]chromene-7-carboxylate (580.0 mg, 71%) as an off white solid.

LC/MS ESI (+): 263 (M+1)

$^1$H-NMR (400 MHz, CDCl$_3$): δ 8.49 (s, 1H), 8.26 (s, 1H), 7.74 (s, 1H), 4.59 (t, 2H, J=6.4 Hz), 3.87 (s, 3H), 2.87 (t, 2H, J=6.4 Hz)

(f) Synthesis of methyl 4-hydroxy-3,4-dihydro-2H-thieno[3,2-g]chromene-7-carboxylate To a solution of methyl 4-oxo-3,4-dihydro-2H-thieno[3,2-g]chromene-7-carboxylate (810.0 mg, 3.09 mmol) in EtOH (15.0 ml) was added NaBH$_4$ (140.0 mg, 3.71 mmol). The reaction mixture was stirred at 26° C. for 2 hours. H$_2$O was added and insoluble white solid was filtered to give methyl 4-hydroxy-3,4-dihydro-2H-thieno[3,2-g]chromene-7-carboxylate (665.0 mg, 81%) as a white solid.

LC/MS ESI (+): 265 (M+1)

$^1$H-NMR (400 MHz, DMSO-d$_6$): δ 8.11 (s, 1H), 7.79 (s, 1H), 7.40 (s, 1H), 5.55 (m, 1H), 4.75-4.79 (m, 1H), 4.23-4.33 (m, 2H), 3.85 (s, 3H), 2.02-2.09 (m, 1H), 1.88-1.94 (m, 1H)

(g) Synthesis of methyl 4-chloro-3,4-dihydro-2H-thieno[3,2-g]chromene-7-carboxylate To a solution of methyl 4-hydroxy-3,4-dihydro-2H-thieno[3,2-g]chromene-7-carboxylate (200.0 mg, 0.76 mmol) in toluene (3784.0 μl) was added SOCl$_2$ (110.0 μl, 1.51 mmol). The reaction mixture was stirred at 60° C. for 2 hours. After cooling, the reaction mixture was concentrated to give methyl 4-chloro-3,4-dihydro-2H-thieno[3,2-g]chromene-7-carboxylate (210.0 mg, 98%) as a white amorphous without purification.

$^1$H-NMR (400 MHz, DMSO-d$_6$): δ 8.13 (s, 1H), 8.02 (s, 1H), 7.51 (s, 1H), 5.72 (t, 1H, J=3.4 Hz), 4.36-4.46 (m, 2H), 3.86 (s, 3H), 2.42-2.48 (m, 1H), 2.26-2.31 (m, 1H)

(h) Synthesis of methyl 4-(1H-pyrazol-1-yl)-3,4-dihydro-2H-thieno[3,2-g]chromene-7-carboxylate A solution of methyl 4-chloro-3,4-dihydro-2H-thieno[3,2-g]chromene-7-carboxylate (80.0 mg, 0.28 mmol), pyrazole (57.8 mg, 0.85 mmol) and K$_2$CO$_3$ (117.0 mg, 0.85 mmol) in DMA (2829.0 μl) was stirred at 60° C. for 1 hour and then stirred at 80° C. After 1 hour, the reaction mixture was stirred at 100° C. for 1 hour. The reaction mixture was purified by reversed-phase column chromatography (C18-silica gel, 0.1% formic acid in CH$_3$CN:0.1% formic acid in H$_2$O) to obtain methyl 4-(1H-pyrazol-1-yl)-3,4-dihydro-2H-thieno[3,2-g]chromene-7-carboxylate (26.0 mg, 29%) as a white amorphous.

LC/MS ESI (+): 315 (M+1)

$^1$H-NMR (400 MHz, CDCl3): δ 7.87 (s, 1H), 7.61 (d, 1H, J=1.5 Hz), 7.51 (s, 1H), 7.37 (s, 1H), 7.22 (d, 1H, J=2.1 Hz), 6.25-6.26 (m, 1H), 5.72 (t, 1H, J=5.1 Hz), 4.31-4.37 (m, 1H), 4.15-4.21 (m, 1H), 3.92 (s, 3H), 2.56-2.64 (m, 1H), 2.40-2.48 (m, 1H)

(i) Synthesis of 4-(1H-pyrazol-1-yl)-3,4-dihydro-2H-thieno[3,2-g]chromene-7-carboxylic acid To a suspension of methyl 4-(1H-pyrazol-1-yl)-3,4-dihydro-2H-thieno[3,2-g]chromene-7-carboxylate (25.0 mg, 0.08 mmol) in THF (530.0 μl)/H$_2$O (265.0 μl) was added LiOHH$_2$O (33.4 mg, 0.78 mmol). The reaction mixture was stirred at 60° C. for 1 hour. The reaction mixture was cooled to room temperature. 1N-HCl was added and insoluble white solid was filtered to give 4-(1H-pyrazol-1-yl)-3,4-dihydro-2H-thieno[3,2-g]chromene-7-carboxylic acid (17.0 mg, 71%) as a white solid.

LC/MS ESI (−): 299 (M−1)

Intermediate 16) Synthesis of 4-(2-oxopyrrolidin-1-yl)-3,4-dihydro-2H-thieno[3,2-g]chromene-7-carboxylic acid To a solution of 2-Pyrrolidinone (64.5 μl, 0.85 mmol) in DMA (4.2 ml) was added NaH (33.9 mg, 0.85 mmol). The reaction mixture was stirred at 100° C. for 30 minutes. methyl 4-chloro-3,4-dihydro-2H-thieno[3,2-g]chromene-7-carboxylate (120.0 mg, 0.42 mmol) was added and stirred for 1 hour. The reaction mixture was cooled to 80° C. LiOHH$_2$O (53.4 mg, 1.27 mmol) was added and stirred for 1 hour. The reaction mixture was purified by reversed-phase column chromatography (C18-silica gel, 0.1% formic acid in CH$_3$CN:0.1% formic acid in H$_2$O) to obtain 4-(2-oxopyrrolidin-1-yl)-3,4-dihydro-2H-thieno[3,2-g]chromene-7-carboxylic acid (13.0 mg, 10%) as a white amorphous.

LC/MS ESI (+): 318 (M+1)

$^1$H-NMR (400 MHz, DMS-d6): δ 7.93 (s, 1H), 7.57 (s, 1H), 7.42 (s, 1H), 5.41-5.45 (m, 1H), 4.27-4.40 (m, 2H), 3.23-3.32 (m, 1H), 2.95-3.01 (m, 1H), 2.36-2.43 (m, 2H), 2.10-2.19 (m, 1H), 1.90-2.01 (m, 3H)

Intermediate 17) Synthesis of 4-cyano-3,4-dihydro-2H-thieno[3,2-g]chromene-7-carboxylic acid (a) Synthesis of methyl 4-bromo-3,4-dihydro-2H-thieno[3,2-g]chromene-7-carboxylate Methyl 4-hydroxy-3,4-dihydro-2H-thieno[3,2]chromene-7-carboxylate (210.0 mg, 0.79 mmol) was dissolved in CH$_2$Cl$_2$ (3.9 mL), and PBr$_3$ (323.0 mg, 1.19 mmol) was added. After stirring at room temperature for 2 hours, and the reaction mixture was concentrated under a reduced pressure to obtain crude solid compound of methyl 4-bromo-3,4-dihydro-2H-thieno[3,2-g]chromene-7-carboxylate (250.0 mg. 95%).

$^1$H-NMR (400 MHz, DMSO-d$_6$): δ 8.18 (s, 1H), 8.07 (s, 1H), 7.54 (s, 1H), 6.05-6.06 (m, 1H), 4.54-4.57 (m, 2H), 3.92 (s, 3H), 2.39-2.45 (m, 2H)

(b) Synthesis of methyl 4-cyano-3,4-dihydro-2H-thieno[3,2-g]chromene-7-carboxylate Methyl 4-bromo-3,4-dihydro-2H-thieno[3,2-g]chromene-7-carboxylate (300.0 mg, 0.91 mmol) was dissolved in DMA (9.1 mL), and NaCN (90.0 mg, 1.83 mmol) was added at room temperature. The mixture was stirred at 60° C. for 2 hours, and extracted with EtOAc. The organic extract was washed with brine, dried over anhydrous Na$_2$SO$_4$, filtered and concentrated under a reduced pressure. The residue was purified by reversed-phase column chromatography (C18-silica gel, 0.1% formic acid in CH$_3$CN:0.1% formic acid in H$_2$O) to obtain methyl 4-cyano-3,4-dihydro-2H-thieno[3,2-g]chromene-7-carboxylate (39.0 mg, 15%) as an off-white solid.

LC/MS ESI (+): 274 (M+1)

$^1$H-NMR (400 MHz, DMSO-d$_6$): δ 8.17 (s, 1H), 8.03 (s, 1H), 7.56 (s, 1H), 4.68 (t, 1H, J=6.0 Hz), 4.31 (t, 2H, J=5.2 Hz), 3.87 (s, 3H), 2.29-2.39 (m, 2H)

(c) Synthesis of 4-cyano-3,4-dihydro-2H-thieno[3,2-g]chromene-7-carboxylic acid Methyl 4-cyano-3,4-dihydro-2H-thieno[3,2-g]chromene-7-carboxylate (39.0 mg, 0.14 mmol) was dissolved in THF/H$_2$O (1.5 mL, 3/1 v/v), and LiOH.H$_2$O (17.9 mg, 0.43 mmol) was added. After stirring at room temperature for 15 hours, the reaction mixture was concentrated under a reduced pressure. The residue was purified by reversed-phase column chromatography (C18-silica gel, 0.1% formic acid in CH$_3$CN:0.1% formic acid in H$_2$O) to obtain methyl 4-cyano-3,4-dihydro-2H-thieno[3,2-g]chromene-7-carboxylate (17.0 mg, 46%) as a white solid.

LC/MS ESI (+): 260 (M+1)

$^1$H-NMR (400 MHz, DMSO-d$_6$): δ 13.3 (br, 1H), 7.96 (s, 1H), 7.91 (s, 1H), 7.44 (s, 1H), 4.60 (t, 1H, J=6.0 Hz), 4.22 (t, 2H, J=5.2 Hz), 2.20-2.26 (m, 2H)

Intermediate 18) Synthesis of 4-azido-3,4-dihydro-2H-thieno[3,2-g]chromene-7-carboxylic acid

(a) Synthesis of methyl 4-azido-3,4-dihydro-2H-thieno[3,2-g]chromene-7-carboxylate Methyl 4-bromo-3,4-dihydro-2H-thieno[3,2-g]chromene-7-carboxylate (95.0 mg, 0.29 mmol) was dissolved in DMA (2.9 mL), The mixture was stirred at 60° C. for 3 hours, and extracted with EtOAc. The organic extract was washed with brine, dried over anhydrous Na$_2$SO$_4$, and concentrated under a reduced pressure. The residue was purified by flash column chromatography (silica gel, n-Hex:EtOAc=6:1) to obtain methyl 4-azido-3,4-dihydro-2H-thieno[3,2-g]chromene-7-carboxylate (50.0 mg, 60%) as a white solid.

LC/MS ESI (+): 290 (M+1)

$^1$H-NMR (400 MHz, CDCl$_3$): δ 7.97 (s, 1H), 7.72 (s, 1H), 7.32 (s, 1H), 4.77 (t, 1H, J=4.1 Hz), 4.31-4.35 (m, 2H), 3.93 (s, 3H), 2.10-2.23 (m, 2H)

(b) Synthesis of 4-azido-3,4-dihydro-2H-thieno[3,2-g]chromene-7-carboxylic acid Methyl 4-azido-3,4-dihydro-2H-thieno[3,2-g]chromene-7-carboxylate (15.0 mg, 0.05 mmol) was dissolved in THF/H$_2$O (0.5 mL, 3/1 v/v), and LiOH.H$_2$O (21.7 mg, 0.52 mmol) was added. The reaction mixture was stirred at 60° C. for 15 hours, 1N HCl (3.0 mL) was added, and extracted with CH$_2$Cl$_2$. The organic extract was washed with brine, dried over anhydrous Na$_2$SO$_4$ and concentrated under reduced pressure to obtain 4-azido-3,4-dihydro-2H-thieno[3,2-g]chromene-7-carboxylic acid (10.0 mg, 70%) as an off-white solid.

LC/MS ESI (−): 274 (M−1)

Example 1) Synthesis of N-(2-chloro-6-(4-chlorophenoxy)pyridin-4-yl)-1-(methylsulfonyl)-2,3-dihydro-1H-thieno[3',2':4,5]benzo[1,2-b][1,4]oxazine-7-carboxamide

(a) Synthesis of 2-chloro-6-(4-chlorophenoxy)pyridin-4-amine 2,6-Dichloropyridine-4-amine (3.0 g, 18.40 mmol) and 4-chlorophenol (4.7 g, 36.80 mmol) were dissolved in sulfolane (96.0 mL) and K$_2$CO$_3$ (5.1 g, 36.80 mmol) was added. The reaction mixture was stirred at 160° C. for 24 hours, cooled to room temperature, H$_2$O was added, and extracted with EtOAc. The organic extract was washed with 1N NaOH aqueous solution and brine, dried over anhydrous Na$_2$SO$_4$ and concentrated under reduced pressure. The residue was purified by reversed-phase column chromatography (C18-silica gel, 0.1% formic acid in CH$_3$CN:0.1% formic acid in H$_2$O) to obtain 2-chloro-6-(4-chlorophenoxy)pyridin-4-amine (2.5 g, 53%) as a white solid.

LC/MS ESI (+): 255 (M+1)

$^1$H-NMR (400 MHz, DMSO-d$_6$): δ 7.45 (d, 2H, J=8.8 Hz), 7.12 (d, 2H, J=8.8 Hz), 6.55 (brs, 2H), 6.31 (d, 1H, J=1.6 Hz), 5.93 (d, 1H, J=1.6 Hz)

(b) Synthesis of N-(2-chloro-6-(4-chlorophenoxy)pyridin-4-yl)-1-(methylsulfonyl)-2,3-dihydro-1H-thieno[3',2':4,5]benzo[1,2-b][1,4]oxazine-7-carboxamide 1-(Methylsulfonyl)-2,3-dihydro-1H-thieno[3',2':4,5]benzo[1,2-b][1,4]oxazine-7-carboxylic acid (190.0 mg, 0.61 mmol) was dissolved in CH$_2$Cl$_2$ (6.1 mL), and DMF (1.2 μL, 0.01 mmol) and (COCl)$_2$ (51.6 μL, 0.61 mmol) were added. The reaction mixture was stirred at 25° C. for 2 hours and concentrated under reduced pressure to obtain 1-(methylsulfonyl)-2,3-dihydro-1H-thieno[3',2':4,5]benzo[1,2-b][1,4]oxazine-7-carbonyl chloride. To the residue, 2-chloro-6-(4-chlorophenoxy)pyridin-4-amine (155.0 mg, 0.61 mmol) and 1,4-Dioxane (2.0 mL) were added and the reaction mixture was stirred at 80° C. for 15 hours and concentrated under reduced pressure. The residue was purified by reversed-phase column chromatography (C18-silica gel, 0.1% formic acid in CH$_3$CN:0.1% formic acid in H$_2$O) to obtain N-(2-chloro-6-(4-chlorophenoxy)pyridin-4-yl)-1-(methylsulfonyl)-2,3-dihydro-1H-thieno[3',2':4,5]benzo[1,2-b][1,4]oxazine-7-carboxamide (166.0 mg, 50%) as a white solid.

LC/MS ESI (+): 550 (M+1)

$^1$H-NMR (400 MHz, DMSO-d$_6$): δ 10.87 (brs, 1H), 8.20 (s, 1H), 8.10 (s, 1H), 7.58 (s, 2H), 7.45 (dd, 2H, J=8.8, 2.1 Hz), 7.22 (s, 1H), 7.18 (dd, 2H, J=8.8, 2.1 Hz), 4.29 (t, 2H, J=4.9 Hz), 3.82 (t, 2H, J=4.6 Hz), 3.11 (s, 3H)

Compounds from Examples 2 to 14 were synthesized through the synthesis route of Example 1, and data of these compounds are listed as follows.

TABLE 2

| Ex. | Compound | Analysis data |
|---|---|---|
| 2 | N-(2-chloro-6-(4-chlorophenoxy)pyridin-4-yl)-3,3-dimethyl-1-(methylsulfonyl)- | LC/MS ESI (+): 578 (M + 1)<br>$^1$H-NMR(400 MHz, DMSO-d$_6$): δ 10.94 (s, |

TABLE 2-continued

| Ex. | Compound | Analysis data |
|---|---|---|
|  | 2,3-dihydro-1H-thieno[3',2': 4,5]benzo[1,2-b][1,4]oxazine-7-carboxamide | 1H), 8.28 (s, 1H), 8.18 (s, 1H), 7.67 (s, 1H), 7.58 (s, 1H), 7.53 (d, 2H, J = 8.8 Hz), 7.31 (s, 1H), 7.25 (d, 2H, J = 8.8 Hz), 3.68 (s, 2H), 3.38 (s, 3H), 1.36 (s, 6H) |
| 3 | N-(2-chloro-6-(4-chlorophenoxy)pyridin-4-yl)-1-(methylsulfonyl)-1,2,3,4-tetrahydrothieno[3',2': 4,5]benzo[1,2-b][1,4]oxazepine-8-carboxamide | LC/MS ESI (+): 564 (M + 1)<br>$^1$H-NMR(400 MHz, DMSO-$d_6$): δ 11.10 (s, 1H), 8.36 (s, 1H), 8.08 (s, 1H), 7.90 (s, 1H), 7.70 (d, 1H, J = 1.2 Hz), 7.55 (d, 2H, J = 8.8 Hz), 7.33 (s, 1H, J = 1.2 Hz), 7.29 (d, 2H, J = 8.8 Hz), 4.15-4.17 (m, 2H), 3.75-3.77 (m, 2H), 3.11 (s, 3H), 2.08-2.10 (m, 2H) |
| 4 | N-(2-chloro-6-(4-chlorophenoxy)pyridin-4-yl)-8,8-dimethyl-5-(methylsulfonyl)-5,6,7,8-tetrahydrothieno[2,3-g]quinoline-2-carboxamide | LC/MS ESI (+): 576 (M + 1)<br>$^1$H-NMR(400 MHz, DMSO-$d_6$): δ 10.98 (s, 1H), 8.30 (s, 1H), 8.21 (s, 1H), 8.14 (s, 1H), 7.67 (s, 1H), 7.53 (d, 2H, J = 8.7 Hz), 7.32 (s, 1H), 7.26 (d, 2H, J = 8.7 Hz), 3.79 (t, 2H, J = 5.7 Hz), 3.12 (s, 3H), 1.85 (t, 2H, J = 5.7 Hz), 1.37 (s, 6H) |
| 5 | tert-butyl 7-((2-chloro-6-(4-chlorophenoxy)pyridin-4-yl)carbamoyl)-1-(methylsulfonyl)-2,3-dihydrothieno[2,3-g]quinoxaline-4(1H)-carboxylate | LC/MS ESI (+): 679 (M + 1)<br>$^1$H-NMR (400 MHz, DMSO-$d_6$): δ 10.93 (brs, 1H), 8.35 (s, 1H), 8.24 (s, 1H), 8.03 (d, 1H, J = 8.7 Hz), 7.60 (d, 1H, J = 1.3 Hz), 7.47 (d, 2H, J = 8.8 Hz), 7.24 (d, 1H, J = 1.3 Hz), 7.19 (d, 2H, J = 8.8 Hz), 3.82-3.84 (m, 2H), 3.79-3.80 (m, 2H), 3.05 (s, 3H), 1.43 (s, 9H) |
| 6 | N-(2-chloro-6-(4-chlorophenoxy)pyridin-4-yl)-5-(methylsulfonyl)-5,6,7,8-tetrahydrothieno[2,3-g]quinoline-2-carboxamide | LC/MS ESI (+): 548 (M + 1)<br>$^1$H-NMR (400 MHz, DMSO-$d_6$): δ 10.98 (s, 1H), 8.32 (s, 1H), 8.13 (s, 1H), 7.90 (s, 1H), 7.66 (s, 1H), 7.53 (d, 2H, J = 8.8 Hz), 7.28 (s, 1H), 7.26 (d, 2H, J = 8.8 Hz), 3.75 (t, 2H, J = 6.3 Hz ), 3.06 (s, 3H), 2.93 (t, 2H, J = 6.5 Hz), 1.95-1.99 (m, 2H) |
| 7 | N-(2-chloro-6-(4-chlorophenoxy)pyridin-4-yl)-4-methyl-1-(methylsulfonyl)-1,2,3,4-tetrahydrothieno[2,3-g]quinoxaline-7-carboxamide | LC/MS ESI (+): 563 (M + 1)<br>$^1$H-NMR (400 MHz, DMSO-$d_6$): δ 10.81 (brs, 1H), 8.20 (s, 1H), 7.89 (s, 1H), 7.67 (s, 1H), 7.55 (d, 2H, J = 8.7 Hz), 7.33 (s, 1H), 7.32 (s, 1H), 7.28 (d, 2H, J = 8.7 Hz), 3.79 (t, 2H, J = 5.3 Hz ), 3.53 (t, 2H, J = 5.3 Hz ), 3.04 (d, 6H, J = 2.6 Hz) |
| 8 | N-(2-chloro-6-(4-chlorophenoxy)pyridin-4-yl)-4-(methylsulfonyl)-3,4-dihydro-2H-thieno[3,2-g]chromene-7-carboxamide | LC/MS ESI (+): 549 (M + 1).<br>$^1$H-NMR (400 MHz, DMSO-$d_6$): δ 10.94 (s, 1H), 8.31 (s, 1H), 8.08 (s, 1H), 7.67 (d, 1H, J = 1.1 Hz), 7.59 (s, 1H), 7.53 (d, 2H, J = 8.9 Hz), 7.31 (d, 1H, J = 1.1 Hz), 7.27 (d, 2H, J = 8.9 Hz), 4.82 (m, 1H), 4.46-4.53 (m, 1H), 4.31-4.36 (m, 1H), 3.18 (s, 3H), 2.53-2.69 (m, 1H), 2.29-2.40 (m, 1H). |
| 9 | N-(2-chloro-6-(4-chlorophenoxy)pyridin-4-yl)-5-(methylsulfonyl)-2,3,4,5-tetrahydrothieno[3',2': 4,5]benzo[1,2-b]oxepine-8-carboxamide | LC/MS ESI (+): 563 (M + 1)<br>$^1$H-NMR (400 MHz, DMSO-$d_6$): δ 10.90 (s, 1H), 8.28 (s, 1H), 8.03 (s, 1H), 7.69 (s, 1H), 7.59 (d, 1H, J = 1.4 Hz), 7.44-7.48 (m, 2H), 7.25 (s, 1H), 7.17-7.21 (m, 2H), 4.78 (t, 1H, J = 5.4 Hz), 4.29-4.34 (m, 1H), 3.68-3.73 (m, 1H), 2.81 (s, 3H), 2.25-2.50 (m, 1H), 2.16-2.19 (m, 1H), 2.04-2.04 (m, 1H), 1.70-1.74 (m, 1H) |
| 10 | N-(2-chloro-6-(4-chlorophenoxy)pyridin-4-yl)-5-(methylsulfonyl)-5,6,7,8-tetrahydronaphtho[2,3-b]thiophene-2-carboxamide | LC/MS ESI (+): 547 (M + 1)<br>$^1$H-NMR (400 MHz, DMSO-$d_6$): δ 11.0 (s, 1H), 8.35 (s, 1H), 8.12 (s, 1H), 7.91 (s, 1H), 7.66 (d, 1H, J = 1.3 Hz), 7.53 (d, 2H, J = 8.9 Hz), 7.31 (d, 1H, J = 1.3 Hz), 7.26 (d, 2H, J = 8.9 Hz), 4.76-4.79 (m, 1H), 3.01 (s, 3H), 2.82-2.94 (m, 2H), 2.43-2.46 (m, 1H), 2.14-2.20 (m, 2H), 1.62-1.66 (m, 1H) |
| 11 | N-(2-chloro-6-(4-chlorophenoxy)pyridin-4-yl)-4-methyl-4-(methylsulfonyl)-3,4-dihydro-2H-thieno[3,2-g]chromene-7-carboxamide | LC/MS ESI (+): 563 (M + 1)<br>$^1$H-NMR (400 MHz, DMSO-$d_6$): δ 10.94 (brs, 1H), 8.29 (s, 1H), 8.25 (s, 1H), 7.65 (s, 1H), 7.57 (s, 1H), 7.52 (d, 2H, J = 8.5 Hz), 7.30 (s, 1H), 7.25 (d, 2H, J = 8.3 Hz), 4.49-4.54 (m, 1H), 4.20-4.24 (m, 1H), 2.98 (s, 3H), 2.62 (m, 1H), 2.15-2.22 (m, 1H), 1.84 (s, 3H) |
| 12 | N-(2-chloro-6-(4-chlorophenoxy)pyridin-4-yl)-5-(methylsulfonyl)-5,8-dihydro-6H-thieno[3,2-g]isochromene-2-carboxamide | LC/MS ESI (+): 549 (M + 1)<br>$^1$H-NMR(400 MHz, DMSO-$d_6$): δ 10.96 (brs, 1H), 8.32 (s, 1H), 8.09 (s, 1H), 7.87 (s, 1H), 7.60 (d, 1H, J = 1.2 Hz), 7.45-7.47 (m, 2H), 7.25 (d, 1H, J = 0.8 Hz), 7.18-7.22 (m, 2H), 4.96 (d, 1H, J = 15.6 Hz), 4.82 (d, 1H, J = 15.6 Hz), 4.60 (d, 1H, J = 12.8 Hz), 4.48 (s, |

TABLE 2-continued

| Ex. | Compound | Analysis data |
|---|---|---|
| 13 | N-(2-chloro-6-(4-chlorophenoxy)pyridin-4-yl)-4-fluoro-4-(methylsulfonyl)-3,4-dihydro-2H-thieno[3,2-g]chromene-7-carboxamide | 1H), 4.03 (dd, 1H, J = 12.8, 3.6 Hz), 2.63 (s, 3H)<br>LC/MS ESI (+): 567 (M + 1)<br>$^1$H-NMR (400 MHz, DMSO-d$_6$):<br>δ 10.92 (brs, 1H), 8.27 (s, 1H), 8.24 (s, 1H), 7.64 (s, 1H), 7.58 (s, 1H), 7.46 (d, 2H, J = 8.8 Hz), 7.21 (s, 1H), 7.18 (d, 2H, J = 8.8 Hz), 4.46-4.52 (m, 1H), 4.33-4.38 (m, 1H), 2.93 (s, 3H), 2.87-2.93 (m, 1H), 2.60-2.67 (m, 1H) |
| 14 | N-(2-chloro-6-(4-chlorophenoxy)pyridin-4-yl)-8,8-difluoro-5-(methylsulfonyl)-5,6,7,8-tetrahydronaphtho[2,3-b]thiophene-2-carboxamide | LC/MS ESI (−): 581 (M − 1)<br>$^1$H-NMR (400 MHz, DMSO-d6): δ 11.13 (s, 1H), 8.57 (s, 1H), 8.43 (s, 1H), 8.23 (s, 1H), 7.67 (d, 1H, J = 1.1 Hz), 7.52 (d, 2H, J = 8.9 Hz), 7.31 (d, 1H, J = 0.7 Hz), 7.26 (d, 2H, J = 8.9 Hz), 4.91 (m, 1H), 3.19 (s, 3H), 2.80-2.90 (m, 1H), 2.70-2.75 (m, 1H), 2.36-2.45 (m, 2H) |

Example 15) Synthesis of N-(2-chloro-6-(p-tolyloxy)pyridin-4-yl)-4-(methylsulfonyl)-3,4-dihydro-2H-thieno[3,2-g]chromene-7-carboxamide (a) Synthesis of 2-chloro-6-(p-tolyloxy)pyridin-4-amine To a solution of 2,6-dichloropyridin-4-amine (200.0 mg, 1.23 mmol) in sulfolane (4090.0 µl) were added p-cresol (265.0 mg, 2.45 mmol) and K$_2$CO$_3$ (339.0 mg, 2.45 mmol). The reaction mixture was stirred at 160° C. for 30 hours. The reaction mixture was extracted with EtOAc. The organic extract was washed with 1N-NaOH and brine, dried over anhydrous Na$_2$SO$_4$, filtered and concentrated. The residue was purified by reversed-phase column chromatography (C18-silica gel, 0.1% formic acid in CH$_3$CN:0.1% formic acid in H$_2$O) and solidification with ACN/ether/Hex to obtain 2-chloro-6-(p-tolyloxy)pyridin-4-amine (160.0 mg, 56%) as a light brown amorphous.

$^1$H-NMR (400 MHz, CDCl$_3$): δ 7.17 (d, 2H, J=8.2 Hz), 7.00 (d, 2H, J=8.5 Hz), 6.30 (d, 1H, J=1.7 Hz), 5.81 (d, 1H, J=1.7 Hz), 4.22 (brs, 2H), 2.35 (s, 3H)

(b) Synthesis of N-(2-chloro-6-(p-tolyloxy)pyridin-4-yl)-4-(methylsulfonyl)-3,4-dihydro-2H-thieno[3,2-g]chromene-7-carboxamide The synthesis procedure of Example 1-b was repeated except for using 2-chloro-6-(p-tolyloxy)pyridin-4-amine (41.3 mg, 0.18 mmol) to obtain N-(2-chloro-6-(p-tolyloxy)pyridin-4-yl)-4-(methylsulfonyl)-3,4-dihydro-2H-thieno[3,2-g]chromene-7-carboxamide (51.0 mg, 60%) as a white amorphous.

LC/MS ESI (+): 529 (M+1)

$^1$H-NMR (400 MHz, DMSO-d6): δ 10.89 (s, 1H), 8.29 (s, 1H), 8.05 (s, 1H), 7.64 (d, 1H, J=1.4 Hz), 7.58 (s, 1H), 7.27 (d, 2H, J=8.3 Hz), 7.21 (d, 1H, J=1.4 Hz), 7.08 (d, 2H, J=8.4 Hz), 4.81 (m, 1H), 4.44-4.51 (m, 1H), 4.29-4.34 (m, 1H), 3.16 (s, 3H), 2.59-2.67 (m, 1H), 2.32-2.34 (m, 4H)

Compounds from Examples 16 to 42 were synthesized through the synthesis route of Example 15, and data of these compounds are listed as follows.

TABLE 3

| Ex. | Compound | Analysis data |
|---|---|---|
| 16 | N-(2-chloro-6-(3-(trifluoromethyl)phenoxy)pyridin-4-yl)-4-(methylsulfonyl)-3,4-dihydro-2H-thieno[3,2-g]chromene-7-carboxamide | LC/MS ESI (+): 583 (M + 1)<br>$^1$H-NMR (400 MHz, DMSO-d$_6$): δ 10.97 (s, 1H), 8.32 (s, 1H), 8.08 (s, 1H), 7.65-7.74 (m, 4H), 7.55-7.59 (m, 2H), 7.40 (d, 1H, J = 1.2 Hz), 4.81-4.84 (m, 1H), 4.49-4.53 (m, 1H), 4.31-4.34 (m, 1H), 3.17 (s, 3H), 2.60-2.68 (m, 1H), 2.35-2.36 (m, 1H) |
| 17 | N-(2-chloro-6-(4-(trifluoromethyl)phenoxy)pyridin-4-yl)-4-(methylsulfonyl)-3,4-dihydro-2H-thieno[3,2-g]chromene-7-carboxamide | LC/MS ESI (+): 583 (M + 1)<br>$^1$H-NMR (400 MHz, DMSO-d$_6$): δ 10.98 (s, 1H), 8.32 (s, 1H), 8.08 (s, 1H), 7.85 (d, 2H, J = 8.6 Hz), 7.71 (s, 1H), 7.59 (s, 1H), 7.41-7.45 (m, 3H), 4.82-4.83 (m, 1H), 4.49-4.52 (m, 1H), 4.31-4.35 (m, 1H), 3.17 (s, 3H), 2.60-2.65 (m, 1H), 2.36-2.39 (m, 1H) |
| 18 | N-(2-chloro-6-(3,5-dichlorophenoxy)pyridin-4-yl)-4-(methylsulfonyl)-3,4-dihydro-2H-thieno[3,2-g]chromene-7-carboxamide | LC/MS ESI (+): 583 (M + 1)<br>$^1$H-NMR (400 MHz, DMSO-d$_6$): δ 10.98 (s, 1H), 8.32 (s, 1H), 8.08 (s, 1H), 7.70 (d, 2H, J = 1.2 Hz), 7.59 (s, 1H), 7.56 (t, 1H, J = 2.0 Hz), 7.44 (d, 2H, J = 2.0 Hz), 7.37 (s, 1H), 4.82-4.84 (m, 1H), 4.46-4.52 (m, 1H), 4.32-4.35 (m, 1H), 3.17 (s, 3H), 2.60-2.65 (m, 1H), 2.36-2.39 (m, 1H) |
| 19 | N-(2-chloro-6-(4-chloro-3-fluorophenoxy)pyridin-4-yl)-4-(methylsulfonyl)-3,4-dihydro-2H-thieno[3,2-g]chromene-7-carboxamide | LC/MS ESI (+): 567 (M + 1)<br>$^1$H-NMR (400 MHz, DMSO-d$_6$): δ 10.96 (s, 1H), 8.30 (s, 1H), 8.07 (s, 1H), 7.67-7.69 (m, 2H), 7.58 (s, 1H), 7.47 (d, 1H, J = 10.3 Hz), |

TABLE 3-continued

| Ex. | Compound | Analysis data |
|---|---|---|
| | | 7.35 (s, 1H), 7.15 (d, 1H, J = 10.3 Hz), 4.83-4.85 (m, 1H), 4.49-4.52 (m, 1H), 4.30-4.34 (m, 1H), 3.17 (s, 3H), 2.60-2.65 (m, 1H), 2.36-2.39 (m, 1H) |
| 20 | N-(2-chloro-6-(4-chloro-3-methylphenoxy)pyridin-4-yl)-4-(methylsulfonyl)-3,4-dihydro-2H-thieno[3,2-g]chromene-7-carboxamide | LC/MS ESI (+): 563 (M + 1)<br>$^1$H-NMR (400 MHz, DMSO-$d_6$): 10.92 (brs, 1H), 8.29 (s, 1H), 8.06 (s, 1H), 7.67 (s, 1H), 7.58 (s, 1H), 7.50 (d, 1H, J = 8.7 Hz), 7.25-7.26 (m, 2H), 7.09 (dd, 1H, J = 8.6, 2.8 Hz), 4.82 (m, 1H), 4.45-4.51 (m, 1H), 4.30-4.34 (m, 1H), 3.16 (s, 3H), 2.60-2.64 (m, 1H), 2.32-2.35 (m, 4H) |
| 21 | N-(2-chloro-6-(4-chloro-2-methylphenoxy)pyridin-4-yl)-4-(methylsulfonyl)-3,4-dihydro-2H-thieno[3,2-g]chromene-7-carboxamide | LC/MS ESI (+): 563 (M + 1)<br>$^1$H-NMR (400 MHz, DMSO-$d_6$): 10.92 (s, 1H), 8.30 (s, 1H), 8.06 (s, 1H), 7.64 (m, 1H), 7.58 (s, 1H), 7.47 (m, 1H), 7.35 (dd, 1H, J = 8.6, 2.6 Hz), 7.26 (m, 1H), 7.19 (d, 1H, J = 8.6 Hz), 4.81 (m, 1H), 4.45-4.51 (m, 1H), 4.30-4.34 (m, 1H), 3.19 (s, 3H), 2.60-2.67 (m, 1H), 2.32-2.36 (m, 1H), 2.12 (s, 3H) |
| 22 | N-(2-chloro-6-(4-methoxyphenoxy)pyridin-4-yl)-4-(methylsulfonyl)-3,4-dihydro-2H-thieno[3,2-g]chromene-7-carboxamide | LC/MS ESI (+): 545 (M + 1)<br>$^1$H-NMR (400 MHz, DMSO-d6): δ 10.88 (s, 1H), 8.29 (s, 1H), 8.05 (s, 1H), 7.63 (d, 1H, J = 1.2 Hz), 7.58 (s, 1H), 7.19 (d, 1H, J = 1.2 Hz), 7.14 (d, 2H, J = 9.0 Hz), 7.01 (d, 2H, J = 9.0 Hz), 4.81 (m, 1H), 4.44-4.51 (m, 1H), 4.29-4.34 (m, 1H), 3.79 (s, 3H), 3.16 (s, 3H), 2.59-2.67 (m, 1H), 2.30-2.39 (m, 1H) |
| 23 | N-(2-chloro-6-(4-chloro-2-fluorophenoxy)pyridin-4-yl)-4-(methylsulfonyl)-3,4-dihydro-2H-thieno[3,2-g]chromene-7-carboxamide | LC/MS ESI (+): 567 (M + 1)<br>$^1$H-NMR (400 MHz, DMSO-$d_6$): δ 10.90 (brs, 1H), 8.24 (s, 1H), 8.00 (s, 1H), 7.62 (dd, 1H, J = 10.4, 2.4 Hz), 7.57 (s, 1H), 7.51 (s, 1H), 7.30-7.41 (m, 3H), 4.73-4.75 (m, 1H), 4.38-4.45 (m, 1H), 4.23-4.27 (m, 1H), 3.09 (s, 3H), 2.53-2.61 (m, 1H), 2.27-2.32 (m, 1H) |
| 24 | N-(2-chloro-6-(3,4-dichlorophenoxy)pyridin-4-yl)-4-(methylsulfonyl)-3,4-dihydro-2H-thieno[3,2-g]chromene-7-carboxamide | LC/MS ESI (+): 585 (M + 1)<br>$^1$H-NMR (400 MHz, DMSO-$d_6$): δ 10.88 (brs, 1H), 8.23 (s, 1H), 8.00 (s, 1H), 7.65 (d, 1H, J = 8.8 Hz), 7.60 (s, 1H), 7.57 (d, 1H, J = 2.7 Hz), 7.51 (s, 1H), 7.27 (s, 1H), 7.20 (dd, 1H, J = 8.8, 2.7 Hz), 4.73-4.75 (m, 1H), 4.38-4.45 (m, 1H), 4.23-4.27 (m, 1H), 3.09 (s, 3H), 2.53-2.60 (m, 1H), 2.27-2.32 (m, 1H) |
| 25 | N-(2-chloro-6-(3-chlorophenoxy)pyridin-4-yl)-4-(methylsulfonyl)-3,4-dihydro-2H-thieno[3,2-g]chromene-7-carboxamide | LC/MS ESI (+): 549 (M + 1)<br>$^1$H-NMR (400 MHz, DMSO-$d_6$): δ 10.87 (brs, 1H), 8.24 (s, 1H), 8.00 (s, 1H), 7.60 (s, 1H), 7.51 (s, 1H), 7.43 (t, 1H, J = 8.1 Hz), 7.28-7.31 (m, 2H), 7.26 (d, 1H, J = 1.3 Hz), 7.12-7.15 (m, 1H), 4.73-4.75 (m, 1H), 4.38-4.45 (m, 1H), 4.23-4.27 (m, 1H), 3.09 (s, 3H), 2.53-2.60 (m, 1H), 2.27-2.32 (m, 1H) |
| 26 | N-(2-chloro-6-(4-fluorophenoxy)pyridin-4-yl)-4-(methylsulfonyl)-3,4-dihydro-2H-thieno[3,2-g]chromene-7-carboxamide | LC/MS ESI (+): 533 (M + 1)<br>$^1$H-NMR (400 MHz, DMSO-$d_6$): δ 10.84 (brs, 1H), 8.23 (s, 1H), 7.99 (s, 1H), 7.57 (s, 1H), 7.51 (s, 1H), 7.18-7.26 (m, 5H), 4.74-4.76 (m, 1H), 4.38-4.44 (m, 1H), 4.24-4.26 (m, 1H), 3.09 (s, 3H), 2.53-2.60 (m, 1H), 2.27-2.32 (m, 1H) |
| 27 | N-(2-chloro-6-(3-chloro-4-fluorophenoxy)pyridin-4-yl)-4-(methylsulfonyl)-3,4-dihydro-2H-thieno[3,2-g]chromene-7-carboxamide | LC/MS ESI (+): 567 (M + 1)<br>$^1$H-NMR(400 MHz, DMSO-$d_6$): δ 10.87 (brs, 1H), 8.23 (s, 1H), 8.00 (s, 1H), 7.59 (d, 1H, J = 0.8 Hz), 7.44-7.53 (m, 3H), 7.19-7.24 (m, 2H), 4.74-4.75 (m, 1H), 4.38-4.45 (m, 1H), 4.23-4.27 (m, 1H), 3.09 (s, 3H), 2.53-2.57 (m, 1H), 2.24-2.32 (m, 1H) |
| 28 | N-(2-chloro-6-(4-(trifluoromethoxy)phenoxy)pyridin-4-yl)-4-(methylsulfonyl)-3,4-dihydro-2H-thieno[3,2-g]chromene-7-carboxamide | LC/MS ESI (+): 599 (M + 1)<br>$^1$H-NMR(400 MHz, DMSO-$d_6$): δ 10.95 (brs, 1H), 8.28 (brs, 1H), 8.06 (s, 1H), 7.66 (s, 1H), 7.57 (s, 1H), 7.47 (d, 2H, J = 8.8 Hz), 7.33-7.36 (m, 3H), 4.81-4.82 (m, 1H), 4.45-4.52 (m, 1H), 4.29-4.34 (m, 1H), 3.16 (s, 3H), 2.60-2.64 (m, 1H), 2.31-2.39 (m, 1H) |
| 29 | N-(2-chloro-6-(3-(trifluoromethoxy)phenoxy)pyridin-4-yl)-4-(methylsulfonyl)-3,4-dihydro-2H-thieno[3,2-g]chromene-7-carboxamide | LC/MS ESI (+): 599 (M + 1)<br>$^1$H-NMR(400 MHz, DMSO-$d_6$): δ 10.96 (brs, 1H), 8.30 (s, 1H), 8.07 (s, 1H), 7.67 (d, 1H, J = 1.2 Hz), 7.58-7.62 (m, 2H), 7.37 (d, 1H, J = 0.8 Hz), 7.26-7.32 (m, 3H), 4.81-4.82 (m, 1H), 4.45-4.52 (m, 1H), 4.30-4.34 (m, 1H), |

TABLE 3-continued

| Ex. | Compound | Analysis data |
|---|---|---|
| | | 3.16 (s, 3H), 2.60-2.64 (m, 1H), 2.30-2.39 (m, 1H) |
| 30 | N-(2-chloro-6-(3-chloro-5-methoxyphenoxy)pyridin-4-yl)-4-(methylsulfonyl)-3,4-dihydro-2H-thieno[3,2-g]chromene-7-carboxamide | LC/MS ESI (+): 580 (M + 1)<br>¹H-NMR (400 MHz, DMSO-d₆): δ 10.87 (brs, 1H), 8.23 (s, 1H), 7.99 (s, 1H), 7.61 (s, 1H), 7.50 (s, 1H), 7.22 (s, 1H), 6.89-6.90 (m, 1H), 6.85-6.86 (m, 1H), 6.74-6.75 (m, 1H), 4.74-4.75 (m, 1H), 4.38-4.43 (m, 1H), 4.23-4.27 (m, 1H), 3.75 (s, 3H), 3.09 (s, 3H), 2.53-2.57 (m, 1H), 2.29-2.32 (m, 1H) |
| 31 | N-(2-chloro-6-(3-chloro-5-fluorophenoxy)pyridin-4-yl)-4-(methylsulfonyl)-3,4-dihydro-2H-thieno[3,2-g]chromene-7-carboxamide | LC/MS ESI (+): 566 (M + 1)<br>¹H-NMR (400 MHz, DMSO-d₆): δ 10.90 (brs, 1H), 8.23 (s, 1H), 8.00 (s, 1H), 7.62 (s, 1H), 7.51 (s, 1H), 7.31-7.32 (m, 1H), 7.30 (s, 1H), 7.20 (s, 1H), 7.16-7.19 (m, 1H), 4.74-4.75 (m, 1H), 4.38-4.43 (m, 1H), 4.23-4.27 (m, 1H), 3.09 (s, 3H), 2.53-2.57 (m, 1H), 2.29-2.32 (m, 1H) |
| 32 | N-(2-chloro-6-(3-fluoro-5-methoxyphenoxy)pyridin-4-yl)-4-(methylsulfonyl)-3,4-dihydro-2H-thieno[3,2-g]chromene-7-carboxamide | LC/MS ESI (+): 563 (M + 1)<br>¹H-NMR (400 MHz, DMSO-d₆): δ 10.86 (brs, 1H), 8.22 (s, 1H), 7.99 (s, 1H), 7.61 (s, 1H), 7.50 (s, 1H), 7.22 (s, 1H), 6.64-6.72 (m, 2H), 6.61 (s, 1H), 4.74-4.76 (m, 1H), 4.38-4.44 (m, 1H), 4.24-4.26 (m, 1H), 3.72 (s, 3H), 3.09 (s, 3H), 2.53-2.60 (m, 1H), 2.27-2.32 (m, 1H) |
| 33 | N-(2-chloro-6-(m-tolyloxy)pyridin-4-yl)-4-(methylsulfonyl)-3,4-dihydro-2H-thieno[3,2-g]chromene-7-carboxamide | LC/MS ESI (+): 529 (M + 1)<br>¹H-NMR (400 MHz, DMSO-d₆): δ 10.83 (brs, 1H), 8.22 (s, 1H), 7.98 (s, 1H), 7.59 (s, 1H), 7.50 (s, 1H), 7.28 (t, 1H, J = 7.7 Hz), 7.15 (s, 1H), 7.03 (d, 1H, J = 7.6 Hz), 6.95 (s, 1H), 6.91-6.93 (m, 1H), 4.74-4.76 (m, 1H), 4.38-4.44 (m, 1H), 4.24-4.26 (m, 1H), 3.09 (s, 3H), 2.53-2.60 (m, 1H), 2.27 (s, 3H), 2.27-2.32 (m, 1H) |
| 34 | N-(2-chloro-6-(3,4-difluorophenoxy)pyridin-4-yl)-4-(methylsulfonyl)-3,4-dihydro-2H-thieno[3,2-g]chromene-7-carboxamide | LC/MS ESI (+): 551 (M + 1)<br>¹H-NMR(400 MHz, DMSO-d₆): δ 10.94 (brs, 1H), 8.29 (s, 1H), 8.06 (s, 1H), 7.65 (s, 1H), 7.47-7.58 (m, 3H), 7.31 (s, 1H), 7.10-7.14 (m, 1H), 4.81-4.82 (m, 1H), 4.45-4.51 (m, 1H), 4.30-4.34 (m, 1H), 3.16 (s, 3H), 2.60-2.64 (m, 1H), 2.30-2.39 (m, 1H) |
| 35 | N-(2-chloro-6-(5-chloro-2-fluorophenoxy)pyridin-4-yl)-4-(methylsulfonyl)-3,4-dihydro-2H-thieno[3,2-g]chromene-7-carboxamide | LC/MS ESI (+): 567 (M + 1)<br>¹H-NMR (400 MHz, DMSO-d₆): 10.99 (brs, 1H), 8.32 (s, 1H), 8.08 (s, 1H), 7.65 (s, 1H), 7.62 (dd, 1H, J = 6.9, 2.6 Hz), 7.59 (s, 1H), 7.47-7.52 (m, 1H), 7.41-7.45 (m, 2H), 4.82 (m, 1H), 4.45-4.49 (m, 1H), 4.31-4.35 (m, 1H), 3.17 (s, 3H), 2.60-2.64 (m, 1H), 2.35-2.39 (m, 1H) |
| 36 | N-(2-chloro-6-(3-chloro-2-fluorophenoxy)pyridin-4-yl)-4-(methylsulfonyl)-3,4-dihydro-2H-thieno[3,2-g]chromene-7-carboxamide | LC/MS ESI (+): 567 (M + 1)<br>¹H-NMR (400 MHz, DMSO-d₆): 11.00 (s, 1H), 8.32 (s, 1H), 8.09 (s, 1H), 7.66 (d, 1H, J = 1.2 Hz), 7.59 (s, 1H), 7.55 (td, 1H, J = 8.4, 1.6 Hz), 7.47 (s, 1H), 7.15 (td, 1H, J = 9.2, 1.6 Hz), 7.34 (td, 1H, J = 8.4, 2.8 Hz), 4.82-4.83 (m, 1H), 4.49-4.53 (m, 1H), 4.32-4.35 (m, 1H), 3.17 (s, 3H), 2.60-2.65 (m, 1H), 2.36-2.39 (m, 1H) |
| 37 | N-(2-chloro-6-(5-chloro-2-methylphenoxy)pyridin-4-yl)-4-(methylsulfonyl)-3,4-dihydro-2H-thieno[3,2-g]chromene-7-carboxamide | LC/MS ESI (+): 561 (M + 1)<br>¹H-NMR (400 MHz, DMSO-d₆): δ 10.92 (s, 1H), 8.30 (s, 1H), 8.07 (s, 1H), 7.64 (d, 1H, J = 1.2 Hz), 7.58 (s, 1H), 7.40 (d, 1H, J = 7.8 Hz), 7.28 (m, 3H), 4.81 (m, 1H), 4.44-4.52 (m, 1H), 4.30-4.34 (m, 1H), 3.16 (s, 3H), 2.59-2.64 (m, 1H), 2.34-2.39 (m, 1H), 2.11 (s, 3H) |
| 38 | N-(2-chloro-6-(3-chloro-4-methylphenoxy)pyridin-4-yl)-4-(methylsulfonyl)-3,4-dihydro-2H-thieno[3,2-g]chromene-7-carboxamide | LC/MS ESI (+): 563 (M + 1)<br>¹H-NMR (400 MHz, DMSO-d₆): δ 10.86 (brs, 1H), 8.23 (s, 1H), 7.99 (s, 1H), 7.59 (s, 1H), 7.51 (s, 1H), 7.38 (d, 1H, J = 8.3 Hz), 7.29 (s, 1H), 7.20 (s, 1H), 7.05 (d, 1H, J = 8.3 Hz), 4.74-4.76 (m, 1H), 4.38-4.44 (m, 1H), 4.24-4.26 (m, 1H), 3.09 (s, 3H), 2.53-2.60 (m, 1H), 2.30 (s, 3H), 2.27-2.32 (m, 1H) |
| 39 | N-(2-chloro-6-(2-(trifluoromethyl)phenoxy)pyridin-4-yl)-4-(methylsulfonyl)-3,4-dihydro-2H-thieno[3,2-g]chromene-7-carboxamide | LC/MS ESI (+): 583 (M + 1)<br>¹H-NMR (400 MHz, DMSO-d₆): δ 10.90 (brs, 1H), 8.25 (s, 1H), 8.00 (s, 1H), 7.78 (d, 1H, J = 7.8 Hz), 7.72 (t, 1H, J = 7.8 Hz), 7.59 (s, 1H), 7.51 (s, 1H), 7.38-7.44 (m, 2H), 7.33 (s, 1H), 4.74-4.76 (m, 1H), 4.38-4.44 (m, 1H), 4.24-4.26 |

TABLE 3-continued

| Ex. | Compound | Analysis data |
|---|---|---|
| | | (m, 1H), 3.09 (s, 3H), 2.53-2.57 (m, 1H), 2.27-2.32 (m, 1H) |
| 40 | N-(2-chloro-6-(2-(trifluoromethoxy)phenoxy)pyridin-4-yl)-4-(methylsulfonyl)-3,4-dihydro-2H-thieno[3,2-g]chromene-7-carboxamide | LC/MS ESI (+): 599 (M + 1)<br>$^1$H-NMR (400 MHz, DMSO-$d_6$): δ 10.91 (brs, 1H), 8.23 (s, 1H), 8.00 (s, 1H), 7.57 (s, 1H), 7.51 (s, 1H), 7.33-7.50 (m, 5H), 4.74-4.75 (m, 1H), 4.38-4.43 (m, 1H), 4.23-4.27 (m, 1H), 3.09 (s, 3H), 2.53-2.57 (m, 1H), 2.27-2.32 (m, 1H) |
| 41 | N-(2-chloro-6-(2-fluoro-3-methylphenoxy)pyridin-4-yl)-4-(methylsulfonyl)-3,4-dihydro-2H-thieno[3,2-g]chromene-7-carboxamide | LC/MS ESI (+): 547 (M + 1)<br>$^1$H-NMR (400 MHz, DMSO-$d_6$): δ 10.94 (s, 1H), 8.30 (s, 1H), 8.07 (s, 1H), 7.64 (d, 1H, J = 1.3 Hz), 7.58 (s, 1H), 7.36 (d, 1H, J = 1.1 Hz), 7.14-7.24 (m, 3H), 4.81 (m, 1H), 4.44-4.52 (m, 1H), 4.30-4.34 (m, 1H), 3.16 (s, 3H), 2.59-2.64 (m, 1H), 2.33-2.39 (m, 1H), 2.29 (s, 3H) |
| 42 | N-(2-chloro-6-(4-chloro-2-methoxyphenoxy)pyridin-4-yl)-4-(methylsulfonyl)-3,4-dihydro-2H-thieno[3,2-g]chromene-7-carboxamide | LC/MS ESI (+): 579 (M + 1)<br>$^1$H-NMR (400 MHz, DMSO-$d_6$): δ 10.81 (brs, 1H), 8.21 (s, 1H), 7.98 (s, 1H), 7.53 (s, 1H), 7.50 (s, 1H), 7.22 (d, 1H, J = 2.3 Hz), 7.17 (d, 1H, J = 8.4 Hz), 7.14 (s, 1H), 7.01 (dd, 1H, J = 8.4, 2.3 Hz), 4.73-4.74 (m, 1H), 4.38-4.44 (m, 1H), 4.23-4.27 (m, 1H), 3.69 (s, 3H), 3.09 (s, 3H), 2.52-2.57 (m, 1H), 2.20-2.27 (m, 1H) |

Examples 43 and 44) Separation of (S)—N-(2-chloro-6-(4-chlorophenoxy)pyridin-4-yl)-4-(methylsulfonyl)-3,4-dihydro-2H-thieno[3,2-g]chromene-7-carboxamide and (R)—N-(2-chloro-6-(4-chlorophenoxy)pyridin-4-yl)-4-(methylsulfonyl)-3,4-dihydro-2H-thieno[3,2-g]chromene-7-carboxamide from rac-N-(2-chloro-6-(4-chlorophenoxy)pyridin-4-yl)-4-(methylsulfonyl)-3,4-dihydro-2H-thieno[3,2-g]chromene-7-carboxamide The racemate of N-(2-chloro-6-(4-chlorophenoxy)pyridin-4-yl)-4-(methylsulfonyl)-3,4-dihydro-2H-thieno[3,2-g]chromene-7-carboxamide (100.0 mg, 0.18 mmol) obtained in Example 8 was separated by preparative HPLC (Daicel Chiralpak IA, dichloromethane/ethanol=98/2, 10.0 mL/min, 254 nm, 35° C.) into (S)—N-(2-chloro-6-(4-chlorophenoxy)pyridin-4-yl)-4-(methylsulfonyl)-3,4-dihydro-2H-thieno[3,2-g]chromene-7-carboxamide (45.0 mg, 45%) and (R)—N-(2-chloro-6-(4-chlorophenoxy)pyridin-4-yl)-4-(methylsulfonyl)-3,4-dihydro-2H-thieno[3,2-g]chromene-7-carboxamide (44.0 mg, 44%).

Example 43) (S)—N-(2-chloro-6-(4-chlorophenoxy)pyridin-4-yl)-4-(methylsulfonyl)-3,4-dihydro-2H-thieno[3,2-g]chromene-7-carboxamide

LC/MS ESI (+): 549 (M+1).

$^1$H-NMR (400 MHz, DMSO-$d_6$): 10.96 (s, 1H), 8.31 (s, 1H), 8.06 (s, 1H), 7.66 (s, 1H), 7.58 (s, 1H), 7.52 (d, 2H, J=8.80 Hz), 7.31 (s, 1H), 7.27 (d, 2H, J=8.80 Hz), 4.82 (m, 1H), 4.45-4.51 (m, 1H), 4.30-4.34 (m, 1H), 3.16 (s, 3H), 2.60-2.64 (m, 1H), 2.29-2.39 (m, 1H).

HPLC: Daicel Chiralpak IA, 0.46 cm I.D.×15 cm L, dichloromethane/ethanol=98/2, 1.0 mL/min, 254 nm, 35° C., $t_R$=3.08 min.

Example 44) (R)—N-(2-chloro-6-(4-chlorophenoxy)pyridin-4-yl)-4-(methylsulfonyl)-3,4-dihydro-2H-thieno[3,2-g]chromene-7-carboxamide

LC/MS ESI (+): 549 (M+1).

$^1$H-NMR (400 MHz, DMSO-$d_6$): 11.03 (s, 1H), 8.32 (s, 1H), 8.06 (s, 1H), 7.66 (s, 1H), 7.57 (s, 1H), 7.52 (d, 2H, J=8.79 Hz), 7.31 (s, 1H), 7.26 (d, 2H, J=8.79 Hz), 4.82 (m, 1H), 4.45-4.51 (m, 1H), 4.30-4.33 (m, 1H), 3.16 (s, 3H), 2.60-2.64 (m, 1H), 2.30-2.39 (m, 1H).

HPLC: Daicel Chiralpak IA, 0.46 cm I.D.×15 cm L, dichloromethane/ethanol=98/2, 1.0 mL/min, 254 nm, 35° C., $t_R$=3.95 min.

Compounds from Examples 45 to 49 were synthesized through the synthesis route of Example 43 and 44, and data of these compounds are listed as follows.

TABLE 4

| Ex. | Compound | Analysis data |
|---|---|---|
| 45 | (S)-N-(2-chloro-6-(4-chlorophenoxy)pyridin-4-yl)-4-fluoro-4-(methylsulfonyl)-3,4-dihydro-2H-thieno[3,2-g]chromene-7-carboxamide | LC/MS ESI (+): 567 (M + 1)<br>$^1$H-NMR (400 MHz, DMSO-$d_6$): δ 10.97 (brs, 1H), 8.26 (s, 1H), 8.24 (s, 1H), 7.63 (s, 1H), 7.58 (s, 1H), 7.45 (d, 2H, J = 8.7 Hz), 7.22 (s, 1H), 7.19 (d, 2H, J = 8.7 Hz), 4.46-4.53 (m, 1H), 4.32-4.36 (m, 1H), 3.24 (s, 3H), 2.87-2.94 (m, 1H), 2.61-2.71 (m, 1H) |
| 46 | (R)-N-(2-chloro-6-(4-chlorophenoxy)pyridin-4-yl)-4-fluoro-4-(methylsulfonyl)-3,4-dihydro-2H-thieno[3,2-g]chromene-7-carboxamide | LC/MS ESI (+): 567 (M + 1)<br>$^1$H-NMR (400 MHz, DMSO-$d_6$): δ 10.91 (brs, 1H), 8.26 (s, 1H), 8.23 (s, 1H), 7.63 (s, 1H), 7.57 (s, 1H), 7.46 (d, 2H, J = 8.7 Hz), 7.21 (s, 1H), 7.19 (d, 2H, J = 8.7 Hz), 4.46-4.49 (m, |

TABLE 4-continued

| Ex. | Compound | Analysis data |
|---|---|---|
| 47 | (S)-N-(2-chloro-6-(4-chlorophenoxy)pyridin-4-yl)-4-methyl-4-(methylsulfonyl)-3,4-dihydro-2H-thieno[3,2-g]chromene-7-carboxamide | 1H), 4.31-4.37 (m, 1H), 3.24 (s, 3H), 2.86-2.90 (m, 1H), 2.64-2.70 (m, 1H)<br>LC/MS ESI (+): 563 (M + 1)<br>$^1$H-NMR (400 MHz, DMSO-$d_6$): δ 10.94 (brs, 1H), 8.29 (s, 1H), 8.25 (s, 1H), 7.65 (s, 1H), 7.57 (s, 1H), 7.52 (d, 2H, J = 8.5 Hz), 7.30 (s, 1H), 7.25 (d, 2H, J = 8.3 Hz), 4.49-4.54 (m, 1H), 4.20-4.24 (m, 1H), 2.98 (s, 3H), 2.62 (m, 1H), 2.15-2.22 (m, 1H), 1.84 (s, 3H) |
| 48 | (R)-N-(2-chloro-6-(4-chlorophenoxy)pyridin-4-yl)-4-methyl-4-(methylsulfonyl)-3,4-dihydro-2H-thieno[3,2-g]chromene-7-carboxamide | LC/MS ESI (+): 563 (M + 1)<br>$^1$H-NMR (400 MHz, DMSO-$d_6$): δ 10.94 (brs, 1H), 8.29 (s, 1H), 8.25 (s, 1H), 7.65 (s, 1H), 7.57 (s, 1H), 7.52 (d, 2H, J = 8.5 Hz), 7.30 (s, 1H), 7.25 (d, 2H, J = 8.3 Hz), 4.49-4.54 (m, 1H), 4.20-4.24 (m, 1H), 2.98 (s, 3H), 2.62 (m, 1H), 2.15-2.22 (m, 1H), 1.84 (s, 3H) |
| 49 | (S)-N-(2-chloro-6-(3-chloro-5-methoxyphenoxy)pyridin-4-yl)-4-(methylsulfonyl)-3,4-dihydro-2H-thieno[3,2-g]chromene-7-carboxamide | LC/MS ESI (+): 580 (M + 1)<br>$^1$H-NMR (400 MHz, DMSO-$d_6$): δ 10.86 (brs, 1H), 8.23 (s, 1H), 7.99 (s, 1H), 7.62 (s, 1H), 7.51 (s, 1H), 7.22 (s, 1H), 6.89-6.90 (m, 1H), 6.85-6.86 (m, 1H), 6.74-6.76 (m, 1H), 4.74-4.75 (m, 1H), 4.39-4.44 (m, 1H), 4.23-4.27 (m, 1H), 3.73 (s, 3H), 3.09 (s, 3H), 2.52-2.57 (m, 1H), 2.28-2.32 (m, 1H) |

Examples 50) Synthesis of N-(2-chloro-6-(4-chlorophenoxy)pyridin-4-yl)-1-(methylsulfonyl)-1,2,3,4-tetrahydrothieno[2,3-g]quinoxaline-7-carboxamide tert-butyl 7-((2-chloro-6-(4-chlorophenoxy)pyridin-4-yl)carbamoyl)-1-(methylsulfonyl)-2,3-dihydrothieno[2,3-g]quinoxaline-4(1H)-carboxylate (7.0 mg, 10.78 µmol) was dissolved in CH$_2$Cl$_2$ (108.0 µl), and TFA (300 µl, 3.89 mmol) was added at 20° C. The reaction mixture was stirred at room temperature for 2 hours. The reaction mixture was purified by reversed-phase column chromatography (C18-silica gel, 0.1% formic acid in CH$_3$CN:0.1% formic acid in H$_2$O) to obtain N-(2-chloro-6-(4-chlorophenoxy)pyridin-4-yl)-1-(methylsulfonyl)-1,2,3,4-tetrahydrothieno[2,3-g]quinoxaline-7-carboxamide (2.5 mg, 42%) as white amorphous.

Examples 51) Synthesis of N-(2-chloro-6-(4-chlorophenoxy)pyridin-4-yl)-5-(methylsulfonyl)-8-oxo-5,6,7,8-tetrahydronaphtho[2,3-b]thiophene-2-carboxamide le;.4qTo a solution of N-(2-chloro-6-(4-chlorophenoxy)pyridin-4-yl)-5-(methylsulfonyl)-5,6,7,8-tetrahydronaphtho[2,3-b]thiophene-2-carboxamide (20.0 mg, 0.04 mmol) in acetic anhydride (1.0 ml, 10.58 mmol) was added chromium oxide(VI) (11.0 mg, 0.11 mmol) at 0° C. The reaction mixture was stirred at 0° C. for 2 hours. The reaction mixture was purified by reversed-phase column chromatography (C18-silica gel, 0.1% formic acid in CH$_3$CN:0.1% formic acid in H$_2$O) to obtain N-(2-chloro-6-(4-chlorophenoxy)pyridin-4-yl)-5-(methylsulfonyl)-8-oxo-5,6,7,8-tetrahydronaphtho[2,3-b]thiophene-2-carboxamide (5.0 mg, 24%) as a white amorphous.

LC/MS ESI (+): 561 (M+1)
$^1$H-NMR (400 MHz, DMSO-$d_6$): δ 11.14 (s, 1H), 8.72 (s, 1H), 8.46 (s, 1H), 8.23 (s, 1H), 7.68 (d, 1H, J=1.2 Hz), 7.52 (d, 2H, J=8.8 Hz), 7.33 (d, 1H, J=1.2 Hz), 7.26 (d, 2H, J=8.8 Hz), 4.99 (m, 1H), 3.17 (s, 3H), 3.02-3.09 (m, 1H), 2.79-2.83 (m, 1H), 2.61-2.67 (m, 2H)

Examples 52) Synthesis of N-(2-chloro-6-(4-chlorophenoxy)pyridin-4-yl)-4-(1H-pyrazol-1-yl)-3,4-dihydro-2H-thieno[3,2-g]chromene-7-carboxamide To a suspension of 4-(1H-pyrazol-1-yl)-3,4-dihydro-2H-thieno[3,2-g]chromene-7-carboxylic acid (17.0 mg, 0.06 mmol) in CH$_2$Cl$_2$ (0.3 ml) were added (COCl)$_2$ (9.6 µl, 0.11 mmol) and DMF (0.4 µl, 5.66 µmol). The reaction mixture was stirred at 40° C. for 1 hour, and concentrated under reduced pressure to obtain 4-(1H-pyrazol-1-yl)-3,4-dihydro-2H-thieno[3,2-g]chromene-7-carbonyl chloride. To the residue, 2-chloro-6-(4-chlorophenoxy)pyridin-4-amine (28.9 mg, 0.11 mmol) and 1,4-dioxane (0.3 ml) was added. The reaction mixture was stirred at 80° C. overnight. The reaction mixture was purified by reversed-phase column chromatography (C18-silica gel, 0.1% formic acid in CH$_3$CN: 0.1% formic acid in H$_2$O) to obtain N-(2-chloro-6-(4-chlorophenoxy)pyridin-4-yl)-4-(1H-pyrazol-1-yl)-3,4-dihydro-2H-thieno[3,2-g]chromene-7-carboxamide (21.0 mg, 69%) as a white solid.

LC/MS ESI (+): 537 (M+1)
$^1$H-NMR (400 MHz, DMSO-$d_6$): δ 10.77 (brs, 1H), 8.08 (s, 1H), 7.74 (d, 1H, J=2.0 Hz), 7.55 (s, 1H), 7.43-7.48 (m, 4H), 7.33 (s, 1H), 7.16-7.20 (m, 3H), 6.23-6.25 (m, 1H), 5.80 (t, 1H, J=6.2 Hz), 4.27-4.3 (m, 2H), 2.31-2.43 (m, 2H)

Compounds from Examples 53 to 55 were synthesized through the synthesis route of Example 52, and data of these compounds are listed as follows.

TABLE 5

| Ex. | Compound | Analysis data |
|---|---|---|
| 53 | N-(2-chloro-6-(4-chlorophenoxy)pyridin-4-yl)-4-(2-oxopyrrolidin-1-yl)-3,4-dihydro-2H-thieno[3,2-g]chromene-7-carboxamide | LC/MS ESI (+): 554 (M + 1)<br>$^1$H-NMR (400 MHz, DMSO-$d_6$): δ 10.93 (s, 1H), 8.23 (s, 1H), 7.66 (s, 1H), 7.59 (s, 1H), 7.48-7.53 (m, 3H), 7.24-7.29 (m, 3H), 5.43-5.47 (m, 1H), 4.29-4.42 (m, 2H), 3.24-3.29 (m, |

TABLE 5-continued

| Ex. | Compound | Analysis data |
|---|---|---|
| | | 1H), 2.95-3.00 (m, 1H), 2.35-2.44 (m, 2H), 2.11-2.22 (m, 1H), 1.90-2.03 (m, 3H) |
| 54 | N-(2-chloro-6-(4-chlorophenoxy)pyridin-4-yl)-4-cyano-3,4-dihydro-2H-thieno[3,2-g]chromene-7-carboxamide | LC/MS ESI (+): 496 (M + 1)<br>$^1$H-NMR (400 MHz, DMSO-$d_6$): δ 10.89 (brs, 1H), 8.21 (s, 1H), 7.96 (s, 1H), 7.58 (s, 1H), 7.49 (s, 1H), 7.46 (d, 2H, J = 8.8 Hz), 7.23 (s, 1H), 7.19 (d, 2H, J = 8.8 Hz), 4.57-4.60 (m, 1H), 4.23-4.26 (m, 2H), 2.22-2.33 (m, 2H) |
| 55 | 4-azido-N-(2-chloro-6-(4-chlorophenoxy)pyridin-4-yl)-3,4-dihydro-2H-thieno[3,2-g]chromene-7-carboxamide | LC/MS ESI (+): 512 (M + 1)<br>$^1$H-NMR (400 MHz, DMSO-$d_6$): δ 10.96 (brs, 1H), 8.31 (s, 1H), 8.04 (s, 1H), 7.65 (s, 1H), 7.56 (s, 1H), 7.52 (d, 2H, J = 8.8 Hz), 7.31 (s, 1H), 7.26 (d, 2H, 8.8 Hz), 5.09 (t, 1H, J = 3.9 Hz), 4.35-4.40 (m, 1H), 4.16-4.23 (m, 1H), 2.23-2.25 (m, 1H), 1.98-2.05 (m, 1H) |

Examples 56) Synthesis of N-(3-chloro-5-(2-(4-chlorophenyl)propan-2-yl)phenyl)-1-(methylsulfonyl)-2,3-dihydro-1H-thieno[3',2':4,5]benzo[1,2-b][1,4]oxazine-7-carboxamide (a) Synthesis of 1-chloro-3-nitro-5-(prop-1-en-2-yl)benzene To a suspension of 1-bromo-3-chloro-5-nitrobenzene (7.2 g, 30.59 mmol), 4,4,5,5-tetramethyl-2-(prop-1-en-2-yl)-1,3,2-dioxaborolane (5.1 g, 30.59 mmol) and $Na_2CO_3$ (9.7 g, 91.76 mmol) in DME (120.0 mL)/$H_2O$ (30.0 mL) was added Pd(PPh$_3$)$_4$ (1.8 g, 1.53 mmol). The reaction mixture was refluxed overnight. Pd(PPh$_3$)$_4$ (0.7 g, 0.61 mmol) was more added and stirred for 4 hours. After cooling to room temperature, the reaction mixture was filtered through celite. The filtrate was concentrated and the residue was extracted with EtOAc. The organic extract was washed with brine, dried over anhydrous $Na_2SO_4$, filtered and concentrated. The residue was purified by NH-silica column chromatography (hexane only) to give 1-chloro-3-nitro-5-(prop-1-en-2-yl)benzene (6.3 g) as a crude yellow oil.

$^1$H-NMR (400 MHz, CDCl$_3$): δ 8.19 (t, 1H, J=1.7 Hz), 8.11 (t, 1H, J=1.8 Hz), 7.74 (t, 1H, J=1.7 Hz), 5.30 (s, 1H), 2.19 (s, 3H)

(b) Synthesis of 1-(2-bromopropan-2-yl)-3-chloro-5-nitrobenzene

To a solution of 1-chloro-3-nitro-5-(prop-1-en-2-yl)benzene (6.3 g, 22.14 mmol) in Et$_2$O (100.0 mL) was added 33 wt % HBr in ACN (38.8 mL, 221.38 mmol). The reaction mixture was stirred at room temperature for 2 days. Sat. NaHCO$_3$ aqueous solution was added under ice bath and the resulting mixture was extracted with Et$_2$O. The organic extract was washed with sat. NaHCO$_3$ aqueous solution and brine, dried over anhydrous $Na_2SO_4$, filtered and concentrated. The residue was purified by flash column chromatography (silica gel, n-Hex:EtOAc=19:1) to obtain 1-(2-bromopropan-2-yl)-3-chloro-5-nitrobenzene (5.3 g, 62% in 2 steps) as an ivory solid.

$^1$H-NMR (400 MHz, CDCl$_3$): δ 8.34 (t, 1H, J=1.9 Hz), 8.13 (t, 1H, J=1.9 Hz), 7.26 (t, 1H, J=1.8 Hz), 2.21 (s, 6H)

(c) Synthesis of 1-chloro-3-(2-(4-chlorophenyl)propan-2-yl)-5-nitrobenzene 1-(2-Bromopropan-2-yl)-3-chloro-5-nitrobenzene (2.0 g, 7.18 mmol) and chlorobenzene (10.9 mL, 0.11 mol) were dissolved in 1,2-dichloroethane (70.0 mL), and AlCl$_3$ (2.9 g, 21.54 mmol) was added. The reaction mixture was stirred at 0° C. for 2 hours, $H_2O$ was added, and extracted with $CH_2Cl_2$. The organic extract was washed with brine, dried over anhydrous $Na_2SO_4$ and concentrated under reduced pressure. The residue was purified by reversed-phase column chromatography (C18-silica gel, 0.1% formic acid in CH$_3$CN:0.1% formic acid in $H_2O$) to obtain 1-chloro-3-(2-(4-chlorophenyl)propan-2-yl)-5-nitrobenzene (1.95 g, 88%) as a yellow oil.

$^1$H-NMR (400 MHz, CDCl$_3$): δ 8.06 (t, 1H, J=1.8 Hz), 7.99 (t, 1H, J=1.9 Hz), 7.47 (t, 1H, J=1.7 Hz), 7.29 (d, 2H, J=8.5 Hz), 7.12 (d, 2H, J=8.5 Hz), 1.70 (s, 6H)

(d) Synthesis of 3-chloro-5-(2-(4-chlorophenyl)propan-2-yl)aniline 1-chloro-3-(2-(4-chlorophenyl)propan-2-yl)-5-nitrobenzene (1.95 g, 6.28 mmol) was dissolved in MeOH/THF/$H_2O$ (65.0 mL, 10/2/1 v/v), and Zn (6.17 mg, 94.3 mmol) and NH$_4$Cl (1.68 g, 31.4 mmol) were added at room temperature. The reaction mixture was ultrasonificated at 40° C. for 90 minutes, cooled to room temperature, filtered through Celite, and concentrated under reduced pressure. The residue was purified by flash column chromatography (amine silica gel, n-Hex:EtOAc=9:1) to obtain 3-chloro-5-(2-(4-chlorophenyl)propan-2-yl)aniline (1.49 g, 85%) as a yellow oil.

LC/MS ESI (+): 280 (M+1)
$^1$H-NMR (400 MHz, CDCl$_3$): δ 7.22 (d, 2H, J=8.7 Hz), 7.14 (d, 2H, J=8.7 Hz), 6.60 (t, 1H, J=1.7 Hz), 6.50 (t, 1H, J=1.9 Hz), 6.32 (t, 1H, J=1.9 Hz), 3.64 (s, 2H), 1.59 (s, 6H)

(e) Synthesis of N-(3-chloro-5-(2-(4-chlorophenyl)propan-2-yl)phenyl)-1-(methylsulfonyl)-2,3-dihydro-1H-thieno[3',2':4,5]benzo[1,2-b][1,4]oxazine-7-carboxamide The synthesis procedure of Example 1-b was repeated except for using 3-chloro-5-(2-(4-chlorophenyl)propan-2-yl)aniline (12.1 mg, 0.04 mmol) to obtain N-(3-chloro-5-(2-(4-chlorophenyl)propan-2-yl)phenyl)-1-(methylsulfonyl)-2,3-dihydro-1H-thieno[3',2':4,5]benzo[1,2-b][1,4]oxazine-7-carboxamide (12.8 mg, 77%) as a white solid.

LC/MS ESI (+): 575 (M+1)
$^1$H-NMR (400 MHz, DMSO-$d_6$): δ 10.47 (s, 1H), 8.24 (s, 1H), 8.16 (s, 1H), 7.89 (s, 1H), 7.65 (s, 1H), 7.50 (t, 1H, J=1.6 Hz), 7.39 (d, 2H, J=8.6 Hz), 7.28 (d, 2H, J=8.6 Hz), 7.03 (m, 1H), 4.37 (t, 2H, J=4.2 Hz), 3.91 (t, 2H, J=4.4 Hz), 3.19 (s, 3H), 1.66 (s, 6H).

EXPERIMENTAL EXAMPLES

Experiments were performed as shown below for the compounds prepared in Examples above.

Experimental Example 1) Experiment on the Inhibition of STAT3 and STAT1 Activities via Reporter Gene Assay 1-1) Experiment on the Inhibition of STAT3 Activity A human prostate cancer cell line (LNCaP stable cell line; plasmid pSTAT3-TA-luc), which contains a stably operating STAT3 promoter, was cultured in RPMI1640 medium (Cat No. 11875, Life Technologies) containing 10% fetal bovine serum (FBS) (Cat No. SH30396, Thermo Scientific) and 150 μg/mL G-418 solution (Cat No. 04 727 894 001, Roche). The reporter gene assay using LNCaP stable cell line was performed in RPMI1640 medium containing 3% DCC-FBS without G-418 solution. LNCaP stable cells were plated in two (2) white 96-well plates with 30,000 cells/50 μL in each well. The cells were cultured at 37° C., under 5% $CO_2$ for 24 hours, and then treated with the compounds listed in Examples which were diluted in various concentrations. Subsequently, IL-6 was added to each well with a final concentration of 10 ng/mL. Upon completion of the treatment with the compounds and IL-6, the cells were cultured at 37° C., under 5% $CO_2$ for 24 hours. The plates were observed under microscope and drug precipitation and particular findings were investigated and recorded.

The luciferase assay and the cell viability assay were performed respectively with one of the two plates. For the luciferase assay, the liquid media in the 96-well plate was removed, and then, 20 μL of passive cell lysis buffer was added to each well. After shaking the plate for 30 minutes, luciferase activities of each well were measured in a PHERAstar™ microplate reader (BMG LABTECH) using a luciferase assay system (Cat No. E1501, Promega). For the cell viability assay, the 96-well plate was placed at room temperature for 30 minutes, added with 20 μL/well of CellTiter-Glo solution (Cat No. G7573, Promega), and shaken for 10 minutes in order to measure cytotoxicity caused by the compounds listed in Examples with a PHERAstar™ microplate reader (BMG LABTECH). Wells without 0.1% DMSO and stimulation were used as a negative control and wells with 0.1% DMSO and stimulation were used as a positive control.

1-2) Experiment on the Inhibition of STAT1 Activity

A human osteosarcoma cell line (U2OS stable cell line; pGL4-STAT1-TA-luc), which contains a stably operating STAT1 promoter, was cultured in McCoy 5'A medium (Cat No. 16600, Life Technologies) containing 10% FBS (Cat No. SH30396, Thermo Scientific) and 1000 μg/mL G418 solution (Cat No. 04 727 894 001, Roche). The reporter gene assay using U2OS stable cell line was performed in McCoy 5'A medium containing 10% FBS without G-418 solution. U2OS stable cells were plated in two (2) white 96-well plates with 25,000 cells/50 μL in each well. The cells were cultured at 37° C., under 5% $CO_2$ for 24 hours, and then treated with the compounds listed in Examples which were diluted in various concentrations. Subsequently, IFN-γ was added to each well with a final concentration of 50 ng/mL. Upon completion of the treatment with the compounds and IFN-γ, the cells were cultured at 37° C., under 5% $CO_2$ for 8 hours. The plates were observed under microscope and drug precipitation and particular findings were investigated and recorded.

The luciferase assay and the cell viability assay were performed respectively with one of two plates. For the luciferase assay, the liquid media in the 96-well plate was removed, and then, 20 μL of passive cell lysis buffer was added to each well. After shaking the plate for 30 minutes, luciferase activities of each well were measured in a PHERAstar™ microplate reader (BMG LABTECH) using a luciferase assay system (Cat No. E1501, Promega). For the cell viability assay, the 96-well plate was placed at room temperature for 30 minutes, added with 20 μL/well of CellTiter-Glo solution (Cat No. G7573, Promega), and shaken for 10 minutes in order to measure cytotoxicity caused by the compounds listed in Examples with a PHERAstar™ microplate reader (BMG LABTECH). Wells without 0.1% DMSO and stimulation were used as a negative control and wells with 0.1% DMSO and stimulation were used as a positive control.

The results of evaluation on the inhibitory effect of the compounds listed in the Examples on the dimerization of STAT3 and STAT1 obtained via the STAT3 and STAT1 reporter gene assays are shown in Table 6 below.

TABLE 6

| Ex. | $IC_{50}$ (μM) pSTAT3 | $IC_{50}$ (μM) pSTAT1 | Ex. | $IC_{50}$ (μM) pSTAT3 | $IC_{50}$ (μM) pSTAT1 |
|---|---|---|---|---|---|
| 1 | 0.0026 | >50 | 2 | 0.17 | >50 |
| 3 | 0.01 | >50 | 4 | 0.93 | >50 |
| 5 | 0.76 | >50 | 6 | 0.0030 | >50 |
| 7 | 0.012 | >50 | 8 | 0.024 | >50 |
| 9 | 0.029 | >50 | 10 | 0.0026 | >50 |
| 11 | 0.0060 | >50 | 12 | 0.0030 | >50 |
| 13 | 0.0081 | >50 | 14 | 0.029 | >50 |
| 15 | 0.018 | >50 | 16 | 0.0051 | >50 |
| 17 | 0.0039 | >50 | 18 | 0.015 | >50 |
| 19 | 0.0084 | >50 | 20 | 0.010 | >50 |
| 21 | 0.011 | >50 | 22 | 0.030 | >50 |
| 23 | 0.0063 | >50 | 24 | 0.0062 | >50 |
| 25 | 0.011 | >50 | 26 | 0.0073 | >50 |
| 27 | 0.0078 | >50 | 28 | 0.0051 | >50 |
| 29 | 0.0059 | >50 | 30 | 0.02 | >50 |
| 31 | 0.008 | >50 | 32 | 0.016 | >50 |
| 33 | 0.0098 | >50 | 34 | 0.0064 | >50 |
| 35 | 0.010 | >50 | 36 | 0.014 | >50 |
| 37 | 0.0062 | >50 | 38 | 0.0088 | >50 |
| 39 | 0.014 | >50 | 40 | 0.0087 | >50 |
| 41 | 0.011 | >50 | 42 | 0.023 | >50 |
| 43 | 0.018 | >50 | 44 | 1.5 | >50 |
| 45 | 0.0039 | >50 | 46 | 0.14 | >50 |
| 47 | 0.0045 | >50 | 48 | 0.15 | >50 |
| 49 | 0.0066 | >50 | 50 | 0.0082 | >50 |
| 51 | 0.10 | >50 | 52 | 0.10 | >50 |
| 53 | 5.2 | >50 | 54 | 0.18 | 16.6 |
| 55 | 0.039 | 17.9 | 56 | 0.0028 | >50 |

As shown in Table 6, the compounds according to the present invention exhibited excellent inhibitory effects against the activity of STAT3 protein but showed almost no inhibitory effect against the activity of STAT1 protein.

Experimental Example 2) Cell Growth Inhibition Assay

The inhibitory effects of the compounds of the present invention against the growth of cancer cells were evaluated as shown below. The cancer cell lines including stomach cancer cell line (NCI-N87) and breast cancer cell line (MDA-MB-468) were cultured under the protocol provided by each supplier. Each type of cells to be used in experiments was sub-cultured in a 96-well plate by counting the exact number of cells using Tali™ Image-based Cytometer (Life Technologies). In a 96-well plate, NCI-N87 was employed with 5,000 cells/well; and MDA-MB-468 was employed with 10,000 cells/well. The cells were treated with the compounds listed in Examples which were diluted in various concentrations. Upon completion of the compounds treatment, NCI-N87 cells were cultured at 37° C. under 5% $CO_2$ for 96 hours, and MDA-MB-468 cells were cultured at 37° C. in air for 96 hours. Subsequently, the cells were observed under microscope and drug precipitation and particular findings were investigated and recorded. And then, the 96-well plate was placed at room temperature for 30 minutes, added with 20 μL/well of CellTiter-Glo solution (Cat No. G7573, Promega) and shaken for 10 minutes, followed by being subjected to the measurement using PHERAstar™ microplate reader (BMG LABTECH) according to the supplier's general luminometer protocol. Wells where only culture liquid added without cell plating were used as a negative control, whereas wells where culture liquid containing 0.1% DMSO instead of the compounds listed in Examples were used as a positive control.

The results of the inhibitory effects of the compounds prepared in Examples against the growth of cancer cells are shown in Tables 7 to 8 below.

TABLE 7

| Ex. | $IC_{50}$ (μM) NCI-N87 | Ex. | $IC_{50}$ (μM) NCI-N87 | Ex. | $IC_{50}$ (μM) NCI-N87 | Ex. | $IC_{50}$ (μM) NCI-N87 |
|---|---|---|---|---|---|---|---|
| 1 | 0.0083 | 2 | 1.2 | 3 | 0.045 | 4 | 4.1 |
| 5 | 0.72 | 6 | 0.0055 | 7 | 0.027 | 8 | 0.031 |
| 9 | 0.067 | 10 | 0.0060 | 11 | 0.01 | 12 | 0.0018 |
| 13 | 0.025 | 14 | 0.16 | 15 | 0.035 | 16 | 0.021 |
| 17 | 0.011 | 18 | 0.020 | 19 | 0.0061 | 20 | 0.0094 |
| 21 | 0.018 | 22 | 0.071 | 23 | 0.0056 | 24 | 0.0038 |
| 25 | 0.010 | 26 | 0.0072 | 27 | 0.0049 | 28 | 0.0056 |
| 29 | 0.0046 | 30 | 0.025 | 31 | 0.009 | 32 | 0.031 |
| 33 | 0.024 | 34 | 0.0092 | 37 | 0.0095 | 40 | 0.023 |
| 41 | 0.021 | 42 | 0.024 | 43 | 0.015 | 44 | 1.8 |
| 45 | 0.0056 | 46 | 0.56 | 47 | 0.0064 | 48 | 0.79 |
| 49 | 0.018 | 50 | 0.0091 | 51 | 0.20 | 52 | 0.40 |
| 53 | 4.4 | 54 | 0.32 | 55 | 1.2 | 56 | 0.019 |

TABLE 8

| Ex. | $IC_{50}$ (μM) MDA-MB-468 | Ex. | $IC_{50}$ (μM) MDA-MB-468 | Ex. | $IC_{50}$ (μM) MDA-MB-468 | Ex. | $IC_{50}$ (μM) MDA-MB-468 |
|---|---|---|---|---|---|---|---|
| 7 | 0.0065 | 8 | 0.0032 | 9 | 0.023 | 10 | 0.0019 |
| 11 | 0.0052 | 12 | 0.0028 | 13 | 0.0066 | 14 | 0.026 |
| 15 | 0.0089 | 16 | 0.0039 | 17 | 0.0023 | 18 | 0.0043 |
| 19 | 0.0025 | 20 | 0.0024 | 21 | 0.0051 | 22 | 0.017 |
| 23 | 0.0028 | 24 | 0.0024 | 25 | 0.0049 | 26 | 0.0046 |
| 27 | 0.0029 | 28 | 0.0020 | 29 | 0.0029 | 30 | 0.0085 |
| 31 | 0.0022 | 32 | 0.0089 | 33 | 0.0093 | 34 | 0.0023 |
| 37 | 0.0047 | 40 | 0.0086 | 41 | 0.012 | 42 | 0.0078 |
| 43 | 0.0029 | 44 | 0.086 | 45 | 0.0025 | 46 | >0.10 |
| 47 | 0.0017 | 48 | >0.10 | 49 | 0.0059 | 51 | 0.050 |
| 52 | 0.12 | 53 | 0.71 | 54 | 0.075 | 55 | 0.078 |

As shown in Tables 7 to 8, the compounds according to the present invention exhibited excellent inhibitory effects against the growth of various kinds of cancer cells.

What is claimed is:

1. A compound selected from the group consisting of a heterocyclic derivative represented by formula (I), and a pharmaceutically acceptable salt, and a stereoisomer thereof:

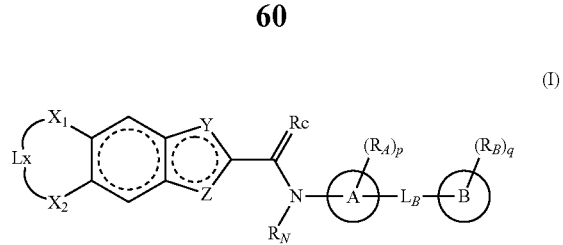

(I)

wherein
one of $X_1$ and $X_2$ is —C(-Rx)(-Rx")-, —C(-Rx')(-Rx")-, —N(Rx)-, or —N(-Rx')-, and the other is —C(-Rx")(-Rx")-, —N(-Rx")-, —C(=O)—, or —O—;

Rx is

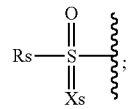

Xs is =O or =NH;
Rs is $C_{1-6}$alkyl, halo$C_{1-6}$alkyl, $C_{1-6}$alkoxy-$C_{1-6}$alkyl, $C_{1-6}$alkylcarbonyl-$C_{1-6}$alkyl, $C_{2-7}$alkenyl, amino, or amino$C_{1-6}$alkyl;
Rx' is halo$C_{1-6}$alkyl, $C_{1-4}$alkoxycarbonyl, cyano, nitro, azido, amino, or a 3-6 membered heterocyclyl unsubstituted or substituted with Rx";
Rx" is each independently hydrogen, halogen, nitro, amino, $C_{1-6}$alkyl, $C_{1-6}$alkoxy, halo$C_{1-6}$alkoxy, carbamoyl$C_{1-6}$alkyl, $C_{1-6}$alkylamino-$C_{1-6}$alkyl, or di$C_{1-6}$alkylamino-$C_{1-6}$alkyl;
one of Y and Z is —S— or —NH—, and the other is —CH= or —N=;
Lx is a saturated or unsaturated $C_{1-4}$ hydrocarbon chain not containing or containing one O or N atom, and unsubstituted or substituted with halogen;
A and B are each independently benzene or 5- to 7-membered heterocycle containing one to three N, O, or S atoms;
Rc is =O, =NH, =N(—$C_{1-6}$alkyl), or =N(—OH);
$R_N$ is hydrogen or $C_{1-6}$alkyl;
$L_B$ is —[C(—$R_L$)(—$R_L$')]$_m$—, —O—, wherein m is an integer of 1 or 2, $R_L$ and $R_L$' are each independently hydrogen, hydroxy, halogen or $C_{1-6}$alkyl, or $R_L$ and $R_L$' are linked together to form $C_{1-6}$alkylene;
$R_A$ is hydrogen, halogen, cyano, $C_{1-6}$alkyl, halo$C_{1-6}$alkyl, cyano$C_{1-6}$alkyl, $C_{1-6}$alkylcarbonyl, $C_{1-6}$alkoxy, halo$C_{1-6}$alkoxy, cyano$C_{1-6}$alkoxy, $C_{1-6}$alkylamino, di$C_{1-6}$alkylamino, $C_{1-6}$alkylthio, $C_{1-6}$alkylaminocarbonyl, diC$_{1-6}$alkylaminocarbonyl, C$_{2-8}$alkynyl, C$_{1-6}$alkoxycarbonylamino-C$_{1-6}$alkoxy, aminoC$_{1-6}$alkoxy, or 3- to 6-membered heterocyclyl;

R$_B$ is hydrogen, halogen, hydroxy, cyano, nitro, amino, oxo, aminosulfonyl, sulfonylamido, C$_{1-6}$alkylamino, C$_{1-6}$alkyl, haloC$_{1-6}$alkyl, cyanoC$_{1-6}$alkyl, C$_{1-6}$alkoxy, haloC$_{1-6}$alkoxy, cyanoC$_{1-6}$alkoxy, C$_{3-8}$cycloalkyloxy, C$_{2-8}$alkenyl, C$_{2-8}$alkenyloxy, C$_{2-8}$alkynyl, C$_{2-8}$alkynyloxy, C$_{1-6}$alkylamino-C$_{1-6}$alkoxy, diC$_{1-6}$alkylamino-C$_{1-6}$alkoxy, C$_{1-6}$alkoxy-carbonyl, carbamoyl, carbamoyl-C$_{1-6}$alkoxy, C$_{1-6}$alkylthio, C$_{1-6}$alkylsulfinyl, C$_{1-6}$alkylsulfonyl, 5- to 10-membered heterocyclyl, 5- to 10-membered heterocyclyl-C$_{1-6}$alkyl, 5- to 10-membered heterocyclyl-C$_{1-6}$alkoxy, or 5- to 10-membered heterocyclyl-oxy;

p is an integer of 0 to 4, and, when p is 2 or higher, R$_A$ moieties are the same as or different from each other;

q is an integer of 0 to 4, and, when q is 2 or higher, R$_B$ moieties are the same as or different from each other; and each of said heterocycle and heterocyclyl moieties independently contains at least one heterogroup selected from the group consisting of —O—, —NH—, —N═, —S—, —S(═O)— and —S(═O)$_2$—.

2. The compound according to claim 1, wherein
one of Y and Z is —S— or —NH—, and the other is —CH═;
Lx is a saturated C$_{1-3}$ hydrocarbon chain not containing or containing one O or N atom, and unsubstituted or substituted with halogen;
Rx is

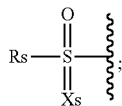

Xs is ═O or ═NH;
Rs is C$_{1-6}$alkyl or haloC$_{1-6}$alkyl;
Rx' is haloC$_{1-6}$alkyl, cyano, nitro, amino, azido, or a 5- to 6-membered heterocyclyl containing at least one heteroatom selected from the group consisting of N, S and O and unsubstituted or substituted with oxo; and
Rx" is hydrogen, halogen, C$_{1-6}$alkyl, or C$_{1-4}$alkoxycarbonyl.

3. The compound according to claim 2, wherein
Y is —CH═;
Z is —S—;
Rc is ═O;
R$_N$ is hydrogen;
Lx is a saturated C$_{1-3}$ hydrocarbon chain not containing or containing oxygen atom in the chain, and unsubstituted or substituted with halogen;
X$_1$ is —C(-Rx)(-Rx")-, —C(-Rx')(-Rx")-, or —N(Rx)-;
X$_2$ is —C(-Rx")(-Rx")-, —C(═O)—, —N(-Rx")-, or —O—;
Rx is

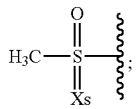

Xs is ═O or ═NH;
Rx' is haloC$_{1-6}$alkyl, cyano, nitro, amino, azido, or a 5- to 6-membered heterocyclyl containing 1 to 2 heteroatoms selected from N and O and unsubstituted or substituted with oxo; and
Rx" is hydrogen, halogen, C$_{1-6}$alkyl, or C$_{1-4}$alkoxycarbonyl.

4. The compound according to claim 3, wherein
one of A and B is benzene, and the other is a 5- to 7-membered heteroaryl containing 1 to 3 nitrogen atoms;
B
L$_B$ is —[C(—R$_L$)(—R$_L$')]$_m$— or —O—, wherein m is 1, R$_L$ and R$_L$' are each independently hydrogen, hydroxy, halogen or C$_{1-6}$alkyl, or R$_L$ and R$_L$' are linked together to form C$_{2-5}$alkylene;
R$_A$ is halogen, C$_{1-6}$alkoxycarbonylamino-C$_{1-6}$alkoxy, aminoC$_{1-6}$alkoxy, or 3- to 6-membered heterocyclyl;
R$_B$ is halogen, C$_{1-6}$alkyl, C$_{1-6}$alkoxy, haloC$_{1-6}$alkyloxy, C$_{2-6}$alkenyloxy, C$_{3-10}$carbocyclyl-oxy, or 3- to 10-membered heterocyclyl-C$_{1-3}$alkoxy; and
each of said heteroaryl, heterocycle and heterocyclyl moieties independently contains 1 to 3 heteroatoms selected from the group consisting of O, N and S.

5. The compound according to claim 1, wherein
X$_1$ is —N(-Rx)-;
X$_2$ is —C(-Rx")(-Rx")- or —N(-Rx")-;
Y is —CH═;
Z is —S—;
Rc is ═O;
R$_N$ is hydrogen;
Rx is

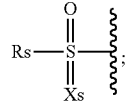

Xs is ═O;
Rs is methyl; and
Rx" is the same as defined in claim 1.

6. The compound according to claim 1, wherein
X$_1$ is —CH(-Rx)-;
X$_2$ is —N(-Rx")-;
Y is —CH═;
Z is —S—;
Rc is ═O;
R$_N$ is hydrogen;
Lx is ethylene;
Rx is

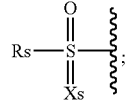

Xs is ═O;
Rs is methyl; and
Rx" is the same as defined in claim 1.

7. The compound according to claim 1, wherein
X$_1$ is —C(-Rx)(-Rx")-;
X$_2$ is —O—;
Y is —CH═;
Z is —S—;

Rc is =O;
R_N is hydrogen;
Lx is ethylene;
Rx is

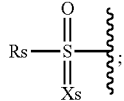

Xs is =O;
Rs is methyl; and
Rx" is the same as defined in claim 1.
8. The compound according to claim 1, wherein
X_1 is —C(-Rx')(-Rx")-;
X_2 is —O—;
Y is —CH=;
Z is —S—;
Rc is =O;
R_N is hydrogen;
Lx is ethylene; and
Rx' and Rx" are the same as defined in claim 1.
9. The compound according to claim 1, wherein
X_1 is —CH(-Rx)-;
X_2 is —C(-Rx")(-Rx")- or —C(=O)—;
Y is —CH=;
Z is —S—;
Rc is =O;
R_N is hydrogen;
Lx is ethylene;
Rx is

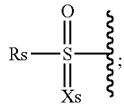

Xs is =O;
Rs is methyl; and
Rx" is the same as defined in claim 1.
10. The compound according to claim 1, wherein
X_1 is —CH(-Rx)-;
X_2 is —C(-Rx")(-Rx")-;
Y is —CH=;
Z is —S—;
Rc is =O;
R_N is hydrogen;
Lx is —CH_2—O—;
Rx is

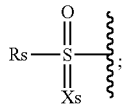

Xs is =O;
Rs is methyl; and
Rx" is the same as defined in claim 1.
11. The compound according to claim 1, wherein
X_1 is —C(-Rx)(-Rx")- or —N(Rx)-;
X_2 is —O—;
Y is —NH—;

Z is —CH=;
Rc is =O;
R_N is hydrogen;
Lx is propylene; and
Rx and Rx" are the same as defined in claim 1.
12. The compound according to claim 1, which is selected from the group consisting of:
1) N-(2-chloro-6-(4-chlorophenoxy)pyridin-4-yl)-1-(methylsulfonyl)-2,3-dihydro-1H-thieno[3',2':4,5]benzo[1,2-b][1,4]oxazine-7-carboxamide;
2) N-(2-chloro-6-(4-chlorophenoxy)pyridin-4-yl)-3,3-dimethyl-1-(methylsulfonyl)-2,3-dihydro-1H-thieno[3',2':4,5]benzo[1,2-b][1,4]oxazine-7-carboxamide;
3) N-(2-chloro-6-(4-chlorophenoxy)pyridin-4-yl)-1-(methylsulfonyl)-1,2,3,4-tetrahydrothieno[3',2':4,5]benzo[1,2-b][1,4]oxazepine-8-carboxamide;
4) N-(2-chloro-6-(4-chlorophenoxy)pyridin-4-yl)-8,8-dimethyl-5-(methylsulfonyl)-5,6,7,8-tetrahydrothieno[2,3-g]quinoline-2-carboxamide;
5) tert-butyl 7-((2-chloro-6-(4-chlorophenoxy)pyridin-4-yl)carbamoyl)-1-(methylsulfonyl)-2,3-dihydrothieno[2,3-g]quinoxaline-4(1H)-carboxylate;
6) N-(2-chloro-6-(4-chlorophenoxy)pyridin-4-yl)-5-(methylsulfonyl)-5,6,7,8-tetrahydrothieno[2,3-g]quinoline-2-carboxamide;
7) N-(2-chloro-6-(4-chlorophenoxy)pyridin-4-yl)-4-methyl-1-(methylsulfonyl)-1,2,3,4-tetrahydrothieno[2,3-g]quinoxaline-7-carboxamide;
8) N-(2-chloro-6-(4-chlorophenoxy)pyridin-4-yl)-4-(methylsulfonyl)-3,4-dihydro-2H-thieno[3,2-g]chromene-7-carboxamide;
9) N-(2-chloro-6-(4-chlorophenoxy)pyridin-4-yl)-5-(methylsulfonyl)-2,3,4,5-tetrahydrothieno[3',2':4,5]benzo[1,2-b]oxepine-8-carboxamide;
10) N-(2-chloro-6-(4-chlorophenoxy)pyridin-4-yl)-5-(methylsulfonyl)-5,6,7,8-tetrahydronaphtho[2,3-b]thiophene-2-carboxamide;
11) N-(2-chloro-6-(4-chlorophenoxy)pyridin-4-yl)-4-methyl-4-(methylsulfonyl)-3,4-dihydro-2H-thieno[3,2-g]chromene-7-carboxamide;
12) N-(2-chloro-6-(4-chlorophenoxy)pyridin-4-yl)-5-(methylsulfonyl)-5,8-dihydro-6H-thieno[3,2-g]isochromene-2-carboxamide;
13) N-(2-chloro-6-(4-chlorophenoxy)pyridin-4-yl)-4-fluoro-4-(methylsulfonyl)-3,4-dihydro-2H-thieno[3,2-g]chromene-7-carboxamide;
14) N-(2-chloro-6-(4-chlorophenoxy)pyridin-4-yl)-8,8-difluoro-5-(methylsulfonyl)-5,6,7,8-tetrahydronaphtho[2,3-b]thiophene-2-carboxamide;
15) N-(2-chloro-6-(p-tolyloxy)pyridin-4-yl)-4-(methylsulfonyl)-3,4-dihydro-2H-thieno[3,2-g]chromene-7-carboxamide;
16) N-(2-chloro-6-(3-(trifluoromethyl)phenoxy)pyridin-4-yl)-4-(methylsulfonyl)-3,4-dihydro-2H-thieno[3,2-g]chromene-7-carboxamide;
17) N-(2-chloro-6-(4-(trifluoromethyl)phenoxy)pyridin-4-yl)-4-(methylsulfonyl)-3,4-dihydro-2H-thieno[3,2-g]chromene-7-carboxamide;
18) N-(2-chloro-6-(3,5-dichlorophenoxy)pyridin-4-yl)-4-(methylsulfonyl)-3,4-dihydro-2H-thieno[3,2-g]chromene-7-carboxamide;
19) N-(2-chloro-6-(4-chloro-3-fluorophenoxy)pyridin-4-yl)-4-(methylsulfonyl)-3,4-dihydro-2H-thieno[3,2-g]chromene-7-carboxamide;
20) N-(2-chloro-6-(4-chloro-3-methylphenoxy)pyridin-4-yl)-4-(methylsulfonyl)-3,4-dihydro-2H-thieno[3,2-g]chromene-7-carboxamide;

21) N-(2-chloro-6-(4-chloro-2-methylphenoxy)pyridin-4-yl)-4-(methylsulfonyl)-3,4-dihydro-2H-thieno[3,2-g]chromene-7-carboxamide;
22) N-(2-chloro-6-(4-methoxyphenoxy)pyridin-4-yl)-4-(methylsulfonyl)-3,4-dihydro-2H-thieno[3,2-g]chromene-7-carboxamide;
23) N-(2-chloro-6-(4-chloro-2-fluorophenoxy)pyridin-4-yl)-4-(methylsulfonyl)-3,4-dihydro-2H-thieno[3,2-g]chromene-7-carboxamide;
24) N-(2-chloro-6-(3,4-dichlorophenoxy)pyridin-4-yl)-4-(methylsulfonyl)-3,4-dihydro-2H-thieno[3,2-g]chromene-7-carboxamide;
25) N-(2-chloro-6-(3-chlorophenoxy)pyridin-4-yl)-4-(methylsulfonyl)-3,4-dihydro-2H-thieno[3,2-g]chromene-7-carboxamide;
26) N-(2-chloro-6-(4-fluorophenoxy)pyridin-4-yl)-4-(methylsulfonyl)-3,4-dihydro-2H-thieno[3,2-g]chromene-7-carboxamide;
27) N-(2-chloro-6-(3-chloro-4-fluorophenoxy)pyridin-4-yl)-4-(methylsulfonyl)-3,4-dihydro-2H-thieno[3,2-g]chromene-7-carboxamide;
28) N-(2-chloro-6-(4-(trifluoromethoxy)phenoxy)pyridin-4-yl)-4-(methylsulfonyl)-3,4-dihydro-2H-thieno[3,2-g]chromene-7-carboxamide;
29) N-(2-chloro-6-(3-(trifluoromethoxy)phenoxy)pyridin-4-yl)-4-(methylsulfonyl)-3,4-dihydro-2H-thieno[3,2-g]chromene-7-carboxamide;
30) N-(2-chloro-6-(3-chloro-5-methoxyphenoxy)pyridin-4-yl)-4-(methylsulfonyl)-3,4-dihydro-2H-thieno[3,2-g]chromene-7-carboxamide;
31) N-(2-chloro-6-(3-chloro-5-fluorophenoxy)pyridin-4-yl)-4-(methylsulfonyl)-3,4-dihydro-2H-thieno[3,2-g]chromene-7-carboxamide;
32) N-(2-chloro-6-(3-fluoro-5-methoxyphenoxy)pyridin-4-yl)-4-(methylsulfonyl)-3,4-dihydro-2H-thieno[3,2-g]chromene-7-carboxamide;
33) N-(2-chloro-6-(m-tolyloxy)pyridin-4-yl)-4-(methylsulfonyl)-3,4-dihydro-2H-thieno[3,2-g]chromene-7-carboxamide;
34) N-(2-chloro-6-(3,4-difluorophenoxy)pyridin-4-yl)-4-(methylsulfonyl)-3,4-dihydro-2H-thieno[3,2-g]chromene-7-carboxamide;
35) N-(2-chloro-6-(5-chloro-2-fluorophenoxy)pyridin-4-yl)-4-(methylsulfonyl)-3,4-dihydro-2H-thieno[3,2-g]chromene-7-carboxamide;
36) N-(2-chloro-6-(3-chloro-2-fluorophenoxy)pyridin-4-yl)-4-(methylsulfonyl)-3,4-dihydro-2H-thieno[3,2-g]chromene-7-carboxamide;
37) N-(2-chloro-6-(5-chloro-2-methylphenoxy)pyridin-4-yl)-4-(methylsulfonyl)-3,4-dihydro-2H-thieno[3,2-g]chromene-7-carboxamide;
38) N-(2-chloro-6-(3-chloro-4-methylphenoxy)pyridin-4-yl)-4-(methylsulfonyl)-3,4-dihydro-2H-thieno[3,2-g]chromene-7-carboxamide;
39) N-(2-chloro-6-(2-(trifluoromethyl)phenoxy)pyridin-4-yl)-4-(methylsulfonyl)-3,4-dihydro-2H-thieno[3,2-g]chromene-7-carboxamide;
40) N-(2-chloro-6-(2-(trifluoromethoxy)phenoxy)pyridin-4-yl)-4-(methylsulfonyl)-3,4-dihydro-2H-thieno[3,2-g]chromene-7-carboxamide;
41) N-(2-chloro-6-(2-fluoro-3-methylphenoxy)pyridin-4-yl)-4-(methylsulfonyl)-3,4-dihydro-2H-thieno[3,2-g]chromene-7-carboxamide;
42) N-(2-chloro-6-(4-chloro-2-methoxyphenoxy)pyridin-4-yl)-4-(methylsulfonyl)-3,4-dihydro-2H-thieno[3,2-g]chromene-7-carboxamide;
43) (S)—N-(2-chloro-6-(4-chlorophenoxy)pyridin-4-yl)-4-(methylsulfonyl)-3,4-dihydro-2H-thieno[3,2-g]chromene-7-carboxamide;
44) (R)—N-(2-chloro-6-(4-chlorophenoxy)pyridin-4-yl)-4-(methylsulfonyl)-3,4-dihydro-2H-thieno[3,2-g]chromene-7-carboxamide;
45) (S)—N-(2-chloro-6-(4-chlorophenoxy)pyridin-4-yl)-4-fluoro-4-(methylsulfonyl)-3,4-dihydro-2H-thieno[3,2-g]chromene-7-carboxamide;
46) (R)—N-(2-chloro-6-(4-chlorophenoxy)pyridin-4-yl)-4-fluoro-4-(methylsulfonyl)-3,4-dihydro-2H-thieno[3,2-g]chromene-7-carboxamide;
47) (S)—N-(2-chloro-6-(4-chlorophenoxy)pyridin-4-yl)-4-methyl-4-(methylsulfonyl)-3,4-dihydro-2H-thieno[3,2-g]chromene-7-carboxamide;
48) (R)—N-(2-chloro-6-(4-chlorophenoxy)pyridin-4-yl)-4-methyl-4-(methylsulfonyl)-3,4-dihydro-2H-thieno[3,2-g]chromene-7-carboxamide;
49) (S)—N-(2-chloro-6-(3-chloro-5-methoxyphenoxy)pyridin-4-yl)-4-(methylsulfonyl)-3,4-dihydro-2H-thieno[3,2-g]chromene-7-carboxamide;
50) N-(2-chloro-6-(4-chlorophenoxy)pyridin-4-yl)-1-(methylsulfonyl)-1,2,3,4-tetrahydrothieno[2,3-g]quinoxaline-7-carboxamide;
51) N-(2-chloro-6-(4-chlorophenoxy)pyridin-4-yl)-5-(methylsulfonyl)-8-oxo-5,6,7,8-tetrahydronaphtho[2,3-b]thiophene-2-carboxamide;
52) N-(2-chloro-6-(4-chlorophenoxy)pyridin-4-yl)-4-(1H-pyrazol-1-yl)-3,4-dihydro-2H-thieno[3,2-g]chromene-7-carboxamide;
53) N-(2-chloro-6-(4-chlorophenoxy)pyridin-4-yl)-4-(2-oxopyrrolidin-1-yl)-3,4-dihydro-2H-thieno[3,2-g]chromene-7-carboxamide;
54) N-(2-chloro-6-(4-chlorophenoxy)pyridin-4-yl)-4-cyano-3,4-dihydro-2H-thieno[3,2-g]chromene-7-carboxamide;
55) 4-azido-N-(2-chloro-6-(4-chlorophenoxy)pyridin-4-yl)-3,4-dihydro-2H-thieno[3,2-g]chromene-7-carboxamide;
56) N-(3-chloro-5-(2-(4-chlorophenyl)propan-2-yl)phenyl)-1-(methylsulfonyl)-2,3-dihydro-1H-thieno[3',2':4,5]benzo[1,2-b][1,4]oxazine-7-carboxamide, and
a pharmaceutically acceptable salt and a stereoisomer thereof.

13. A pharmaceutical composition comprising the compound as defined in claim 1 as an active ingredient.

14. A method for treating a disease associated with the activation of STAT3 protein in a mammal in need thereof, which comprises administering the compound as defined in claim 1 to the mammal, wherein the disease associated with the activation of STAT3 protein is selected from the group consisting of breast cancer, lung cancer, stomach cancer, prostate cancer, uterine cancer, ovarian cancer, kidney cancer, pancreatic cancer, liver cancer, colon cancer, skin cancer, head and neck cancer, thyroid cancer, osteosarcoma, acute or chronic leukemia, multiple myeloma, B- or T-cell lymphoma, non-Hodgkin's lymphoma, rheumatoid arthritis, psoriasis, hepatitis, inflammatory bowel disease, Crohn's disease, diabetes, macular degeneration, human papillomavirus infection, and tuberculosis.

* * * * *